United States Patent [19]
Bohinski et al.

[11] Patent Number: 5,976,873
[45] Date of Patent: Nov. 2, 1999

[54] NUCLEIC ACID SEQUENCES CONTROLLING LUNG CELL-SPECIFIC GENE EXPRESSION

[75] Inventors: Robert J. Bohinski; Jeffrey A. Whitsett, both of Cincinnati, Ohio

[73] Assignee: Children's Hospital Medical Center, Cincinnati, Ohio

[21] Appl. No.: 08/442,809

[22] Filed: May 17, 1995

Related U.S. Application Data

[63] Continuation-in-part of application No. 08/245,356, May 18, 1994, abandoned.
[51] Int. Cl.$^6$ .......................... C12N 15/63; C12N 15/11; B32B 5/16
[52] U.S. Cl. .................. 435/320.1; 536/24.1; 428/402.2
[58] Field of Search ........................ 435/320.1; 536/24.1; 428/402.2

[56] References Cited

U.S. PATENT DOCUMENTS

| | | | |
|---|---|---|---|
| 4,835,260 | 5/1989 | Shoemaker | 530/397 |
| 5,240,846 | 8/1993 | Collins et al. | 435/371 |
| 5,672,510 | 9/1997 | Eglitis et al. | 435/325 |

OTHER PUBLICATIONS

Pilot–Matias et al. Structure and organization of the gene encoding human pulmonary surfactant proteilpid SP–B. DNA vol. 8 pp. 75–86, 1989.
Rosenfeld et al. In vivo transter of the human cystic fibrosis transmembrane conductance regulator gene to the airway epithelium Cell vol. 68 143–155, 1992.
Wert et al. Transcriptional elements from the juman SP–C gene direct expression in the primordial respiratory epithelium of transgenic mice. Dev. Biol. vol. 156 426–443, 1993.
Bohinski et al. Therapeutic strategies for surfactant protein SP–B deficiency. J. Cellular Biochem. Suppl. 17E Abstract SZ 400, p. 241, 1993.
Bingle et al. Role of hepatocyte nuclear factor–3 alpha and hepatocyte nuclear factor–3 beta in clara cell secretory protein gene expression in the bronchiolar epithelium. Biochem. J. vol. 308 197–202, 1995.
Stripp et al. cis–acting elements that confer lung epithelial cell expression of the CC10 gene. J. Biol. Chem. vol. 267 14703–14712, 1992.
Hagen et al. Tissue–specific expression, hormonal regulation and 5'–flanking gene region of the rat clara cell 10 kDa protein: comparison to rabbit uteroglobin. Nucleic Acids Research vol. 18 2939–2946, 1990.
Toonen et al. The lung enriched transcription factor TTF–1 and the ubiquitously expressed proteins Sp1 and Sp3 interact with elements located in the minimal promoter of the rat clara cell secretory protein gene. Biochem. J. vol. 316 467–473, 1996.
Orkin et al. Report and recommendations of the panel to assess the NIH investment in research on gene therapy, 1995.
Glasser, et al., *Proc. Natl. Acad. Sci. USA*, vol. 84, pp. 4007–4011 (Jun. 1987).
Glasser, et al., *J. of Bio. Chem.*, vol. 263, No. 21, pp. 10326–10331 (Jul. 25, 1988).
Korfhagen, et al., *Amer. Physiological Society*, vol. 263 pp. L546–L554 (1992).
Stripp, et al., *J. of Bio. Chem.*, vol. 267, No. 21, pp. 14703–14712 (Jul. 25, 1992).
Francis–Lang, et al., *Molecular and Cellular Biology*, vol. 12, No. 2, pp. 576–588 (Feb. 1992).
Wert, et al., *Developmental Biology*, vol. 156, pp. 426–443 (1993).
Bohinski, et al., *J. of Bio. Chem.*, vol. 268, No. 15, pp. 11160–11166 (May 25, 1993).
Sawaya, et al., *Molecular and Cellular Biology*, vol. 13, No. 7, pp. 3860–3871 (Jul. 1993).
Smith, et al., *Human Gene Therapy*, vol. 5, pp. 29–35 (1994).
Overdier, et al., *Molecular and Cellular Biology*, vol. 14, No. 4, pp. 2755–2766 (Apr. 1994).

*Primary Examiner*—John S. Brusca
*Attorney, Agent, or Firm*—Elliot M. Olstein; Raymond J. Lillie

[57] ABSTRACT

An oligonucleotide which includes at least one nucleic acid sequence which binds to at least one nuclear protein found in lung cells, such as TTF-1 protein. The oligonucleotide may be contained in a vector. The at least one nuclear protein provides for lung cell-specific expression of the vector upon binding of the at least one nucleic acid sequence to the at least one nuclear protein. Such vector may also include genes encoding therapeutic agents, and may be employed for delivering genes encoding therapeutic agents to lung cells.

12 Claims, 50 Drawing Sheets

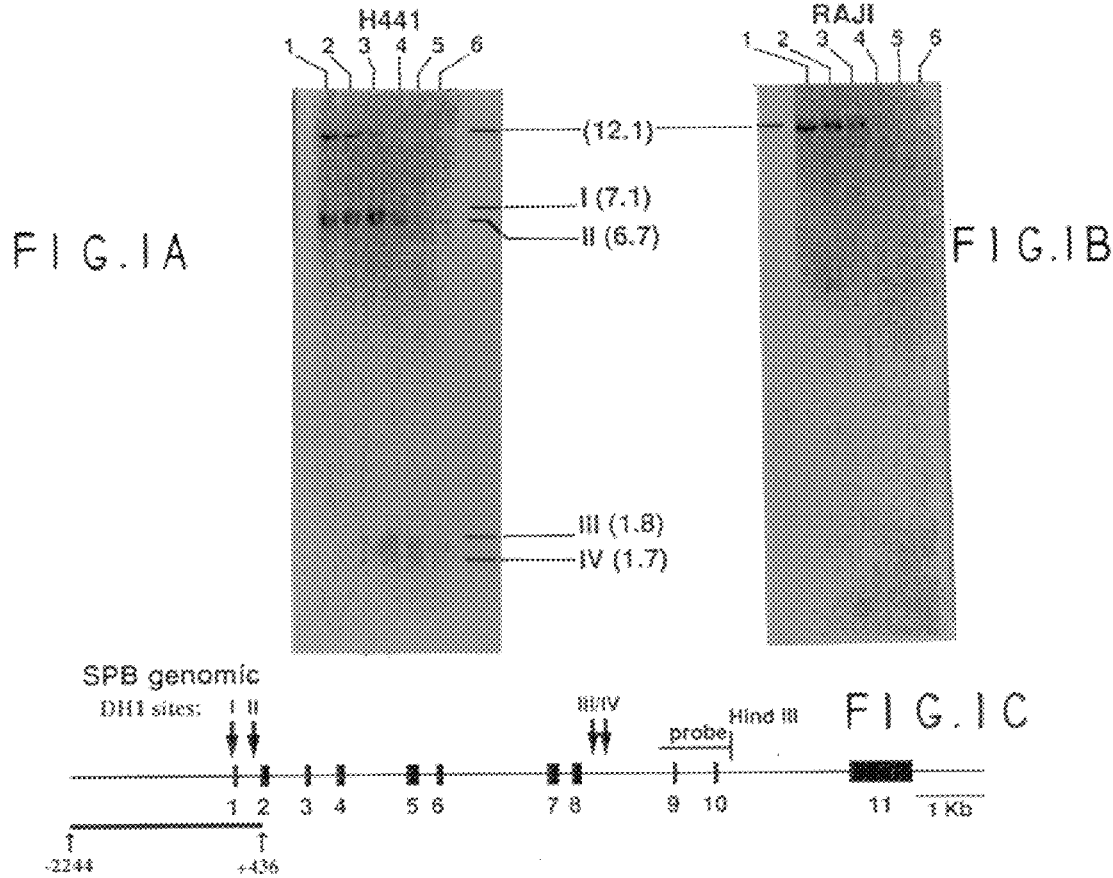

FIG. 6

```
                                    -107 SPB-f1  -93          -90  SPB-f2      -73
CTGGGAAAAGGTGGGATCAAGCACCTGGAGGGCTCTTCAGAGCAAAGACAAACACTGAGGTCGC
GACCCTTTCCACCCTAGTTCGTGGACCTCCCGAGAAGTCTCGTTTCTGTTTGACTCCAGCG
                                                            -111         -77

-69 SPB-f3 -51        -46   SPB-f4         -27
TGCCACTCCTACAGAGCCCACGCCCCAGCTATAAGGGGCCATGCCCCAAGCAGGTAC
ACGGTGAGGATGTCTCGGGGGTGCGGGGTCGATATTCCCCGGTACGGGGTTCGTCCCATG
    -49                                          -26

.15  SPB-f5  .33
CCAGGCTGCAGAGGTGCCATGGCTGAGTCACACCTGCTGCAGTGGCTGCTGCTGCCCA
GGTCCGACGTCTCCACGGTACCGACTCAGTGTGGACGTCACCGACGACGACGACGGGT
 ↑                              .14            .32
 .1
```

FIG. 7A

```
            -120                                                            -67
Mo   -120 TGAGAAAG-ACCTGGAGGGCTCTCAAGA-CACAGGCAAACACTGAGGTCAGCCTGT -67
              ||||| ||||||||||||||| ||||| ||||| |||||||||||||||| |||| |
Hu   -118 GATCAAGCACCTGGAGGGCTCTTCAGAGCAAAGACAAACACTGAGGTCGCTGCCA -64
                                      ||||||||||||||||||||||||||||||||
          CTAGTTCGTGGACCTCCCGAGAAGTCTCGTTTCTGTTTGACTCCAGCGACGGT
          ─────────────────────────────
                      SPB-f1                              SPB-f2
```

```
TGT3     ACCCAGGACTTGTTTGTTCTAT
SPB-f2       CGACCTCAGTGTTTGTCTTTGC
TTR-S            TCTGATTATTGACTTATTCAAGCG
```

```
SPB-f1    -113AGCACCTGGAGGGCTCTTCAGAGC-90
              TCGTGGACCTCCCGAGAAGTCTCG
5' f1     ATCAAGCACCTGGAGGGC
          TAGTTCGTGGACCTCCCG
3' f1                         GGGCTCTTCAGAGCAAAG
                              CCCGAGAAGTCTCGTTTC
```

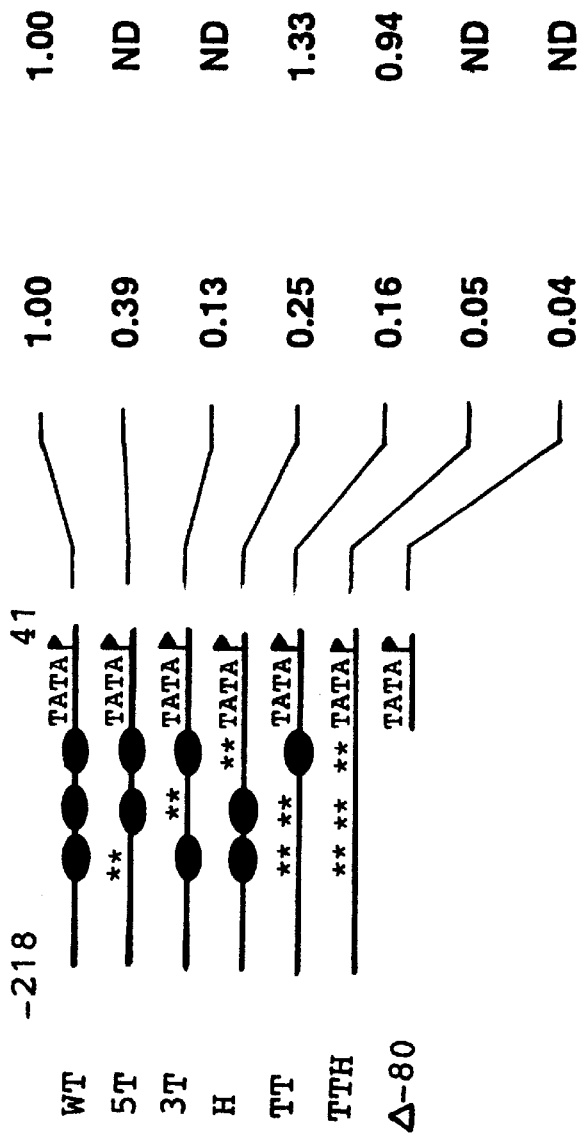

FIG. IIC
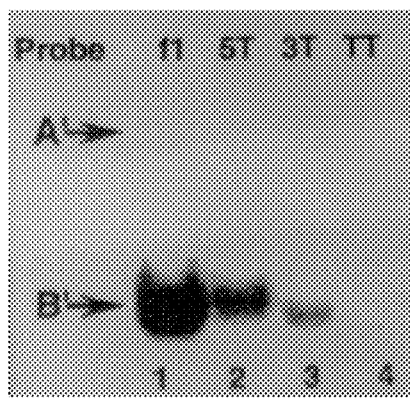
FIG. IID
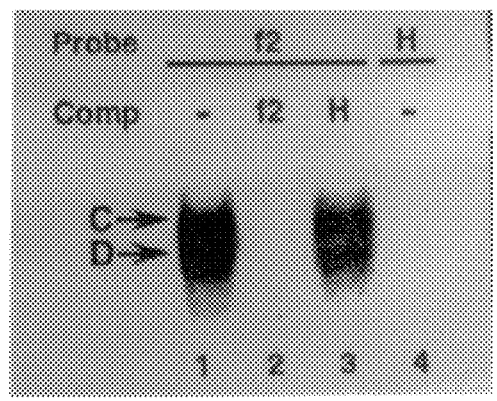
FIG. 12
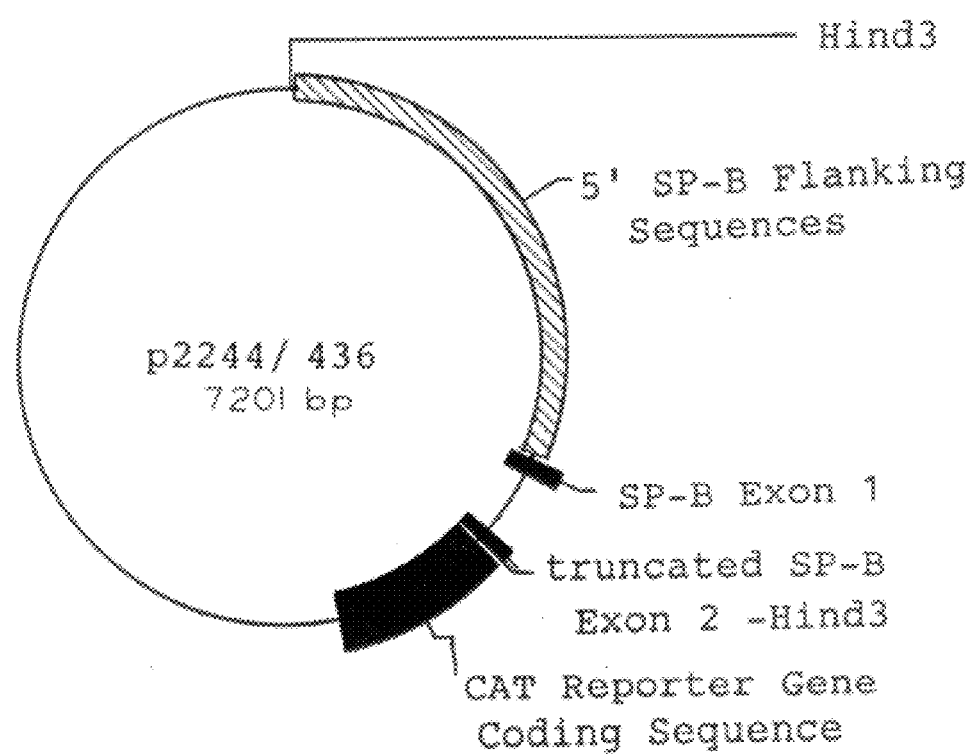

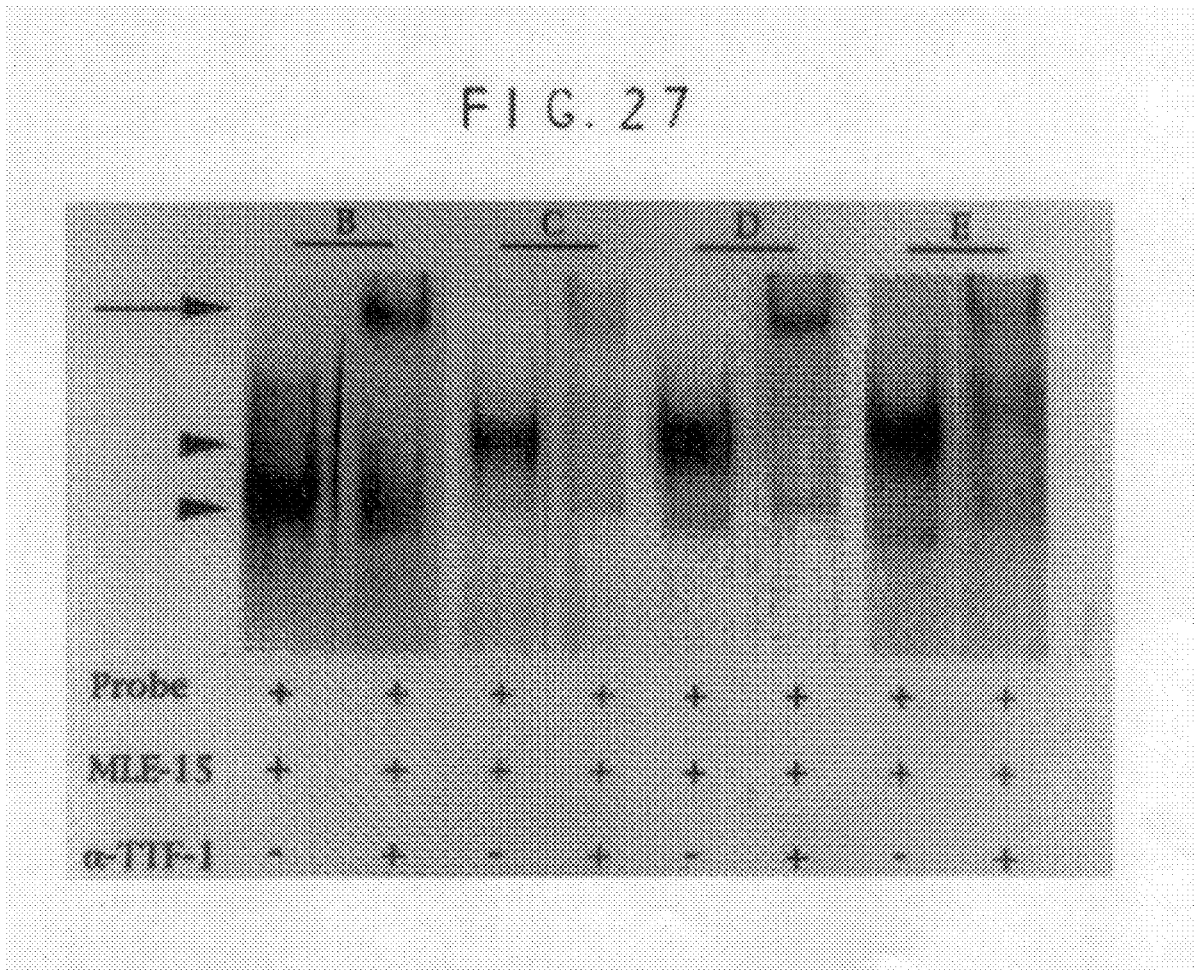

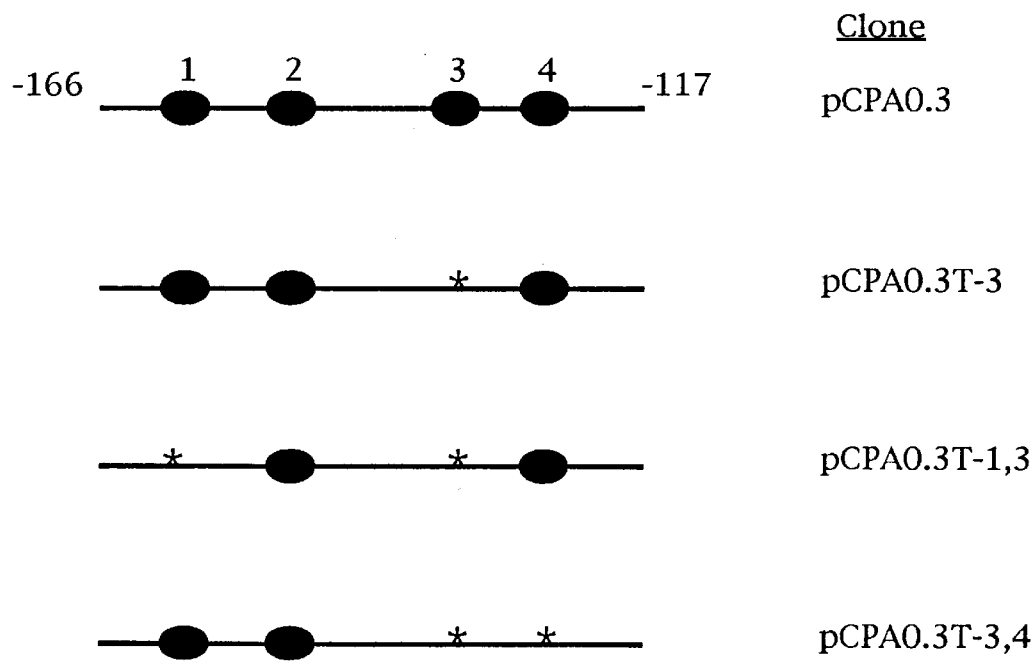
FIG. 28A
FIG. 28B
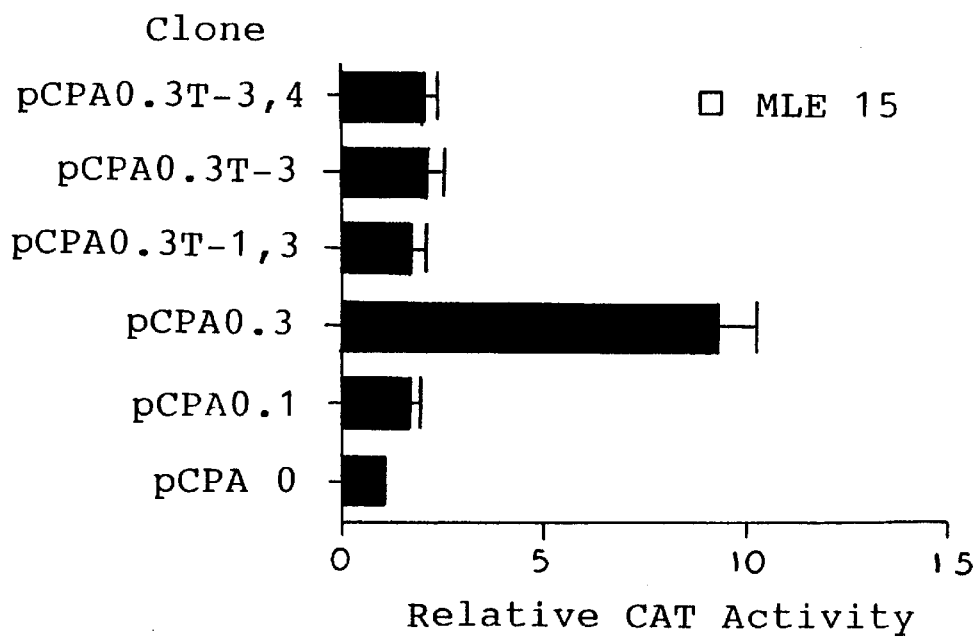

FIG. 34A

```
Ba      5' -CAGGGCTTGCCCTGGGTTAAGAGCCAGGCA
        3' -GTCCCGAACGGGACCCAATTCTCGGTCCGT

Ba^m    5' -TAGGGggatCCCTGGGTTAAGAGCTAGGCA
        3' -GTCCCcctaGGGACCTAATTCTCGGTCCGT Bb      5' -GCCAGGCAGGAAGCTCTCAAGAGCATTG
        3' -CGGTCCGTCCTTCGAGAGTTCTCGTAAC Bb^m    5' -GCCAGGTAGGAAGCTCTatccAGCATTG
        3' -CGGTCCGTCCTTCGAGAtaggTCGTAAC Bc      5' -AGCATTGCTCAAGAGTAGAGGGGGCCTGGG
        3' -TCGTAACGAGTTCTCATCTCCCCCGGACCC Bc^m    5' -AGCATTGCTatccAGTAGAGGGGGCCTGGG
        3' -TCGTAACGAtaggTCATCTCCCCCGGACCC
```

FIG. 34B

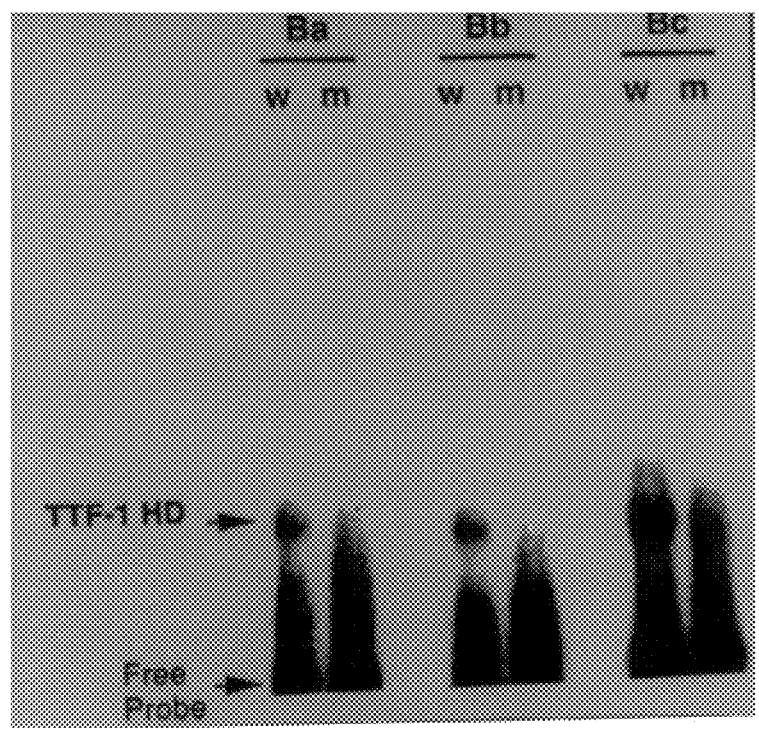

FIG. 39

| FIG. 39A | FIG. 39B |
|---|---|
| FIG. 39C | FIG. 39D |

FIG. 39A

AACTTAAAGGTGTTTACCTTGTCATCAGCATGTAAGCTAATTATCTCGGGCAAG

CTGGTGGCTGCCTAAAACCTGGCGCCGGCTAAAACAAACGCGAGGCAGCCCCC

+1
CGTGTACATCCAACAAGATGGCGTTAAGGTAACACCAGAATATTTGGCAAAGG

TTCCTCCTCTTCCTTCCTCCTCCAGCCGCCGCCGAATC ATGTCGATGAGTCC
                                                  MetSerMetSerPr

GGAAAGCTACAAGAAAGTGGGCATGGAGGGCGGCGGCTCGGGGCTCCGCTGGC
GluSerTyrLysLysValGlyMetGluGlyGlyGlyLeuGlyAlaProLeuAl

CAGCACGCCGTGGGGCACCACGGCGCCGTCACCGCCGCTACCACATGACGGCG
GlnHisAlaValGlyHisHisGlyAlaValThrAlaAlaTyrHisMetThrAla

ACGGCAACCTGGGCAACATGAGCGAGCTGCCGCCGTACCAGGACACCATGAGGA
AsnGlyAsnLeuGlyAsnMetSerGluLeuProProTyrGlnAspThrMetArgA

CTTCCCCGCCA GTAAGTGAGGCCGCCCCACTGCGGGCCGCGGCTGAGCTC
PheProAlaIle

CGCTGGGCATCAGGGAGGGCGGCCCGGCAGCGGCGCCAGGGACTTGGGTGCGGG

ACTTGGTAGCGCTGGGGTCCTGCGGTCAGATGCGGGTACTCGGCGTCTCCTAGG

CAAGGGAAGCGACCCCGAGCTCAAGGAGCAGGGGCGAGCAGAGCGCGGAGAGGC

GCCCGGCCCGGCCCTCTCTCCAGCGGAGTCTGGGCAGGTGGGAGGACTCGCAGT

TGACAGGAGAGAAGCCAAGAGGCAAAGCGTCTGGGGGCTCCAGCTTTTGGAAGT

CCCCAGCTCCCGGCCTGAGCCCAGTTCGCCGCTGTGGCCAGCTAATCCTAATG

CACTGCGTCTTTTGGTTCGAAAGAGGGAACTGAGACTGAGGGAGGGCAGCCAGG

TGGGGCAGGCGCTGGCAGTTCCCCGCGGATGGGCCTCTTGGGCCCCAGCGCTAG

GCCAATGGCGCGGAAAACAGGGGTGGCCTGGCTCGGCCTGGCCCCGGCCGACGC

Match with FIG. 39C

Match with FIG. 39B

FIG. 39B

| Sequence | Position |
|---|---|
| ATGTAGCCTTCTATTGTCTTGTTGCTTTAGCGCTTACGCCCCGCCT | -43 |
| GAGCCTCCACTCAAGCCAATTAAGGAGGACTCGGTCCACTCCGTTA | 58 |
| GAGAAAAAAAAAGCAGCGAGCTTCGCCTTCCCCCTCTCCCTTTTTT | 158 |
| AAAGCACACGACTCCGTTCTCAGTGTCTGACATCTTGAGTCCCCTGGA<br>oLysHisThrThrProPheSerValSerAspIleLeuSerProLeuGlu | 258 |
| GGCGTACAGGCAGGGCCAGGCGGCACCGCCAACAGCGGCATGCAG<br>aAlaTyrArgGlnGlyGlnAlaAlaProProThrAlaAlaMetGln | 358 |
| GCGGGGGTGCCCCAGCTCTCGCACTCCGCCGTGGGGGGCTACTGCA<br>AlaGlyValProGlnLeuSerHisSerAlaValGlyGlyTyrCys | 458 |
| ACAGCGCCTCTGGCCCCGGATGGTACGGCGCCAACCCAGACCCGCG<br>snSerAlaSerGlyProGlyTrpTyrGlyAlaAsnProAspProArg | 558 |
| AGGAGGTGCCGCGAGAGGCTCCAGAAGGCGCGGCGCGGCAGGCTGCG | 658 |
| AGCTGGGGATGCTTCCCCCTGCTCGGCTGGGGGTCCAAGAACAGGC | 758 |
| CGCCGGTGGACTGGCAGCTCTGCTCGGCGCAGAAGACCTCGGGGAGC | 858 |
| TAGACCGGGCCAGGAGGGAGGCTGCCCTGTTGGGAGGCACTCGAGC | 958 |
| TCCAGAGGGGACTCTAAGGGTCCGAGCAGGTGCCCTCACTGGGGCC | 1058 |
| CAACACCCCTCTCCTAACCTCTCCAAACTGGGGTCTACCGTAGGA | 1158 |
| CTCTGACCCGGCTGGGCACGAAAGGAGCAGAAGCGGCCTTTCCCC | 1258 |
| GTTGGGGCTGTGAGCGCTCCAGTACAGCCCCTCGACGGTACGGCC | 1358 |
| GCTGCCTGGGTCAGGAGGGCGCCGTGGGTTGGGGCGGGCCGGGCGG | 1458 |
| TGTGCGTTTGTCGCTTACAG TCTCCCGCTTCATGGGCCCGGCGAGC<br>SerArgPheMetGlyProAlaSer | 1558 |

MATCH WITH FIG. 39A

MATCH WITH FIG. 39D

FIG. 39C

MATCH WITH FIG. 39A

GGCATGAACATGAGCGGCATGGGCGGCCTGGGCTCGCTGGGGGACGTGAGCAAG
GlyMetAsnMetSerGlyMetGlyGlyLeuGlySerLeuGlyAspValSerLys

TCTTCTCGCAGGCGCAGGTGTACGAGCTGGAGCGACGCTTCAAGCAACAGAAGT
LeuPheSerGlnAlaGlnValTyrGluLeuGluArgArgPheLysGlnGlnLysT

GACGCCCACGCAGGTCAAGATCTGGTTCCAGAACCACCGCTACAAAATGAAGCG
ThrProThrGlnValLysIleTrpPheGlnAsnHisArgTyrLysMetLysAr

GGCGGCGGCGGGGCGGCGGGGCACCGGGTGCCCGCAGCAGCAACAGGCTCAG
GlyGlyGlyGlyGlyGlyGlyGlyThrGlyCysProGlnGlnGlnAlaGln

GCAAACCGTGCCAGGCGGGTGCCCCGCGCCGGCGCCGCCAGCCTACAAGGCC
GlyLysProCysGlnAlaGlyAlaProAlaProGlyAlaAlaSerLeuGlnGlyH

GGCAGCGGCCATCTCCGTGGGCAGCGGTGGCGCCGGCCTTGGCGCACACCCGGG
AlaAlaAlaIleSerValGlySerGlyGlyAlaGlyLeuGlyAlaHisProGl

GCCGCCAGCCCCGCGGCGCTGCAGGGCCAGGTATCCAGCCTGTCCCACCTGAAC
AlaAlaSerProAlaAlaLeuGlnGlyGlnValSerSerLeuSerHisLeuAsn

ACGGTCGGACCTGGTGA  GAGGACGCCGGGCCGGCCCTAGCCCAGCGCTCTGC
TyrGlyArgThrTrp***

CCACGCGCTTCGACTTTTCTTAACAACCTGGCCGCGTTTAGACCAAGGAACAAA

ACTCTAAAATTTGTGGGTTTTTTTTTTAAAAAAAAGAAAATGAAAAACAACCA

CAGCTTTGGGGGTGTCTTTTTTTGGTGATTCAAATGGGTTTTCCACGCTAGGC

TAAAGACCAAACTTCACTGTGGGCACACTCTGCCAGCAAAGAGGACTCGCTTGT

GGGAGAGGAAAGAGTCTTCAACATAACCCACTTGTCACTGACACAAAGGAAGTG

CCTCCGCGAAAATAGTTTGTTTAATGTGAACTTGTAGCTGTAAAACGCTGTCAA

TAAAAAGAAAAACCACTCCCAGTCCCCAGCCCTTCACATTTTTTATGGGCATTG

TCTTTTTCTGTTGTAACTTATGTAGATATTTGGCTTAAATATAGTTCCTAAGAA

MATCH WITH FIG.39B

FIG. 39D

```
AACATGGCCCCGCTGCCAAGCGCGCCGCGCAGGAAGCGCCGGGTGC     1658
AsnMetAlaProLeuProSerAlaProArgArgLysArgArgVal

ACCTGTCGGCGCCGGAGCGCGAGCACCTGGCCAGCATGATCCACCT     1758
yrLeuSerAlaProGluArgGluHisLeuAlaSerMetIleHisLeu

CCAGGCCAAGGACAAGGCGGCGCAGCAGCAACTGCAGCAGGACAGC     1858
gGlnAlaLysAspLysAlaAlaGlnGlnGlnLeuGlnGlnAspSer

CAGCAGTCGCCGCGACGCGTGGCGGTGCCGGTCCTGGTGAAAGACG     1958
GlnGlnSerProArgArgValAlaValProValLeuValLysAsp

ACGCGCAGCAGCAGGCGCAGCACCAGGCGCAGGCCGCGCAGGCGGC     2058
isAlaGlnGlnGlnAlaGlnHisGlnAlaGlnAlaAlaGlnAlaAla

CCACCAGCCAGGCAGCGCAGGCCAGTCTCCGGACCTGGCGCACCAC     2158
yHisGlnProGlySerAlaGlyGlnSerProAspLeuAlaHisHis
```
MATCH WITH FIG.39C
```
TCCTCGGGCTCGGACTACGGCACCATGTCCTGCTCCACCTTGCTAT     2258
SerSerGlySerAspTyrGlyThrMetSerCysSerThrLeuLeu

CTCACGCTTCCCTCCTGCCCGCCACACAGACCACCATCCACCGCTGCT    2358

AAAACCACAAAGGCCAAACTGCTGGACGTCTTTCTTTCCCCCCCCC     2458

AGCGCATCCAATCTCAAGGAATCTTTAAGCAGAGAAGGGCATAAAA     2558

GGGGCACAGATTGGAGAGGGCTCTGTGCTGACATGGCTCTGGACTC     2658

AAATACCAGGATTTTTTTTTTTTTTTTGAAGGGAGGACGGGAGCTG     2758

CCCCCTCCCCGGCACCCTCTGGCCGCCTAGGCTCAGCGGCGACCGC     2858

AAGTTGGACTAAATGCCTAGTTTTAGTAATCTGTACATTTTGTTG     2958

ACAAATCTGTGTATATTATTTGGCAGTTTGGTATTTGCGGCGTCAG    3058

GCTTCTAATAAATTATACAAATTAAAAACGATTCTTTTT           3151
```

NUCLEIC ACID SEQUENCES CONTROLLING LUNG CELL-SPECIFIC GENE EXPRESSION

This application is a continuation-in-part of application Ser. No. 08/245,356, filed May 18, 1994, now abandoned.

This invention relates to nucleic acid sequences which bind to nuclear proteins found in lung cells. More particularly, this invention relates to nucleic acid sequence (s) which bind to nuclear protein(s) found in lung cells, such as TTF-1 protein, and vectors containing said nucleic acid sequence(s), whereby lung-specific expression of the vector is effected upon binding of said nucleic acid sequence(s) to said nuclear protein(s).

BACKGROUND OF THE INVENTION

Lung-specific gene products include the lung surfactant proteins SP-A, SP-B, SP-C, SP-D, and Clara cell secretory protein (CCSP). The recent cloning of these gene products, the determination of their expression patterns in vivo (Weaver, et al., *Biochem. J.*, Vol. 273, page 249–264 (1991); Wert, et al., *Dev. Biol.*, Vol. 156, pgs. 426–443 (1993); Stripp, et al., *Genomics*, Vol. 20, pgs. 27–35 (1994)); and the characterization of cell lines that support their expression (O'Reilly, et al., *Biochem. Biophys. Acta*, Vol. 970, pgs. 194–204 (1988); Gazdar, et al., *Cancer Res.*, Vol. 50, pgs. 5481–5487 (1990); Wikenheiser, et al., *Proc. Nat. Acad. Sci. USA*, Vol. 90, pgs. 11029–11033 (1993)) provide a model system to investigate the mechanisms involved in lung-specific gene expression.

The control of tissue-specific gene expression is thought to occur largely at the level of transcription initiation. Consistent with this observation is that appropriate cis-active sequences from tissue-specific genes often are sufficient to target expression of a reporter gene to the tissue of origin in vivo. (Jaenisch, *Science*, Vol. 240, pgs. 1468–1474 (1988).) Studies have shown that DNA-binding proteins interact specifically with these sequences to stimulate gene transcription (Maniatis, et al., *Science*, Vol. 236, pgs. 1237–1244 (1987): Mitchell, et al., *Science*, Vol. 245, pgs. 371–378 (1989); Johnson, et al., *Ann. Rev. Biochem.*, Vol. 58, pgs. 799–839 (1989).) Liver-specific cis-active elements have been studied extensively, and several transcription factors including HNF-1, HNF-3, HNF-4, C/EBP, and DBP (Simmons, et al., *Genes & Dev.*, Vol. 4, pgs. 695–711 (1990)) bind these regions and appear to act together to regulate transcription of liver-specific genes (Costa, et al., *Mol. Cell. Biol.*, Vol. 9, pgs. 1415–1425 (1991)). None of these proteins appears to be restricted to liver cells. (Xanthopoulus, et al., *Proc. Nat. Acad. Sci. USA*, Vol. 88, pgs. 3807–3811 (1991)). This suggests that mechanisms other than the restricted expression of a transcription factor to a single cell type are responsible for the tissue-specific activity of these genetic elements. This could involve interaction between DNA bound factors at a unique cis-active environment (Milos, et al, *Genes and Dev.*, Vol. 6, pgs. 991–1004 (1992); Nerlov, et al., *Genes and Dev.*, Vol. 8, pgs. 350–362 (1994)) or between a DNA bound factor and a non-DNA bound cofactor (Mendel, et al., *J. Biol. Chem.*, Vol. 266, pgs. 677–680 (1991)).

Recently, it has appeared that the mechanisms of transcriptional control of tissue-specific genes in the liver and lung may be related. This is suggested by the expression of HNF-3 and CCAAT enhancer binding protein-α (C/EBP) family members in the lung, (Lai, et al., *Genes and Dev.*, Vol. 5, pgs. 416–427 (1991); Cao, et al., *Genes & Dev.*, Vol. 5, pgs. 1538–1552 (1991); Xanthopoulus, et al., 1991), and by the finding that HNF-3 proteins bind to a region of the CCSP gene promoter in vitro (Sawaya, et al., *Mol. Cell. Biol.*, Vol. 13, pgs. 3860–3871 (1993); Bingle, et al; *Biochem J.*, Vol. 295, pgs. 227–232 (1993)).

Despite the work accomplished in the above studies, a need still exists to isolate and obtain genetic elements which will direct lung cell specific expression of genes of interest.

DETAILED DESCRIPTION OF THE INVENTION

In accordance with an aspect of the present invention, there is provided an oligonucleotide or polynucleotide including at least one nucleic acid sequence which binds to at least one nuclear protein found in lung cells.

The term "nucleic acid sequence" as used herein, means a DNA or RNA molecule, and more particularly a linear series of deoxyribonucleotides or ribonucleotides connected one to the other by phosphodiester bonds between the 3' and 5' carbons of the adjacent pentoses. Depending upon the use herein, such term includes complete and partial gene sequences, and includes polynucleotides as well.

In a preferred embodiment, the at least one nucleic acid sequence which binds to a nuclear protein found in lung cells is contained in the proximal promoter region of the human surfactant protein B (or SP-B) gene. Such proximal promoter region is found from base −218 to base +41 of the human surfactant protein B gene. In one embodiment, the at least one nucleic acid sequence which binds to a nuclear protein found in lung cells is contained in a portion of the proximal promoter region of the human surfactant protein B gene, as defined by the region from base −118 to base −64 of the human surfactant protein B gene.

In another embodiment, the at least one nucleic acid sequence which binds to a nuclear protein found in lung cells is contained in a portion of the proximal promoter region of the human surfactant protein B gene, as defined by the region from base −111 to base −73 of the human surfactant protein B gene.

In another embodiment, the at least one nucleic acid sequence which binds to a nuclear protein found in lung cells is contained in the distal promoter region of the human surfactant protein B (or SP-B) gene. Such distal promoter region is found from base −439 to base −331 of the human surfactant protein B gene. In one embodiment, the at least one nucleic acid sequence which binds to a nuclear protein found in lung cells is contained in one or more portions of the distal promoter region of the human surfactant protein B gene, as defined by the regions from (i) base −439 to base −410; or (ii) base −417 to base −390; or (iii) base −396 to base −367 of the human surfactant protein B gene.

Applicants have found that such proximal promoter region and distal promoter region of the human SP-B gene contain enhancer-like elements. Such enhancer-like elements may bind to nuclear proteins found specifically in lung cells, or to ubiquitous nuclear proteins (i.e., nuclear proteins found in lung cells as well as other cell types). The binding of such enhancer-like elements to nuclear proteins in lung cells enables one to express genes specifically in lung cells transduced with vectors including such enhancer-like elements.

In another embodiment, the at least one nucleic acid sequence which binds to a nuclear protein found in lung cells is contained in the promoter region of the CCSP protein gene. In yet another embodiment, the at least one nucleic acid sequence which binds to a nuclear protein found in lung cells is contained in the promoter region of the mouse surfactant protein C (SP-C) gene.

In yet another embodiment, the at least one nucleic acid sequence which binds to a nuclear protein found in lung cells is contained in a portion of the promoter region of the mouse surfactant protein C (SP-C) gene, as defined by the region from base −180 to base −160 of the mouse surfactant protein C gene.

In another embodiment, the at least one nucleic acid sequence which binds to a nuclear protein found in lung cells is contained in the promoter region of the human surfactant protein C (or SP-C) gene. In one embodiment, the at least one nucleic acid sequence which binds to a nuclear protein found in lung cells is contained in a portion of the promoter region of the human SP-C gene as defined by the region from base −180 to base −160 of the human SP-C gene.

In another embodiment, the at least one nucleic acid sequence which binds to a nuclear protein found in lung cells is contained in a portion of the promoter region of the mouse surfactant protein A (SP-A) gene as defined by the region from base −255 to base −57 of the mouse SP-A gene.

In yet another embodiment, the at least one nucleic acid sequence which binds to a nuclear protein found in lung cells is contained in a portion of the promoter region of the mouse surfactant protein A (SP-A) gene as defined by the region from base −231 to base −168 of the mouse SP-A gene.

In a further embodiment, the at least one nucleic acid sequence which binds to a nuclear protein found in lung cells is contained in the distal promoter region of the mouse surfactant protein B (SP-B) gene. In one embodiment, the at least one nucleic acid sequence which binds to a nuclear protein found in lung cells is contained in one or more portions of the distal promoter region of the mouse surfactant protein B gene, as defined by the regions from (i) base −345 to base −331; or (ii) base −370 to base −356; or (iii) base −332 to base −318; or (iv) base −296 to base −282 of the mouse surfactant protein B gene.

In another embodiment, the at least one nucleic acid sequence which binds to a nuclear protein found in lung cells is contained in the proximal promoter region of the mouse surfactant protein B gene. In one embodiment, the at least one nucleic acid sequence which binds to a nuclear protein found in lung cells is contained in a portion of the proximal promoter region of the mouse surfactant protein B gene as defined by the region from base −18 to base −5 of the mouse surfactant protein B gene.

In another embodiment, the oligonucleotide includes at least one nucleic acid sequence which binds to thyroid transcription factor-1, or TTF-1 protein. TTF-1 protein is described further in Francis-Lang, et al., Mol. Cell. Biol., Vol. 12, No. 2, pgs. 576–588 (February 1992). The DNA sequence encoding human TTF-1 protein is described in Ikeda, et al., J. Biol. Chem., Vol. 270, No. 14, pgs. 8108–8114 (Apr. 7, 1995).

In a preferred embodiment, the at least one nucleic acid sequence which binds to TTF-1 protein includes a nucleic acid sequence, also known as a "core" nucleic acid sequence, which binds to TTF-1 protein, and which has the following structure:

WXNNYZ.

W is cytosine, guanine, or thymine. X is cytosine, thymine, or adenine. N is adenine, cytosine, guanine, or thymine. Y is adenine, thymine, or guanine. Z is guanine, adenine, or cytosine.

In one embodiment, W is cytosine. In another embodiment, X is thymine. In yet another embodiment, X is cytosine.

In yet another embodiment, Y is adenine, and in a further embodiment, Z is guanine. In another embodiment, Z is cytosine.

In a most preferred embodiment, the nucleic acid sequence has the following structure:

CTNNAG.

In another embodiment, the nucleic acid sequence which binds to TTF-1 protein may be one of the following:

CTGGAG (SEQ. ID NO.: 1);
CTTCAG (SEQ. ID NO.: 2);
CTCATA (SEQ. ID NO.: 3);
GCCAAG (SEQ. ID NO.: 4);
CTCAAG (SEQ. ID NO.: 5);
CTCCAG (SEQ. ID NO.: 6);
GTCAAG (SEQ. ID NO.: 7);
TCTAAG (SEQ. ID NO.: 8);
GTTAAG (SEQ. ID NO.: 9);
CTGAAG (SEQ. ID NO.: 10);
TCCAGG (SEQ. ID NO.: 11);
CCGAAC (SEQ. ID NO.: 12);
CCCAAG (SEQ. ID NO.: 13);
CATAAG; (SEQ. ID NO.: 14) or
TAGAGA (SEQ. ID NO.: 15).

Such "core" nucleic acid sequences, in general, are contained within larger nucleic acid sequences or oligonucleotides. Representative examples of nucleic acid sequences or oligonucleotides which include the above "core" sequences include the following:

(a) TCAAGCACCTGGAGGGCTCT (SEQ. ID NO.: 16);
(b) GGAGGGCTCTTCAGAGCAAA (SEQ. ID NO.: 17);
(c) AGGTGCCACTCATAGAAAGC (SEQ. ID NO.: 18);
(d) TTGTTTCTGCCAAGTGCTGG (SEQ. ID NO.: 19);
(e) GATGCCCACTCAAGCTTAGA (SEQ. ID NO.: 20);
(f) GGTGACCACTCCAGGACATG (SEQ. ID NO.: 21);
(g) ACTGATTACTCAAGTATTCT (SEQ. ID NO.: 22);
(h) GGAGCAGACTCAAGTAGAGG (SEQ. ID NO.: 23);
(i) ACTGCCCAGTCAAGTGTTCT; (SEQ. ID NO.: 24) and
(j) AGCACCTGGAGGGCTCTTCAGAGC (SEQ. ID NO.: 25).

Sequence (j), which the Applicants refer to as the SPB-f1 site, is contained in the proximal promoter region of the human lung surfactant protein B gene, and will be described further hereinbelow.

In yet another preferred embodiment, the at least one nucleic acid sequence which binds to TTF-1 protein includes the "core" nucleic acid sequence:

CAAG.

Representative examples of such nucleic acid sequences include, but are not limited to, those hereinabove described.

Although the scope of the present invention is not to be limited to any theoretical reasoning, Applicants have found that the above nucleic acid sequences, which may be found in the promoter region of the lung surfactant protein B gene, and include a "core" nucleic acid sequence which binds to TTF-1 protein (thyroid transcription factor 1 protein), activates expression of the lung surfactant protein gene by virtue of the binding of the "core", nucleic acid sequence to TTF-1 protein. Applicants also have discovered that such nucleic acid sequences also may be employed in order to direct expression of genes encoding proteins other than lung surfactant proteins in lung cells.

In another embodiment, the oligonucleotide further includes a sequence which binds to HNF-3 protein. Although HNF-3 protein is not found exclusively in lung tissue, Applicants have found that when a nucleic acid sequence which binds to HNF-3 protein is located in proximity to the nucleic acid sequence(s) which bind to TTF-1 protein, one obtains improved lung-specific expression of any nucleic acid sequences contained in vectors including the nucleic acid sequences which bind to TTF-1 protein and which bind to HNF-3 protein. HNF-3 protein is described further in Overdier, et al., *Mol. Cell. Biol.*, Vol. 14, No. 4 (April 1994).

In one embodiment, the nucleic acid sequence which binds to HNF-3 protein includes a nucleic acid sequence having the following structure:

BADTETTFEDTD (SEQ. ID NO.: 26), wherein B is adenine, cytosine, or guanine; D is adenine, thymine, or uracil; E is adenine or guanine; and F is guanine, thymine, or uracil. Preferably, the nucleic acid sequence which binds to HNF-3 protein includes a nucleic acid sequence having one of the following structures:

(a) CAGTGTTTGCCT; (SEQ. ID NO.: 27) or (b) GCAAAGACAAACACTGAGG (SEQ. ID NO.: 28).

Sequence (b), which the Applicants refer to as the SPB-f2 site, is found in the proximal promoter region of the human lung surfactant protein B gene, and will be described further hereinbelow.

In another embodiment, the oligonucleotide further includes a sequence which binds to HNF-5 protein.

As stated hereinabove, the oligonucleotides of the present invention, which contain the nucleic acid sequences(s) which bind(s) to nuclear proteins found in lung cells, may be employed in order to direct expression of genes encoding lung surfactant proteins, as well as other proteins, in lung cells. Thus, such oligonucleotides may be contained in an appropriate vector. Upon binding of the at least one nucleic acid sequence to the at least one nuclear protein found in lung cells, lung-specific expression of the vector is provided.

The term "vector" as used herein, means an agent containing or consisting of a DNA or RNA capable of introducing a nucleic acid sequence(s) into a cell, resulting in the expression of the nucleic acid sequence(s) in the cell.

Such vectors include, but are not limited to, eukaryotic or prokaryotic plasmids (such as, for example, bacterial plasmids), and viral vectors. The vector also may be contained within a liposome.

Such vectors, which include a nucleic acid sequence(s) which binds to TTF-1 protein, and which also may include a nucleic acid sequence which binds to HNF-3 protein, may also include at least one nucleic acid sequence encoding a therapeutic agent, whereby such vectors enable the expression of therapeutic agents in lung cells.

The term "therapeutic" is used in a generic sense and includes treating agents, prophylactic agents, and replacement agents.

In one embodiment, the vector is a viral vector. Viral vectors which may be employed include, but are not limited to, retroviral vectors, adenovirus vectors, adeno-associated virus vectors, and Herpes Virus vectors.

The adenoviral vector which is employed may, in one embodiment, be an adenoviral vector which includes essentially the complete adenoviral genome (Shenk, et al., *Curr. Top. Microbiol. Immunol.*, 111(3): 1–39 (1984)). Alternatively, the adenoviral vector may be a modified adenoviral vector in which at least a portion of the adenoviral genome has been deleted.

In one embodiment, the adenoviral vector comprises an adenoviral 5' ITR; an adenoviral 3' ITR; an adenoviral encapsidation signal; a DNA sequence which binds to TTF-1 protein, a DNA sequence which binds to HNF-3 protein, and at least one DNA sequence encoding a therapeutic agent. The vector is free of at least the majority of adenoviral E1 and E3 DNA sequences, but is not free of all of the E2 and E4 DNA sequences, and DNA sequences encoding adenoviral proteins promoted by the adenoviral major late promoter.

In still another embodiment, the gene in the E2a region that encodes the 72 kilodalton binding protein is mutated to produce a temperature sensitive protein that is active at 32° C., the temperature at which the viral particles are produced. This temperature sensitive mutant is described in Ensinger, et al., *J. Virology*, 10:328–339 (1972), Van der Vliet, et al., *J. Virology*, 15:348–354 (1975), and Friefeld, et al., *Virology*, 124:380–389 (1983).

In yet another embodiment, the vector is free of at least the majority of the E1 and E3 DNA sequences, is free of at least a portion of at least one DNA sequence selected from the group consisting of the E2 and E4 DNA sequences, and is free of DNA sequences encoding adenoviral proteins promoted by the adenoviral major late promoter.

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a multiple cloning site (which may be as hereinabove described); a poly A signal; and a DNA segment which corresponds to a segment of the adenoviral genome. The vector also may contain a tripartite leader sequence. The DNA segment corresponding to the adenoviral genome serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAVS6, shown in FIG. 19. The DNA including the DNA sequence which binds to the nuclear protein found in lung cells, such as TTF-1 protein, and may also include a DNA sequence which binds to HNF-3 protein or which binds to HNF-5 protein, and the DNA encoding therapeutic agent may be inserted into the multiple cloning site as a "cassette," or such elements may be inserted in separate cloning steps. One may amplify the expression of the DNA encoding the therapeutic agent by adding to the plasmid increased numbers of cassettes or of the DNA sequence which binds to the nuclear protein found in lung cells, such as TTF-1 protein.

This construct is then used to produce an adenoviral vector. Homologous recombination is effected with a modified or mutated adenovirus in which at least the majority of the E1 and E3 adenoviral DNA sequences have been deleted. Such homologous recombination may be effected through co-transfection of the plasmid vector and the modified adenovirus into a helper cell line, such as 293 cells, by $CaPO_4$ precipitation. Upon such homologous recombination, a recombinant adenoviral vector is formed that includes DNA sequences derived from the shuttle plasmid between the NotI site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 (ATCC VR-5) genome.

Through such homologous recombination, a vector is formed which includes an adenoviral 5' ITR, an adenoviral encapsidation signal; an E1a enhancer sequence; a promoter; at least one DNA sequence which binds to a nuclear protein found in lung cells, such as TTF-1 protein; and may also include at least one DNA sequence which binds HNF-3 protein or HNF-5 protein; at least the DNA sequence which encodes a therapeutic agent; a poly A signal; adenoviral DNA free of at least the majority of the E1 and E3 adenoviral DNA sequences; and an adenoviral 3' ITR. The vector also may include a tripartite leader sequence. This vector may then be transfected into a helper cell line, such as HeLa cells, or the 293 helper cell line (ATCC No. CRL1573), which will include the E1a and E1b DNA sequences, which are necessary for viral replication, and to generate infectious adenoviral particles. Transfection may take place by electroporation, calcium phosphate precipitation, microinjection, or through proteoliposomes, H441 cells (ATCC catalog no. HTB-174) may be employed to test for cell specificity.

The vector hereinabove described may include a multiple cloning site to facilitate the insertion of DNA sequence(s) into the cloning vector.

In general, the multiple cloning site includes "rare" restriction enzyme sites; i.e., sites which are found in eukaryotic genes at a frequency of from about one in every 10,000 to about one in every 100,000 base pairs. An appropriate vector in accordance with the present invention is thus formed by cutting the cloning vector by standard techniques at appropriate restriction sites in the multiple cloning site, and then ligating the DNA sequence encoding a therapeutic agent into the cloning vector.

The infectious viral particles then may be administered to a host, whereby the infectious viral particles will infect lung cells. The viral particles are administered in an amount effective to produce a therapeutic effect in a host. In one embodiment, the viral particles may be administered in an amount of from about $10^6$ to about $10^{12}$ plaque forming units (pfu), preferably from about $10^9$ to about $10^{11}$ pfu. The host may be a human or non-human animal host.

Preferably, the infectious viral vector particles are administered systemically, such as, for example, by intranasal or intratracheal administration. The viral vector particles also may be administered intravenously, intraperitoneally, or endotracheally, suspended in normal saline or phosphate buffered saline (pH 7.0).

The vector particles may be administered in combination with a pharmaceutically acceptable carrier suitable for administration to a patient. The carrier may be a liquid carrier (for example, a saline solution), or a solid carrier, such as, for example, microcarrier beads.

As an alternative to constructing an adenoviral vector particle, an adenoviral vector may be constructed as hereinabove described, and then encapsulated into liposomes, or complexed with lipids such as lipofectins or cytofectins. The adenoviral vector which is contained within a liposome or coupled to a lipid may be administered to a host as hereinabove described. The preparation of liposomes which contain the adenoviral vector, and the coupling of the adenoviral vector to a lipid are known to those skilled in the art. Examples of liposomes which may be employed include but are not limited to, those disclosed in U.S. Pat. No. 4,394,448, Nicolau, et al. *Proc. Nat. Acad. Sci.*, Vol. 80, pg. 1068 (1983), and Nabel, et al., *Proc. Nat. Acad. Sci.*, Vol. 90, pgs. 11307–11311 (December 1993). Examples of lipofectins which may be employed include any protein or polypeptide having a therapeutic effect. Such protection or polypeptides include, but are not limited to, those disclosed in Felgner, et al., *Proc. Nat. Acad. Sci.*, Vol. 8, pg. 7413 (1987). Examples of cytofectins which may be employed include, but are not limited to, those disclosed in U.S. Pat. No. 5,264,618.

Therapeutic agents which may be encoded by a DNA or RNA sequence(s) placed in the vector include, any protein or polypeptide having a therapeutic effect. Such proteins or polypeptides include, but are not limited to, those encoded by DNA or RNA sequences encoding lung surfactant proteins, such as SP-A, SP-B, SP-C, and SP-D for protection from lung injury; Clara Cell Secretory Protein (CCSP); the α-1-antitrypsin gene for treating lung fibrosis, cystic fibrosis, or emphysema; the cystic fibrosis transmembrane conductance regulator (CFTR); antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase, for treatment of acute lung injury, oxygen injury, or after chemical exposure to oxidants, infectious agents, shock, or for protection of the normal lung during chemotherapy for tumors (using bleomycin, adriamycin, or radiation); clotting factors, such as Factor VIII and Factor IX; and anti-tumor agents, such as, but not limited to, the Herpes Simplex thymidine kinase gene, wherein tumor killing is initiated by therapy with gancyclovir or acyclovir; GM-CSF (granulocyte-macrophage colony stimulating factor) which also may treat alveolar proteinosis, and cytokines such as TNF-α or Interleukin-1; and growth factors such as epidermal growth factor (EGF), and keratinocyte growth (KGF), for repair of or protection from injury after infection or oxygen therapy, bronchopulmonary dysplasia, or after therapy with lung oxidants such as antitumor agents, paraquot toxicity, or after exposure to toxins (e.g., alkylating agents, chemical warfare agents) or lung burns. In addition, the vector may include antisense DNA or RNA sequences.

Promoters which may control the genes encoding the therapeutic agents include may be promoters which include the nucleic acid sequence(s) which bind to the nuclear protein(s) bound in lung cells. Alternatively, the promoter may be a homologous or heterologous promoter. Such promoters include, but are not limited to, human globin promoters; viral thymidine kinase promoters, such as the Herpes Simplex thymidine kinase promoter; adenoviral late terminal repeats; retroviral LTRs; surfactant protein A, B, or C (SP-A, SP-B, or SP-C) promoters; the Clara Cell secretory protein (CCSP) promoter; the β-actin promoter; and human growth hormone promoters. The promoter also may be the native promoter which controls the gene encoding the therapeutic agent. In general, the promoter will include a TATA box, transcription start signal, and a CAAT box or variation thereof.

For example, one may construct a vector in accordance with the present invention which includes the CFTR gene. The vector then may be administered to the respiratory epithelium in an effective therapeutic amount for the correction of the pulmonary deficit in patients with cystic fibrosis. In another example, vectors containing functional proteins may be delivered to the respiratory epithelium in order to correct deficiencies in such proteins. Such functional proteins include antioxidants, α-1-antitrypsin, CFTR, lung surfactant proteins, cytokines, and growth factors such as EGF and KGF, and may also include adenosine deaminase for treatment of severe combined immune deficiency, von Willebrand's factor for treatment of Christmas disease, and β-glucuronidase for treatment of Gaucher's disease. Also, vectors including genes encoding anti-cancer agents or anti-inflammatory agents may be administered to lung cells of a patient for the treatment of lung cancer or inflammatory lung disease.

In another embodiment, the viral vector is a retroviral vector.

Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, gibbon ape leukemia virus, human immunodeficiency virus, myeloproliferative sarcoma virus, and mammary tumor virus. Preferably, the retroviral vector is an infectious but non-replication competent retrovirus; however, replication competent retroviruses may also be used.

Retroviral vectors are useful as agents to mediate retroviral-mediated gene transfer into eukaryotic cells. Retroviral vectors generally are constructed such that the majority of sequences coding for the structural genes of the virus are deleted and replaced by the gene(s) of interest. Most often, the structural genes (i.e., gag, pol, and env), are removed from the retroviral backbone using genetic engineering techniques known in the art. This may include digestion with the appropriate restriction endonuclease or, in some instances, with Bal 31 exonuclease to generate fragments containing appropriate portions of the packaging signal.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

In one embodiment, the retroviral vector may be one of a series of vectors described in Bender, et al., *J. Virol.* 61:1639–1649 (1987), based on the N2 vector (Armentano, et al., *J. Virol.*, 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point. In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller, et al., *Biotechniques*, 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

In one embodiment, the retroviral vector may be a Moloney Murine Leukemia Virus of the LN series of vectors, such as those hereinabove mentioned, and described further in Bender, et al. (1987) and Miller, et al. (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites. Such vectors are further described in U.S. Pat. No. 5,672,510 and incorporated herein by reference in its entirety.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein. These promoters may be altered, by deletion mutation(s), to provide a basic transcription unit that can be modified by the addition of the TTF-1 binding cis-acting sequence.

The vector then is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, such as hereinabove described, and $CaPO_4$ precipitation. In one alternative, the retroviral plasmid vector may be encapsulated into a liposome, or coupled to a lipid, as hereinabove described, and then administered to a host, also as hereinabove described.

The producer cell line generates infectious but non-replicating viral vector particles which include the nucleic acid sequence(s) which bind(s) to a nuclear protein found in lung cells, such as to TTF-1 protein, and may also include nucleic acid sequence(s) which bind(s) to HNF-3 protein or HNF-5 protein, and the nucleic acid sequence(s) encoding a therapeutic agent. Such vector particles then may be employed to transduce lung cells, which will express the nucleic acid sequence(s) encoding the therapeutic agent(s). The vector particles may transduce the lung cells at a multiplicity of infection of from 0.1 to 100 vectors per cell, preferably from 1 to 10 vectors per cell, and more preferably at about 10 vectors per cell.

Therapeutic agents which may be encoded by at least one nucleic acid sequence contained in the viral vector particles may be those as hereinabove described. The vector also may include an antisense DNA or RNA sequence. Promoters controlling such nucleic acid sequences also may be those hereinabove described.

In a preferred embodiment, DNA binding sites for thyroid transcription factor 1 (TTF-1) alone or in combination with hepatocyte nuclear factor 3 (HNF-3) are used to direct lung specific transcription of a therapeutic gene or cDNA. This may be accomplished by using TTF-1 and HNF-3 DNA binding sites in some combination with a minimal homologous or heterologous promoter. This transcription unit could be linked to a therapeutic cDNA or gene, introduced into a plasmid or viral DNA (adenoviral, retroviral, adeno-associated or other viral vector) vector, and delivered systemically or locally to achieve lung-specific transcription of the linked therapeutic cDNA or gene. The use of TTF-1 and HNF-3 binding sites in the transcription unit of DNA-based gene delivery vectors allows a specific therapeutic gene product to be expressed only in lung epithelial cells that contain TTF-1 and HNF-3 regulatory factors even when the vector was delivered systemically, since the TTF-1 component of the vector will support gene transcription in a highly lung selective manner. This vector could be delivered systemically, or via the trachea, without the complication of ectopic expression outside of the lung. In addition, more precise regulation of the therapeutic gene could be achieved by use of known lung-specific genetic elements such as from the SP-B gene. This could involve delivery of the cystic fibrosis transmembrane conductance regulator (CFTR) to the respiratory epithelium for correction of the pulmonary deficit in patients with cystic fibrosis, or replacement of functional proteins in the respiratory epithelium or local lung-specific production of a toxic drug for treatment of lung cancer or inflammatory lung disease. Protein (gene products) be directed for secretion into the airway or the systemic circulation. For example, α-1-antitrypsin cytokines (GM-CSF), intracellular proteins (antioxidant genes), CFTR or circulating proteins (clotting factors) could be expressed in lung epithelial cells with the lung selective DNA binding sites for therapy of common pulmonary and non-pulmonary diseases.

The nucleic acid sequences of the present invention also may be used as probes to detect cancer which has originated in the lung or thyroid. The probes are prepared by techniques known to those skilled in the art. Because TTF-1 protein and HNF-3 protein are found in cells of cancers which originate in the lung or thyroid, one may obtain a sample of cancer cells from a patient and contact such cells with a nucleic acid sequence which includes at least one nucleic acid sequence which binds to TTF-1 protein (and preferably also includes at least one nucleic acid sequence which binds to HNF-3 protein). Binding of the nucleic acid sequence to the cancer cells then is determined by standard techniques. If the nucleic acid sequence binds to the cancer cells, then one would know that the cancer originated in the lung or thyroid. Once one determines whether the cancer originated in the lung or thyroid, an appropriate course of treatment of the cancer then may be undertaken.

In addition, the nucleic acid sequence which binds to TTF-1 protein (and preferably also binds to HNF-3 protein) may be placed into a vector which also includes a negative selective marker, such as, for example, the Herpes Simplex thymidine kinase gene. In one embodiment, the vector is a retroviral vector. Such a retroviral vector then may be administered to a patient suffering from cancer which has originated in the lung. Upon administration of the vector, the vector infects the cancer cells. After infection of the cancer cells with the vector, an interaction agent is administered to the patient. The interaction agent, such as, for example, ganciclovir, interacts with the Herpes Simplex thymidine kinase expressed in the cancer cells, whereby such cancer cells are killed.

In accordance with another aspect of the present invention, there is provided a method of detecting cancer which has originated in the lung. The method comprises obtaining a sample of cancer cells from a patient, and contacting the cancer cells with at least one antibody which recognizes an epitope of a protein selected from the group consisting of nuclear proteins found in lung cells and lung surfactant proteins. Binding of the at least one antibody to the cancer cells then is determined. The antibody may be a polyclonal or monoclonal antibody.

In one embodiment, the at least one antibody recognizes an epitope of a nuclear protein found in lung cells.

Nuclear proteins to which the at least one antibody may bind include, but are not limited to, TTF-1 protein.

In another embodiment, the at least one antibody recognizes an epitope of a lung surfactant protein. Lung surfactant proteins to which the at least one antibody may bind include, but are not limited to, surfactant protein A (SP-A) and surfactant protein B (SP-B).

Cancers originating in the lung which may be detected include, but are not limited to, lung adenocarcinomas, squamous cell lung carcinomas, and small cell lung carcinomas.

In accordance with yet another aspect of the present invention, there is provided an isolated polynucleotide comprising a member selected from the group consisting of: (a) a polynucleotide encoding human TTF-1 protein; (b) a polynucleotide which is substantially homologous to the polynucleotide of (a); (c) a polynucleotide encoding a protein that is substantially homologous to human TTF-1 protein; (d) a polynucleotide capable of hybridizing to any one of polynucleotides (a), (b), or (c); and (e) a polynucleotide fragment of any one of polynucleotides (a), (b), (c), or (d).

"Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

In one embodiment, the polynucleotide comprises nucleotides 199 to 569 and 1,533 to 2,372 of the polynucleotide sequence shown in FIG. 39. In another embodiment, the polynucleotide comprises nucleotides 199 to 2,372 of the polynucleotide sequence shown in FIG. 39. In yet another embodiment, the polynucleotide comprises nucleotides 1 to 2,372 of the polynucleotide sequence shown in FIG. 39. In a further embodiment, the polynucleotide comprises nucleotides −132 to 3,151 of the sequence shown in FIG. 39.

The polynucleotides may be employed in the diagnosis of cancers which originated in the lung or thyroid. For example, polynucleotide fragments of the human TTF-1 protein gene may be produced by PCR. Such polynucleotide fragments may be used as diagnostic probes which are employed for detecting TTF-1 nucleic acid sequences, such as TTF-1 mRNA, in cancer cells. Such detection may be carried out, for example, by contacting fixed cancer cells with the polynucleotide probe via in situ hybridization, or by isolating the nucleic acids from the cancer cells, and contacting such isolated nucleic acids with the polynucleotide probe. If the polynucleotide probe binds to nucleic acid sequence(s) of the cancer cells, then such cancer has originated in the lung or thyroid, and appropriate treatment procedures may be recommended.

The polynucleotide encoding the human TTF-1 protein also may be placed in an appropriate expression vector, which is employed in the transduction of cells in vitro, thereby providing for the production in vitro of TTF-1 protein. Such TTF-1 protein may be used to generate antibodies against TTF-1 protein, whereby such antibodies also may be employed as hereinabove described for the detection of cancer which originated in the lung or thyroid.

In addition, the promoter region of the polynucleotide encoding human TTF-1 protein may be placed in an appropriate expression vector in order to direct expression of genes encoding lung surfactant proteins, as well as other proteins, in lung cells. Such vectors include those hereinabove described.

BRIEF DESCRIPTION OF THE DRAWINGS

The invention now will be described with respect to the drawings, wherein:

FIGS. 1A and 1B are autoradiograms of cell type-specific DNase I hypersensitivity in the SPB gene and promoter region with respect to H441 and RAJI cells;

FIG. 1C is a map of DNase I hypersensitivity sites in the human SPB gene;

FIG. 6 is a schematic of a nucleotide sequence (SEQ ID NO: 49) and a summary of nuclear protein-binding sites in the SPB promoter region;

FIG. 7A depicts conserved regions of the mouse (SEQ ID NO: 50) and human SP-B promoters, as well as the sequences SPB-f1 and SPB-f2 which contain TNF-1 and HNF-3 binding sites, respectively;

Figures 8A, 8B:
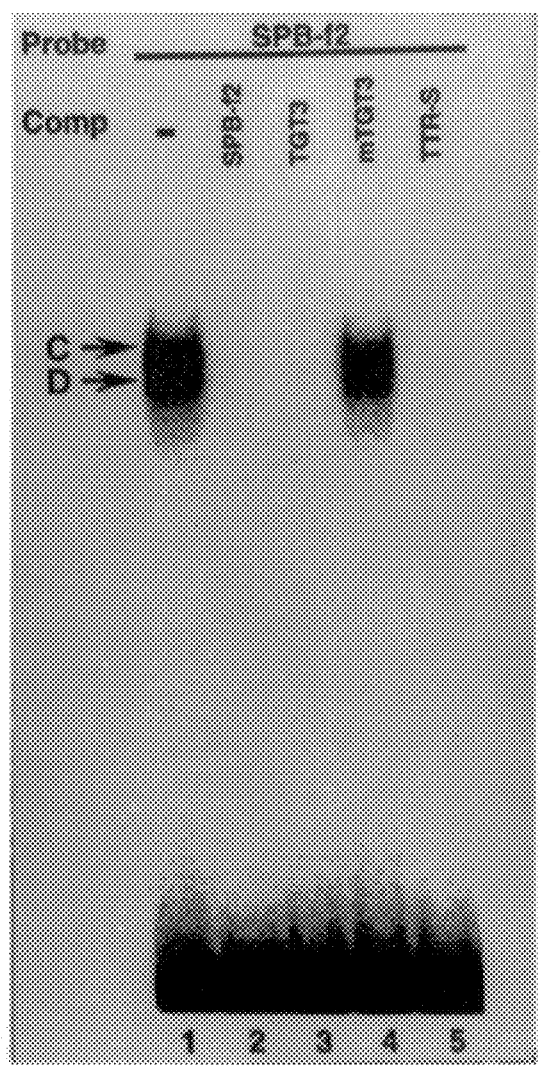
Figure 8C:
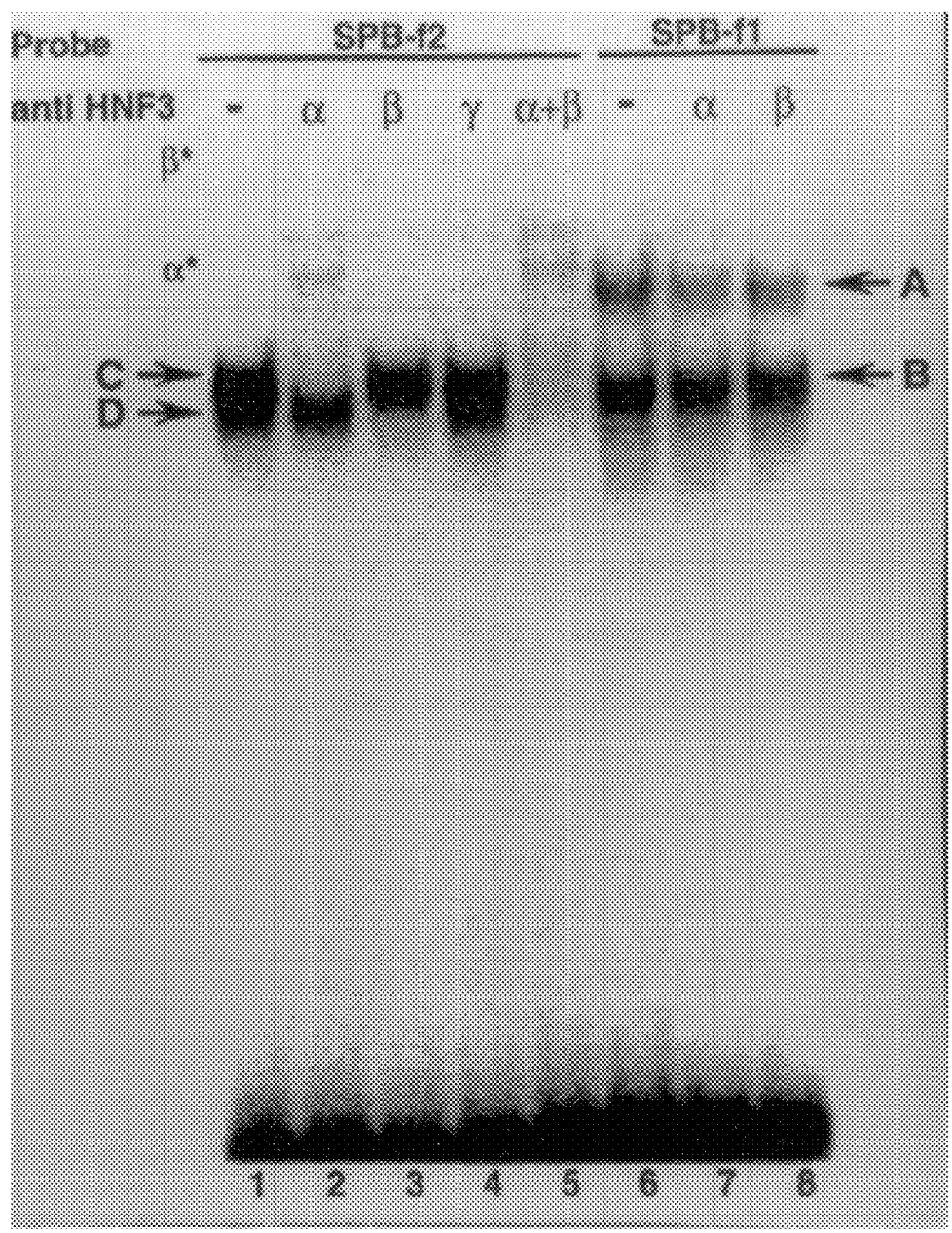
Figures 9A, 9B:
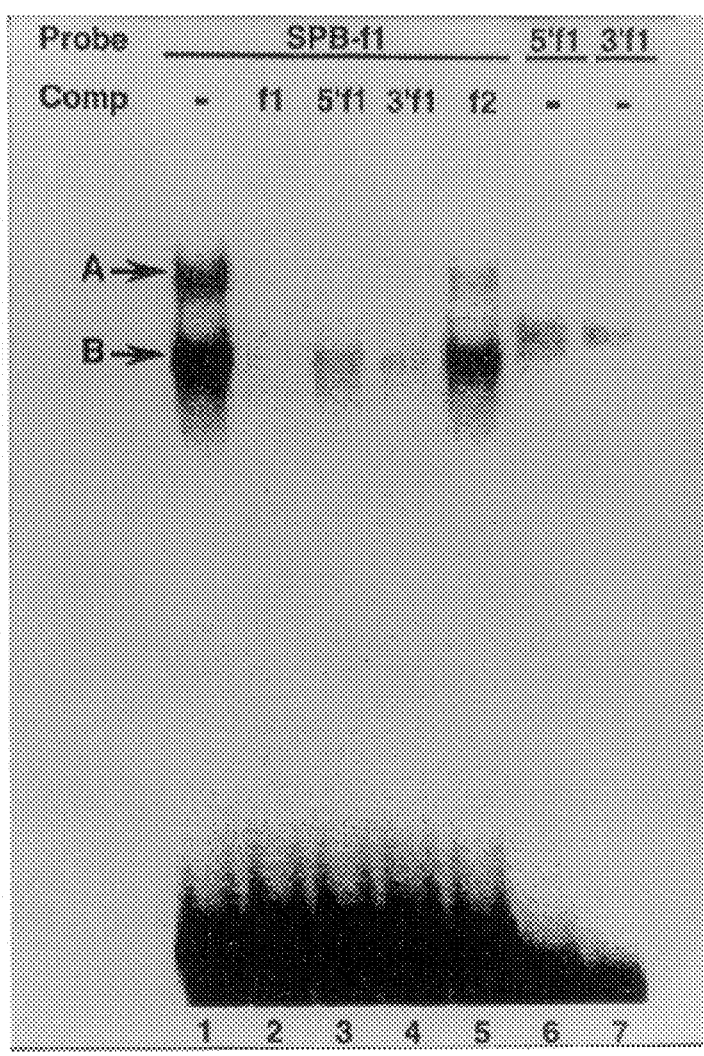
Figure 10A:
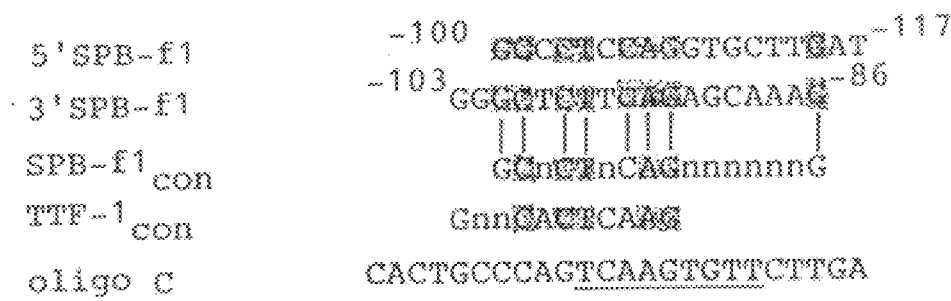

the FIG. 8A depicts a comparison of the SPB-f2 (SEQ ID NO: 53) probe with the TGT3 (SEQ ID NO: 52) and TTR-S (SEQ ID NO: 54) HNF-3 binding sites;

FIG. 8B is a blot of an EMSA assay in which unlabeled competitors SPB-f2, TGT3, mTGT3, and TTR-S were added at a 1,000-fold molar excess as compared to probe;

FIG. 8C is a blot of an EMSA assay in which antisera to each HNF-3 protein, with MLE-15 nuclear extracts;

FIG. 9A depicts 5' (5'f1) (SEQ ID NO: 56) and 3' (3'f1) (SEQ ID NO: 57) sub-fragments of the SPB-f1 (SEQ ID NO: 55) probe;

FIG. 9B is a blot of an EMSA assay in which unlabeled competitors f1, 5'f1, 3'f1, and f2 were added to an SPB-f1 probe;

FIG. 10A depicts a comparison of the oligonucleotide sequences of 5'SPB-f1, (SEQ ID NO: 58) 3'SPB-f1, (SEQ ID NO: 59) SPB-f1 con, (SEQ ID NO: 60) TTF-1 con, (SEQ ID NO: 61) and oligo C; (SEQ ID NO: 62)

Figure 10B:
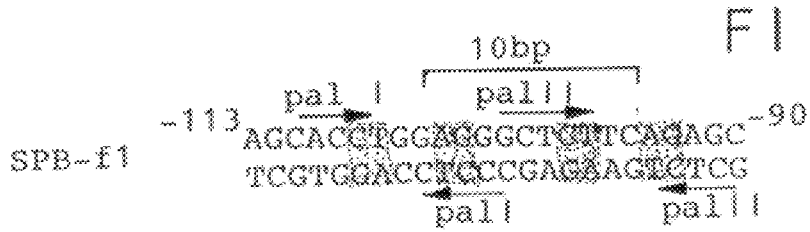

FIG. 10B depicts the organization of CTNNAG motifs within SPB-f1; (SEQ ID NO: 55)

Figure 10C:
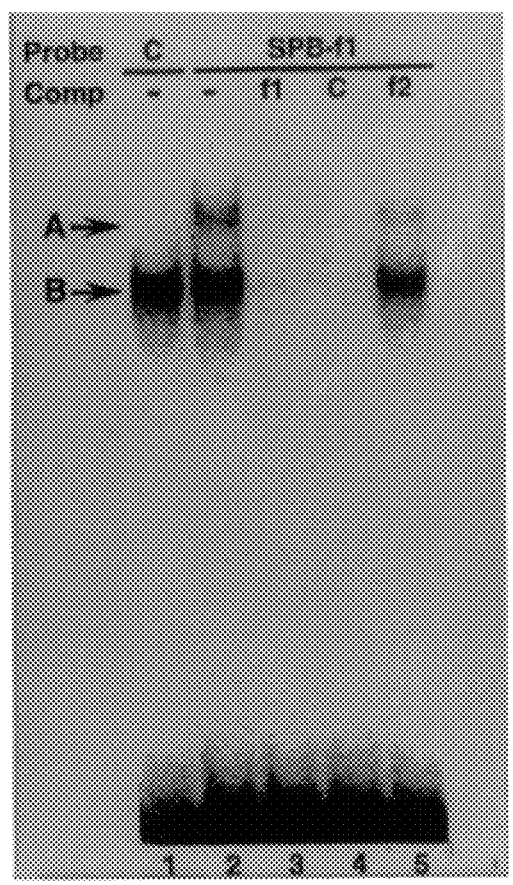
Figure 10D:
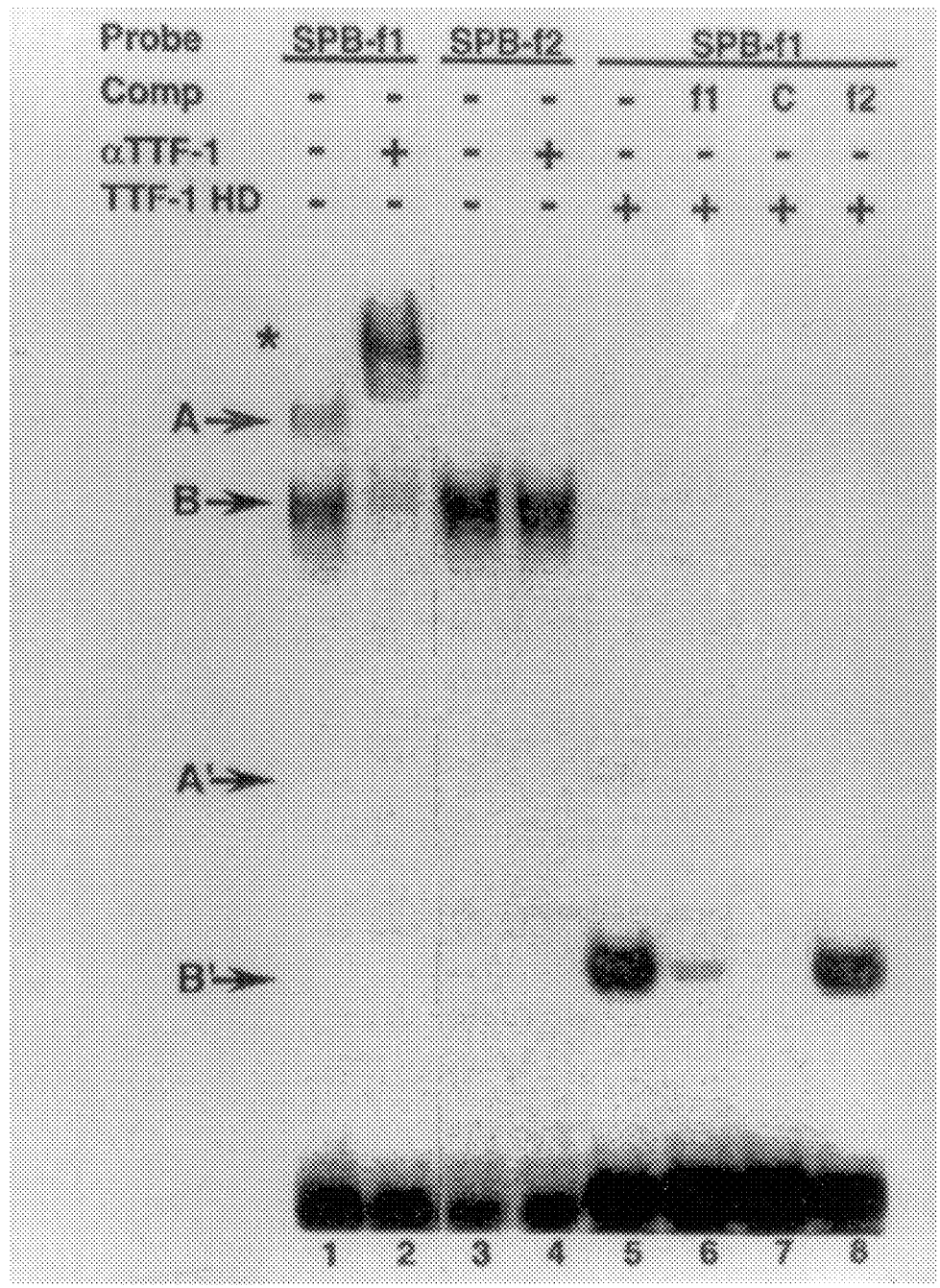
Figure 13:
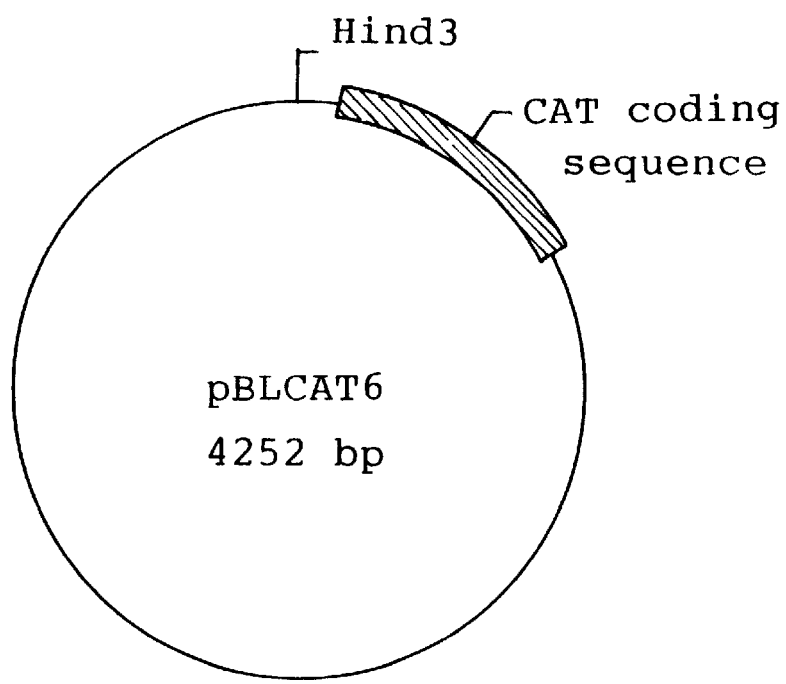
Figure 14:
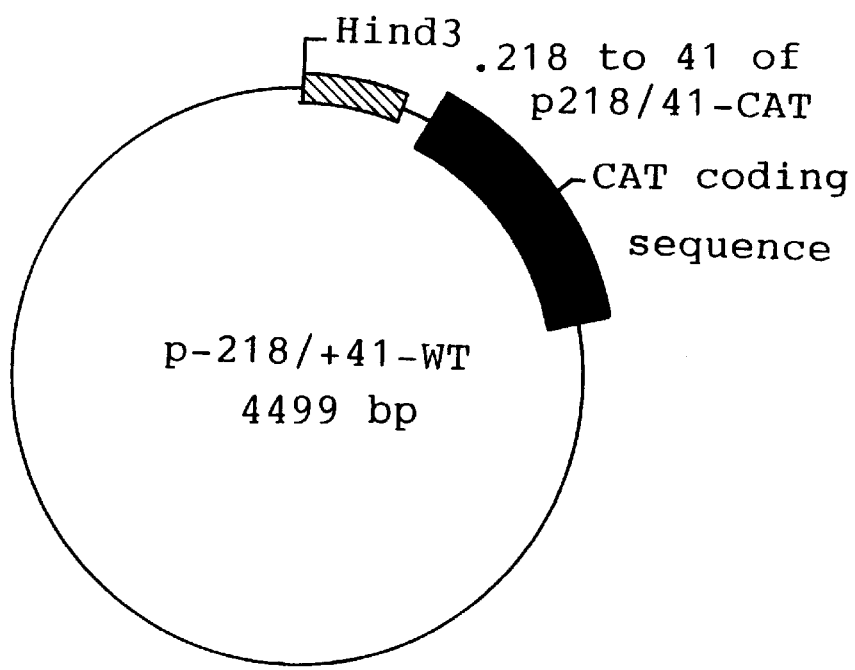
Figure 15A:
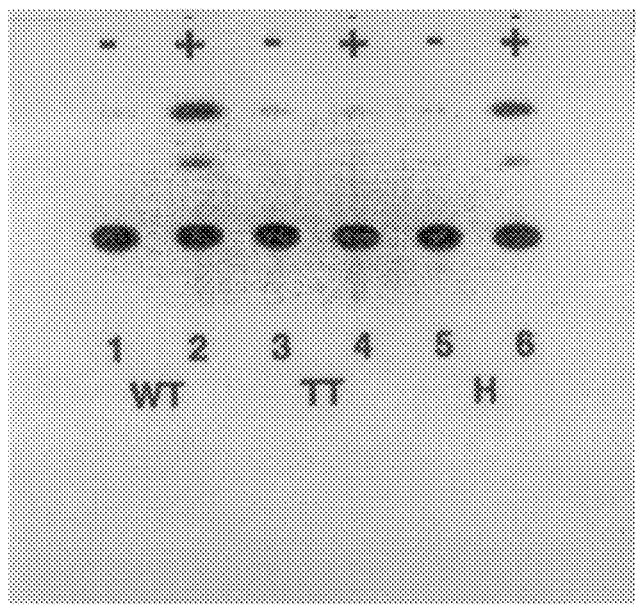
Figure 15B:
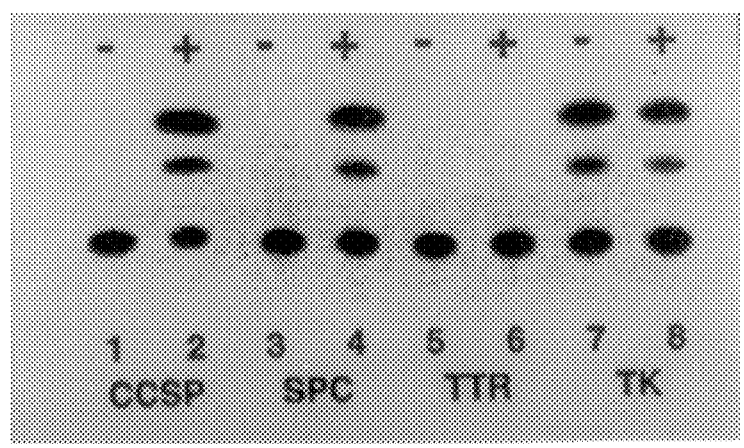
Figure 16:
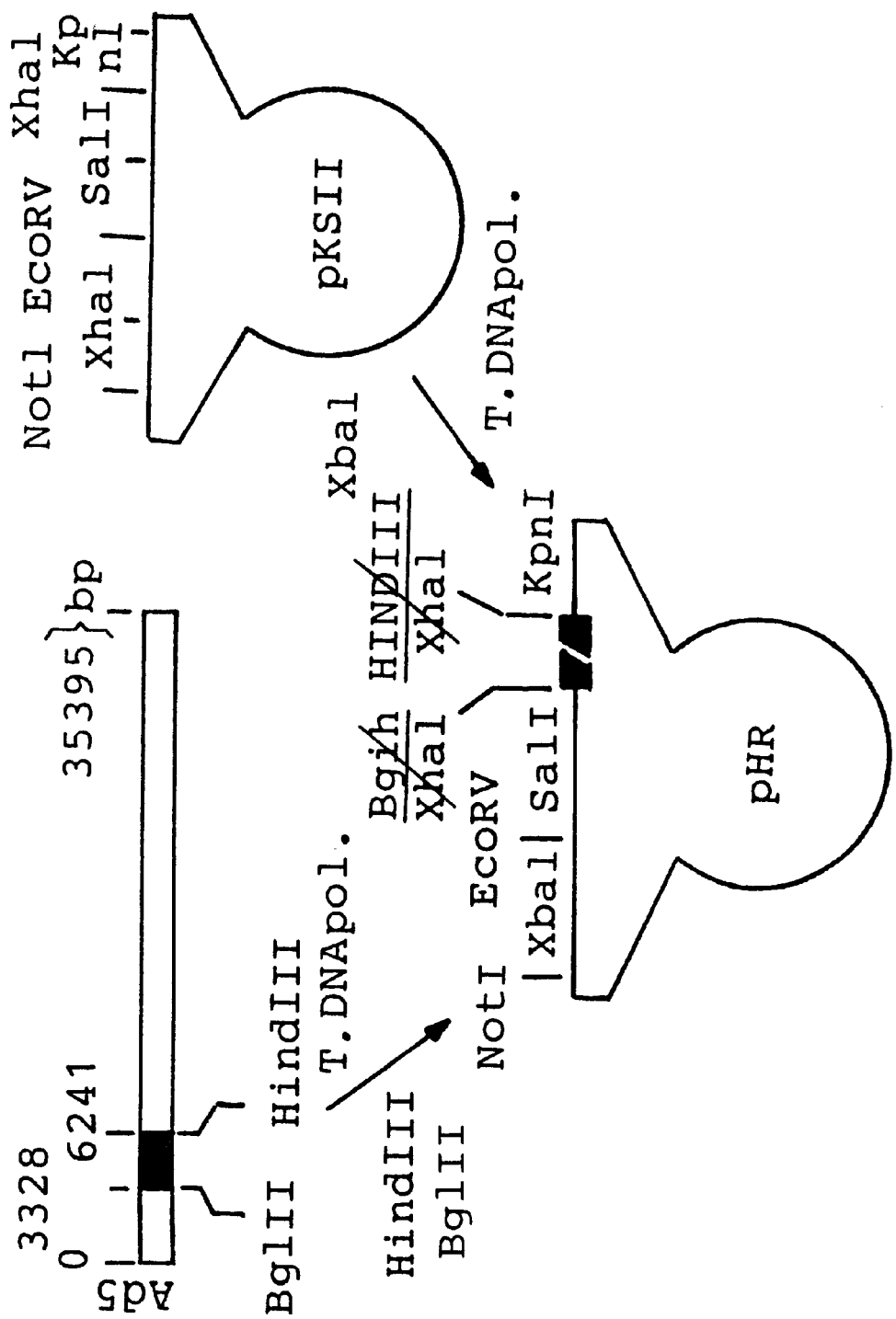
Figure 17:
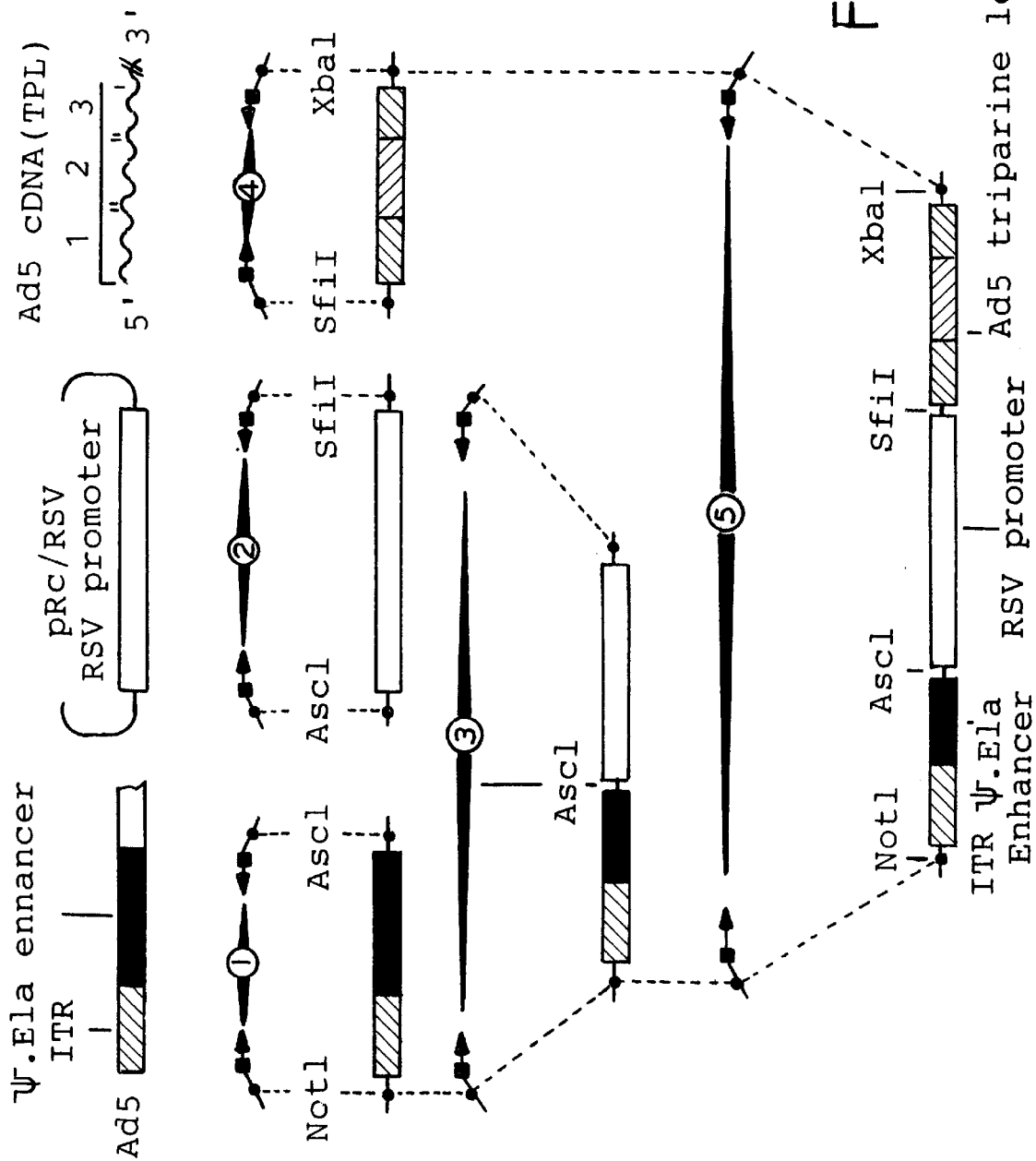
Figure 18:
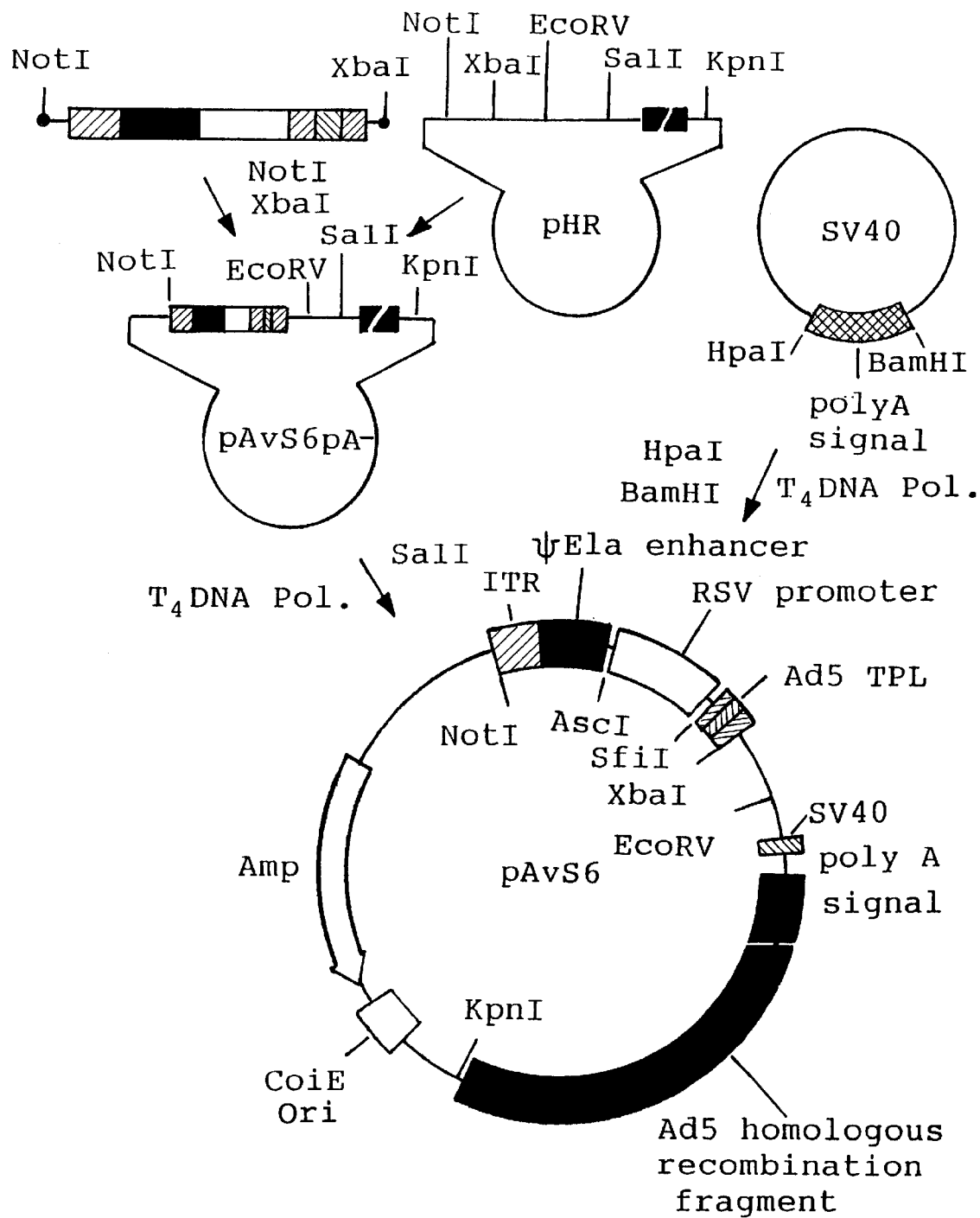
Figure 19:
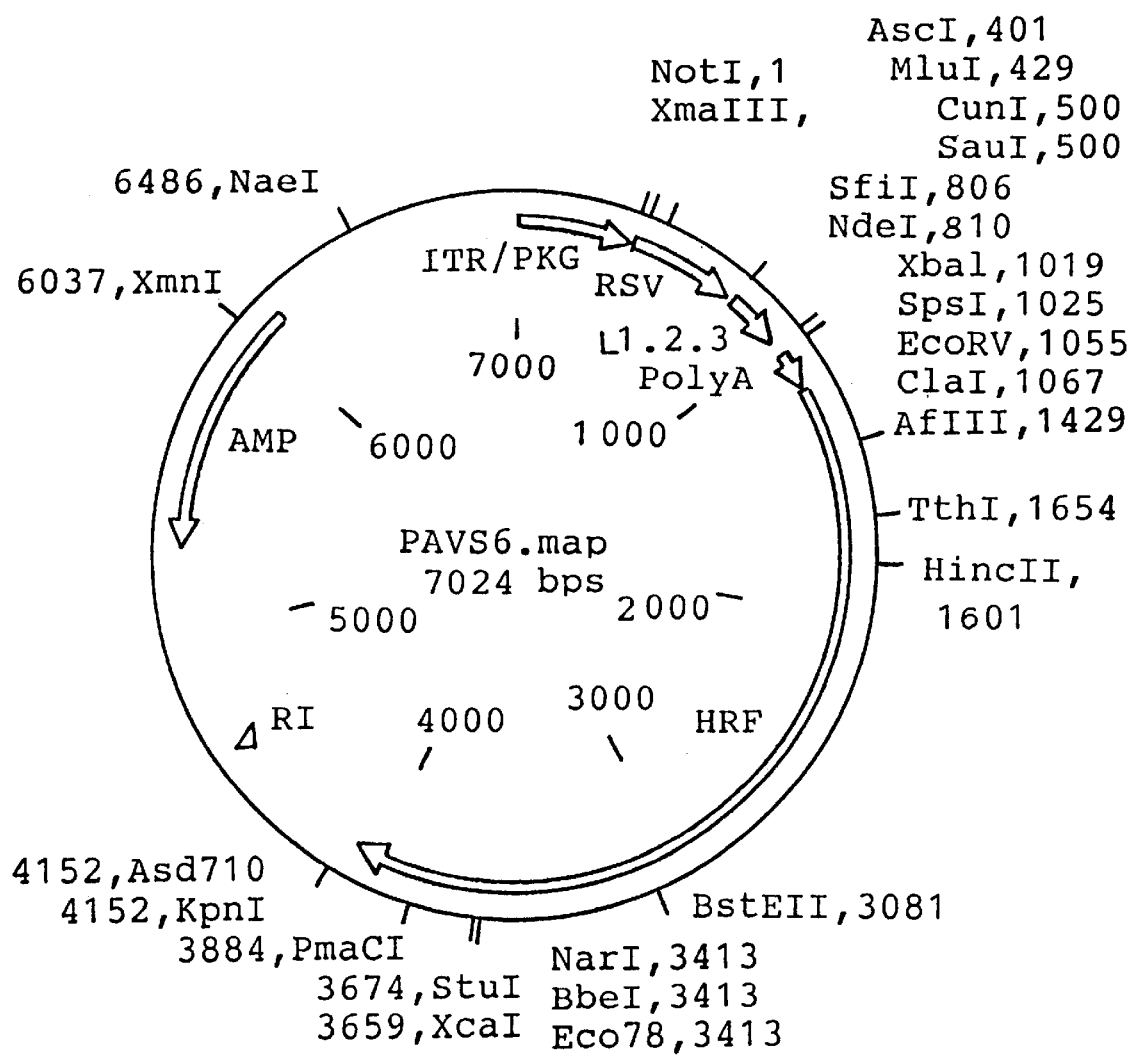
Figure 20:
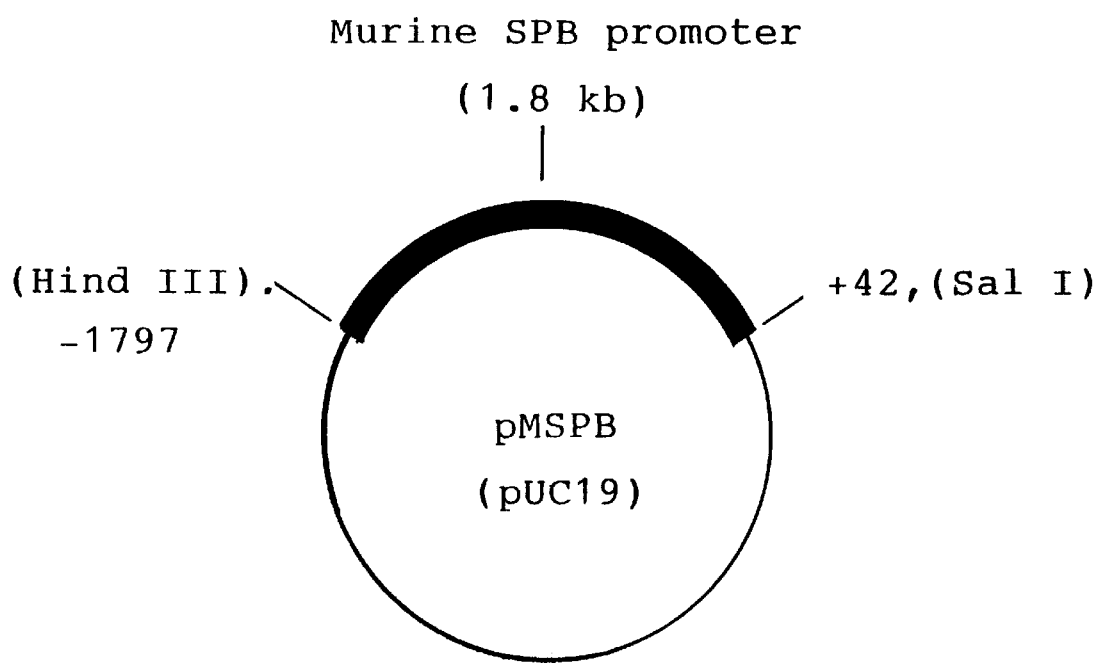
Figure 21:
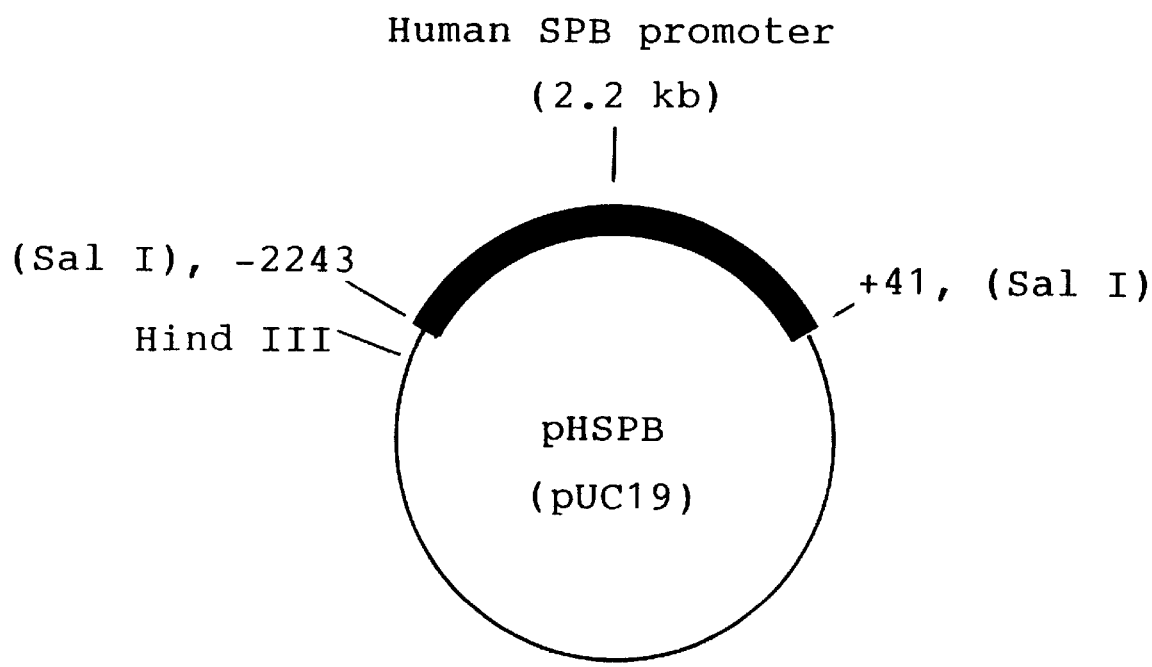
Figure 22:
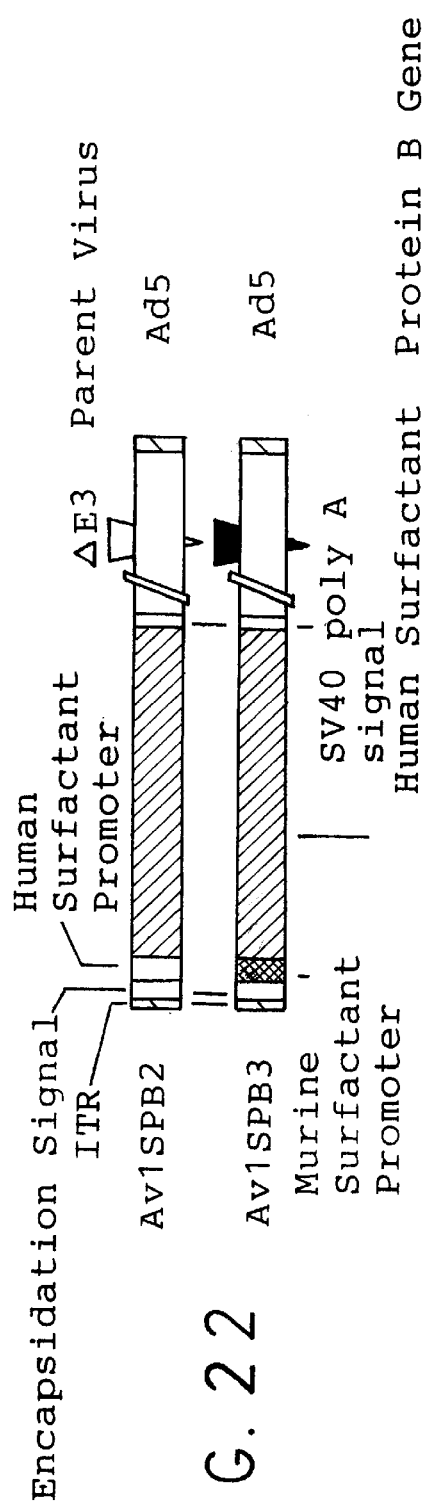
Figure 23:
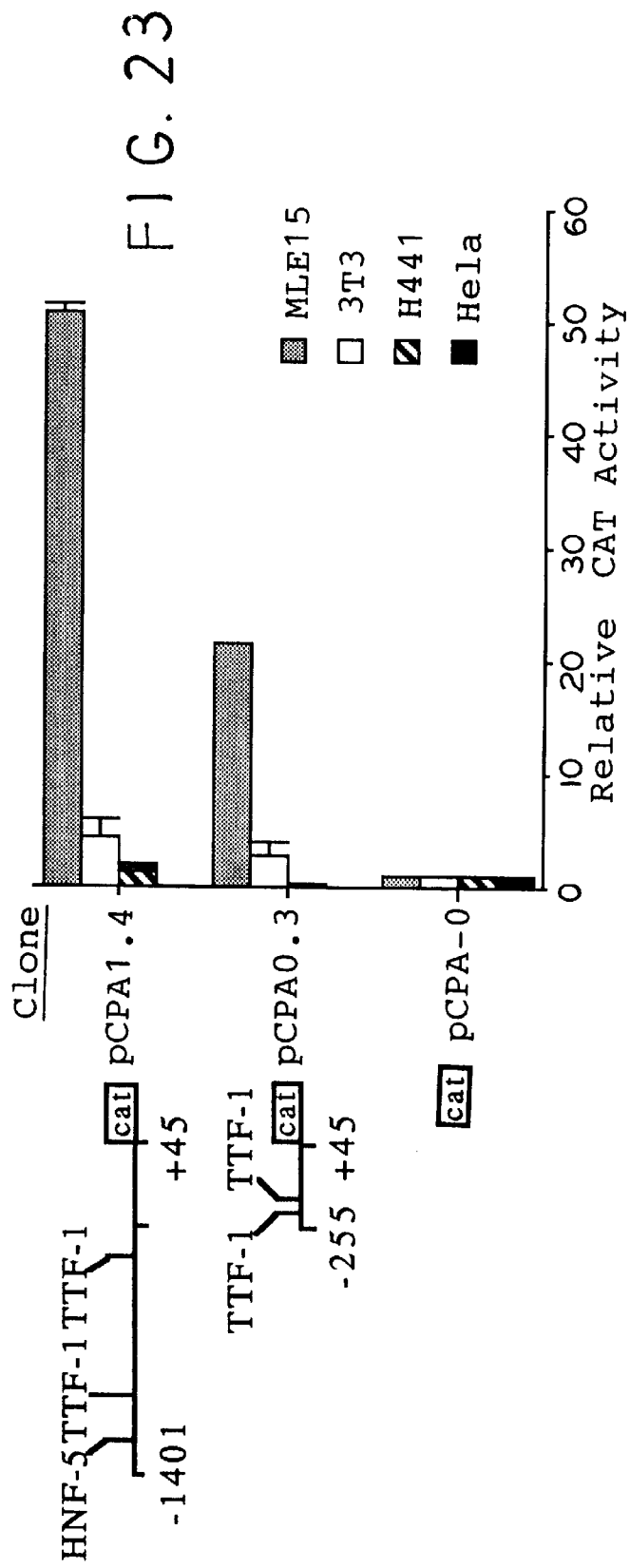
Figure 24:
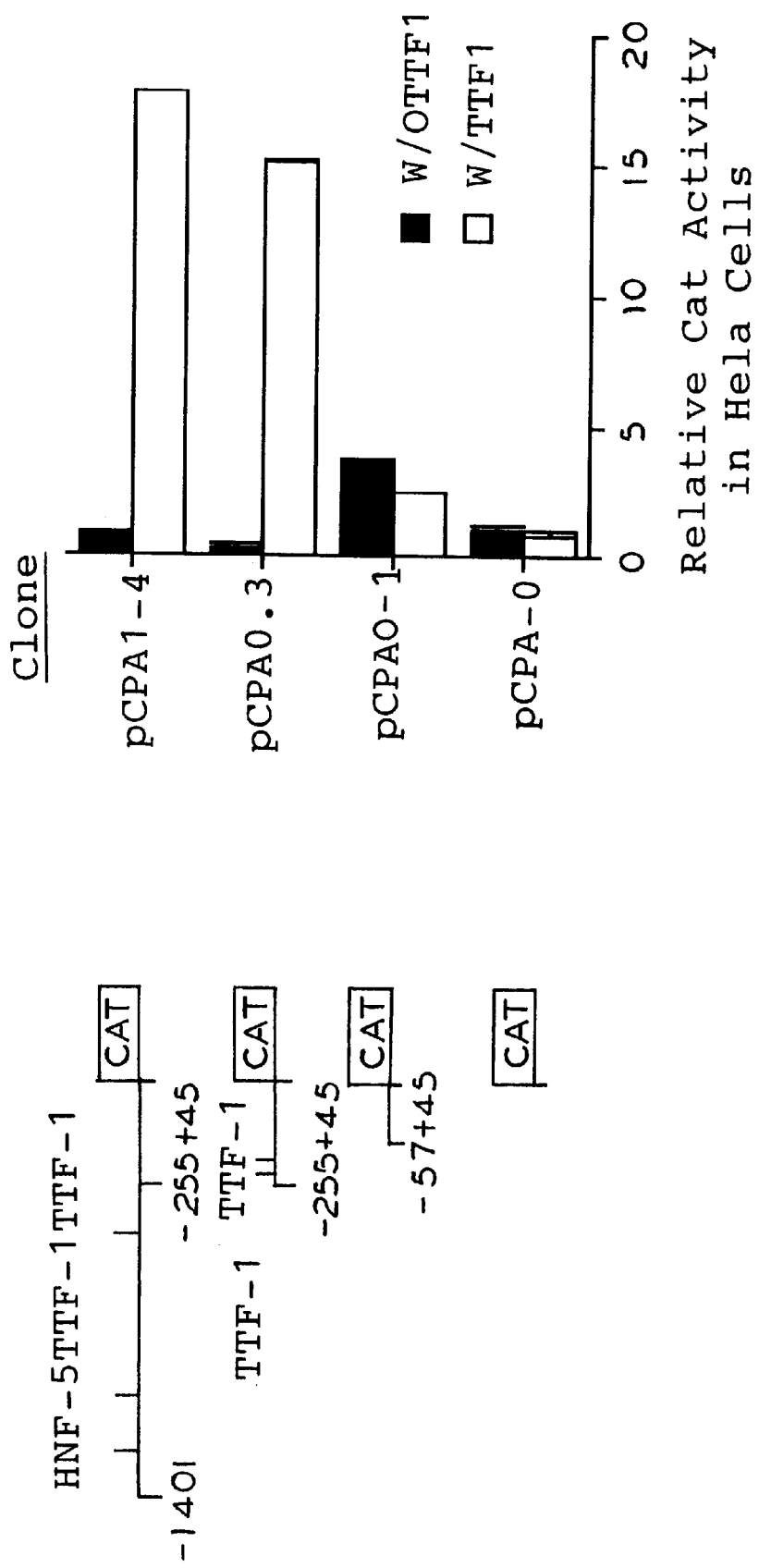
Figures 25, 29A:
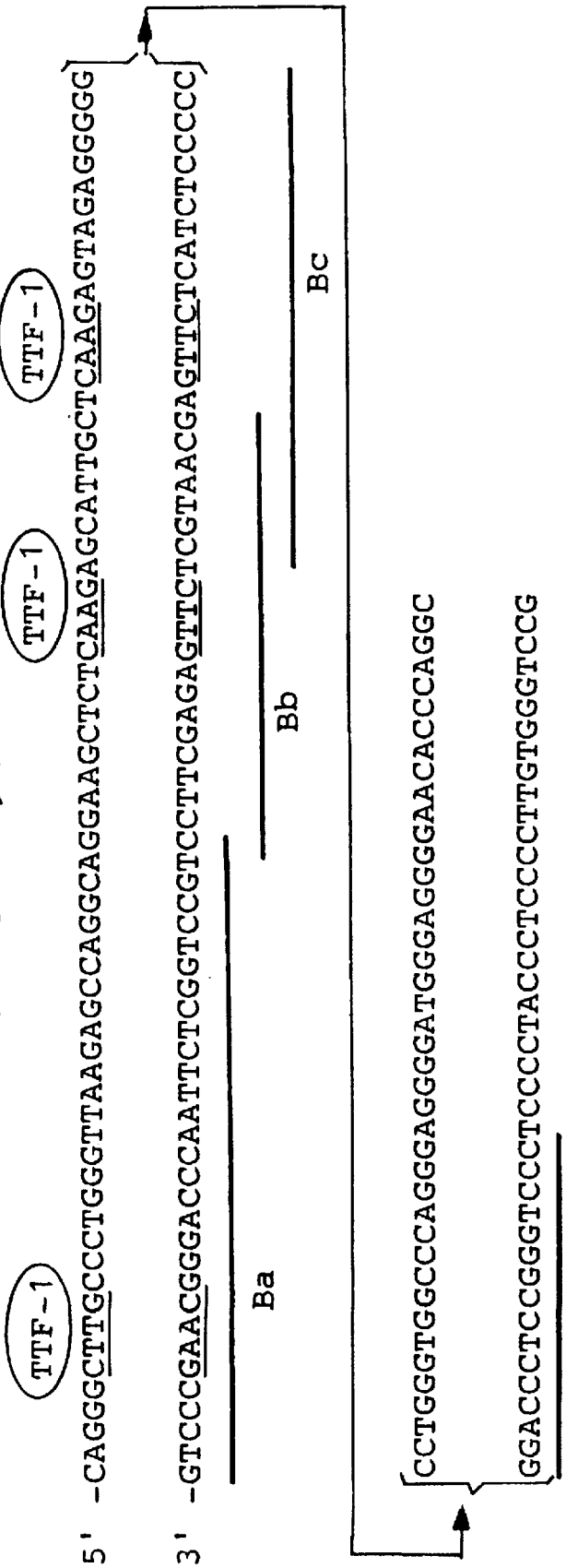
Figure 26:
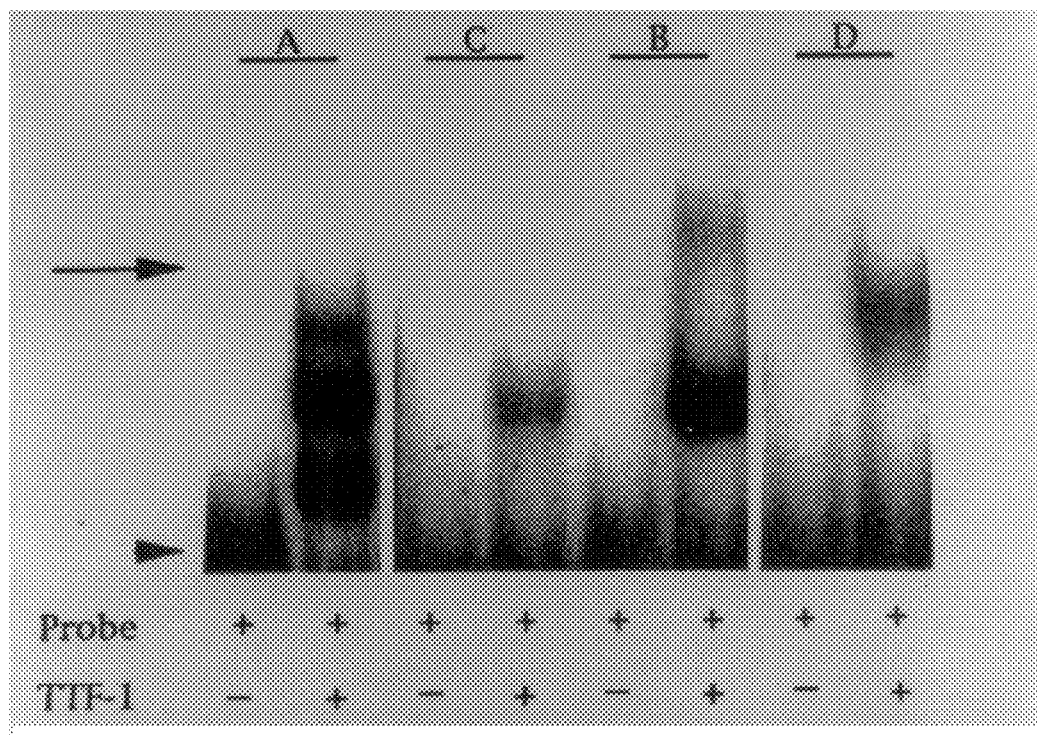
Figure 28C:
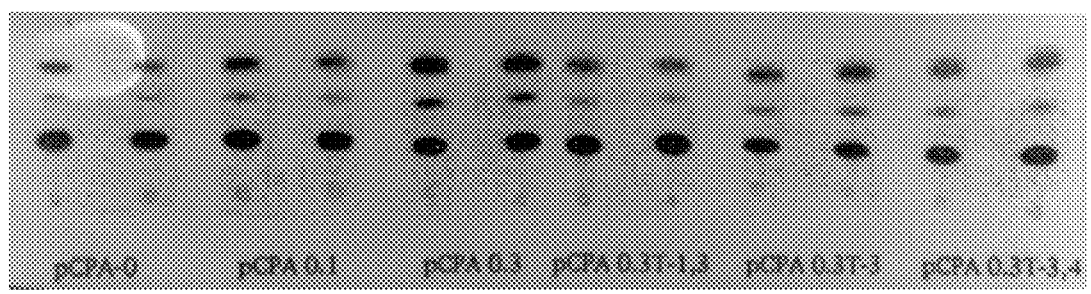
Figure 28D:
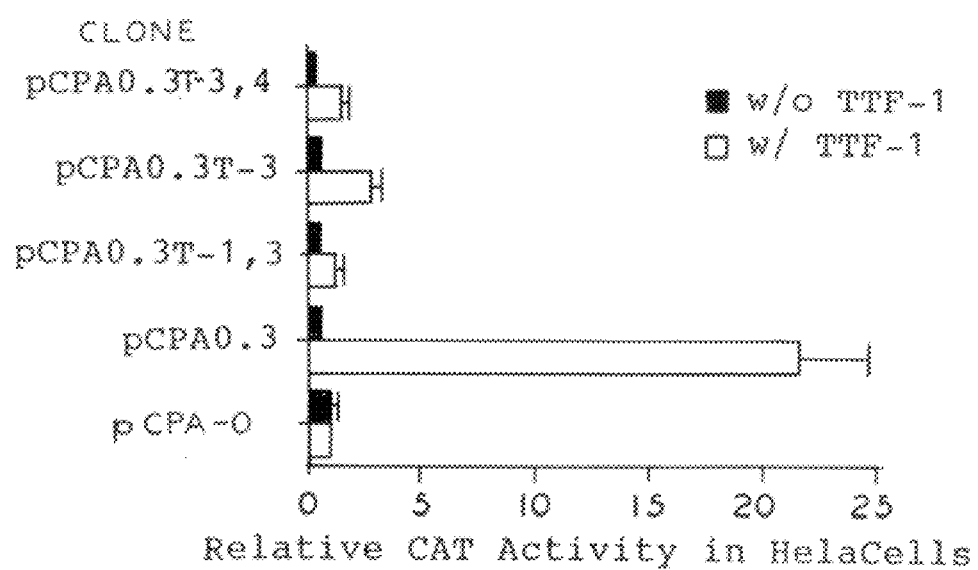
Figure 28E:
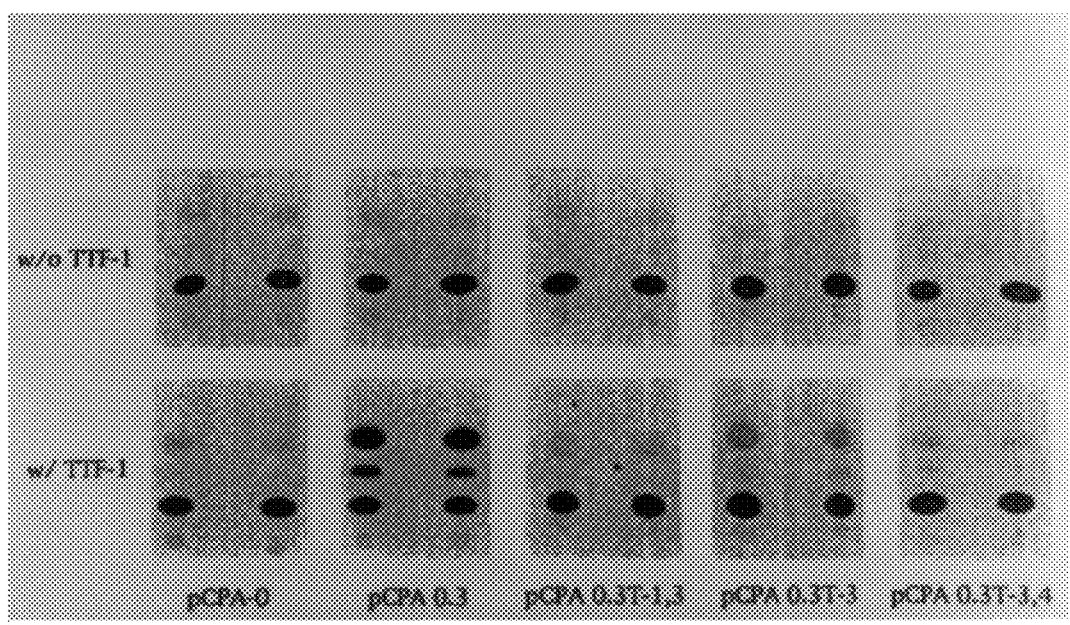
Figure 29B:
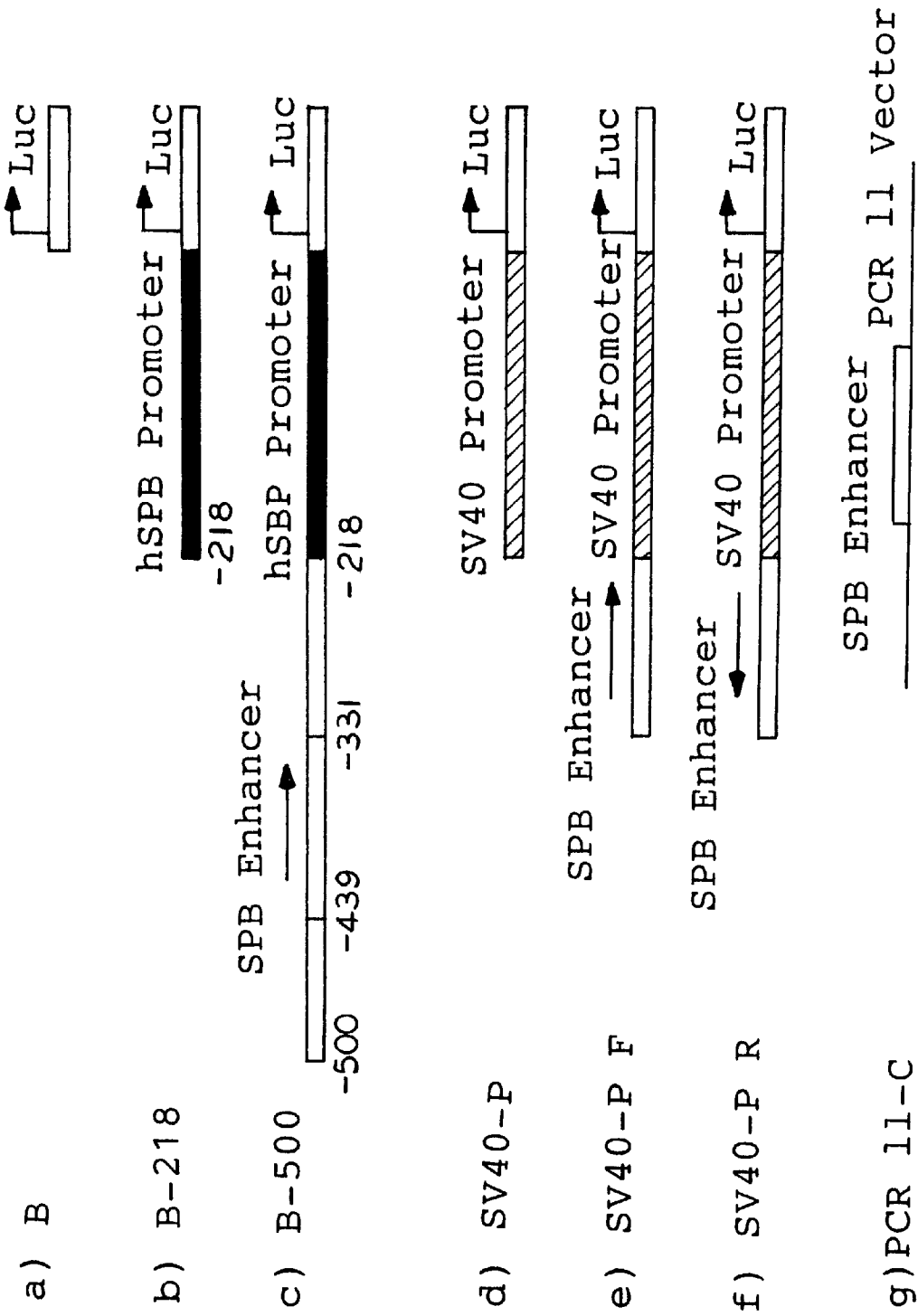
Figure 31A:
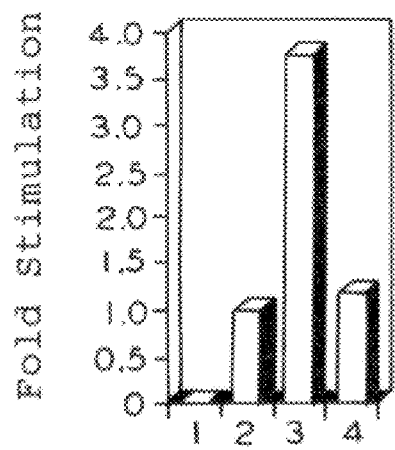
Figure 30:
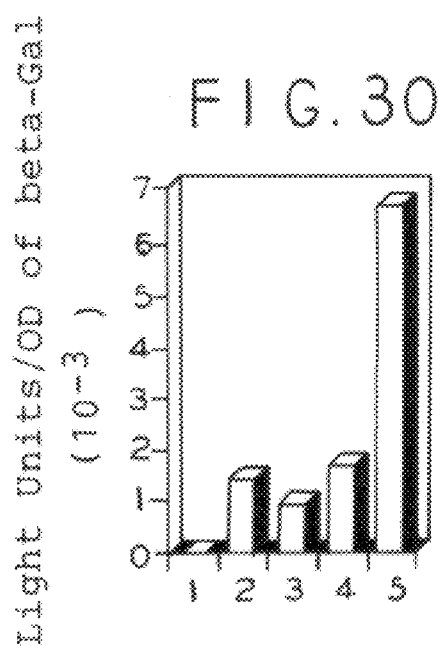
Figure 31B:
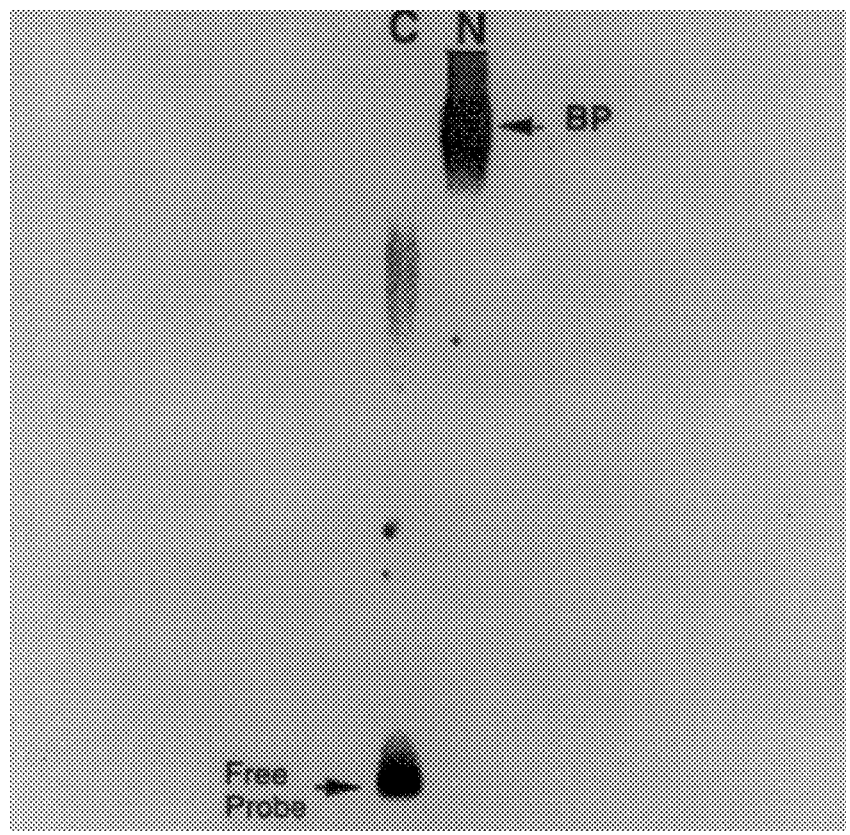
Figure 32A:
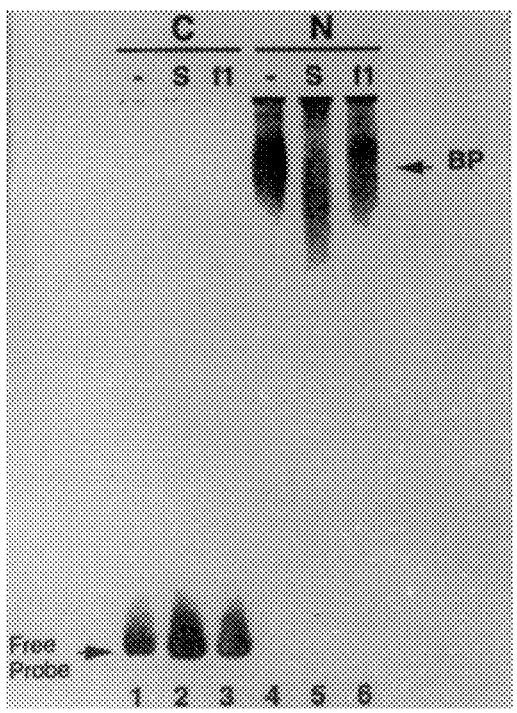
Figure 32B:
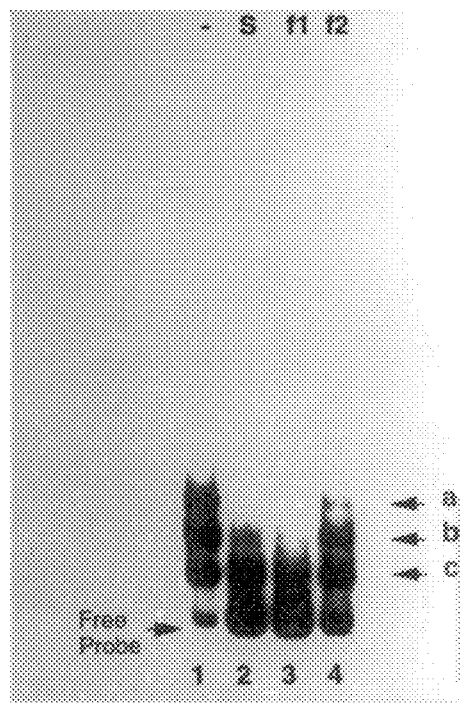
Figure 33A:
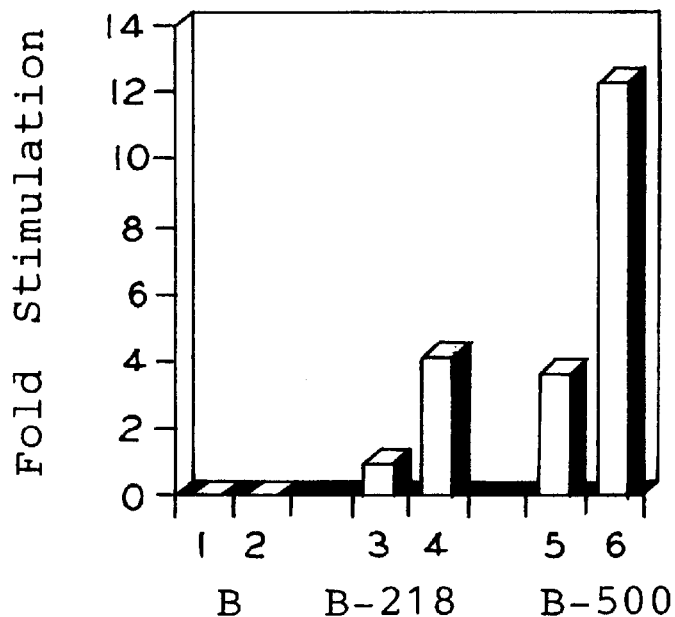
Figure 33B:
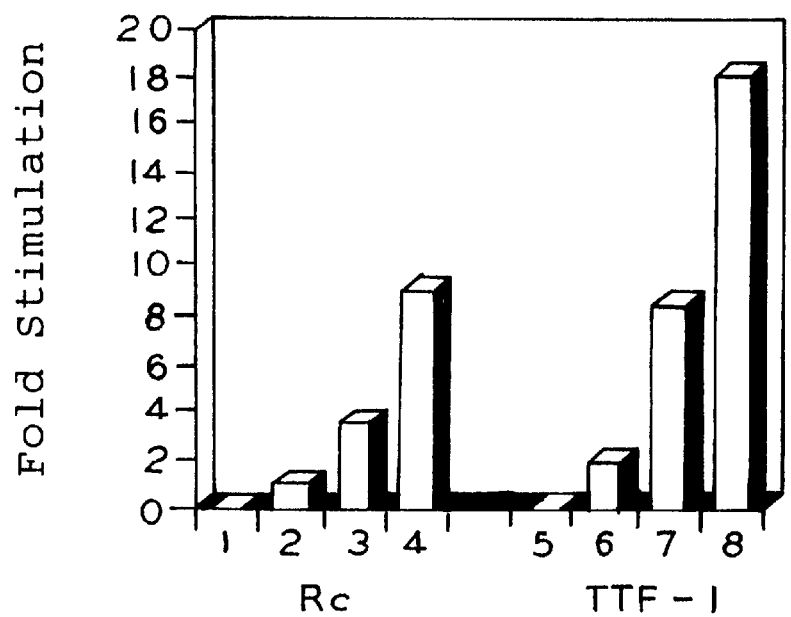
Figure 34C:
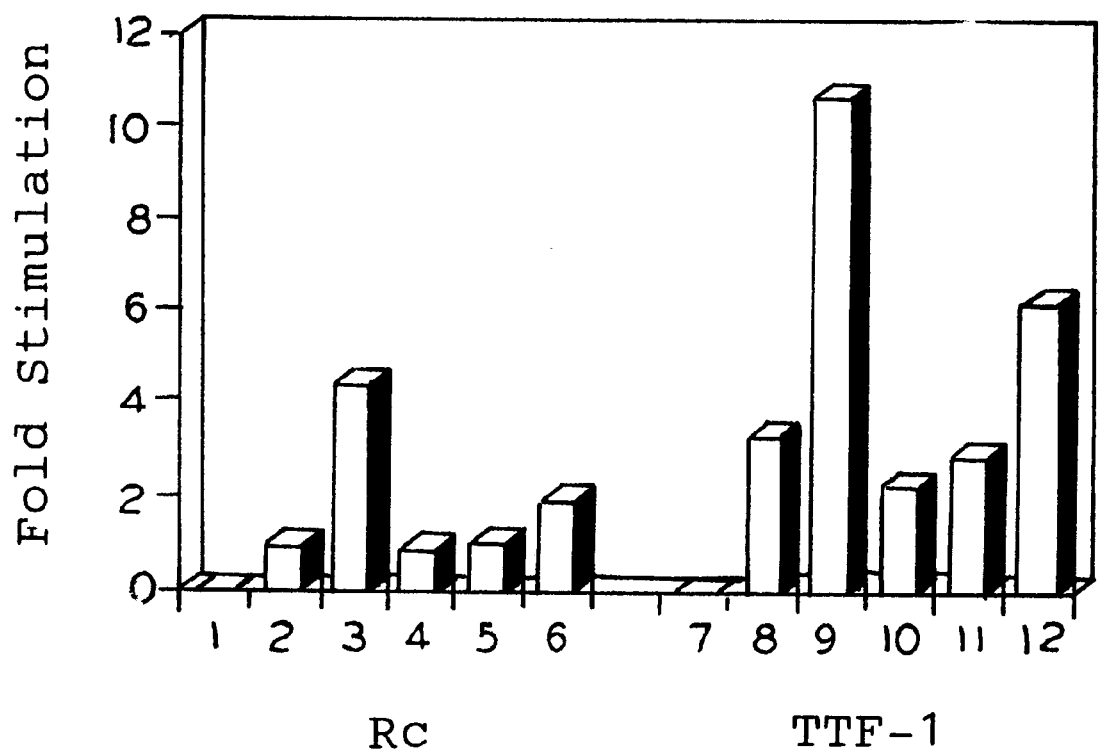
Figure 35A:
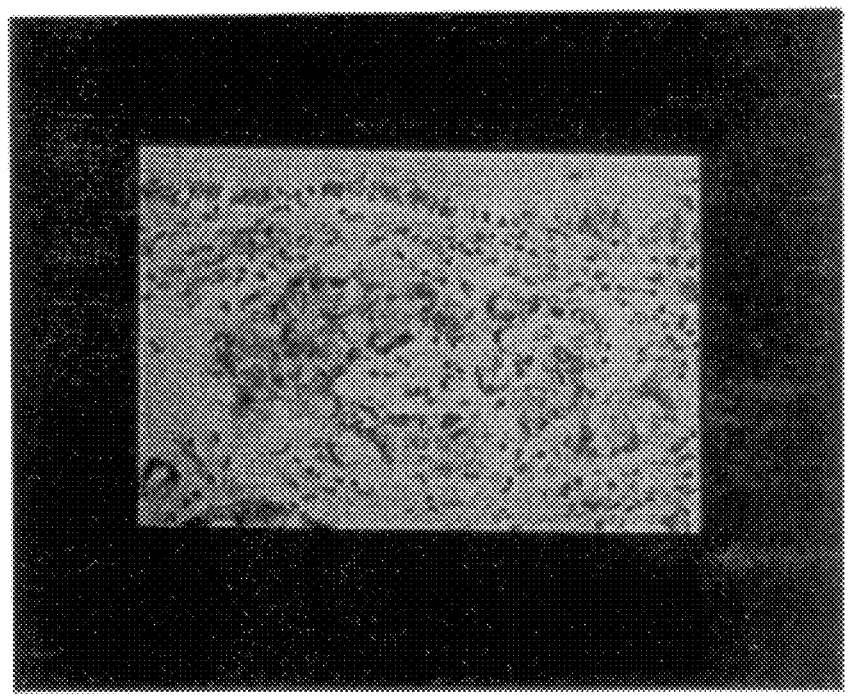
Figure 35B:
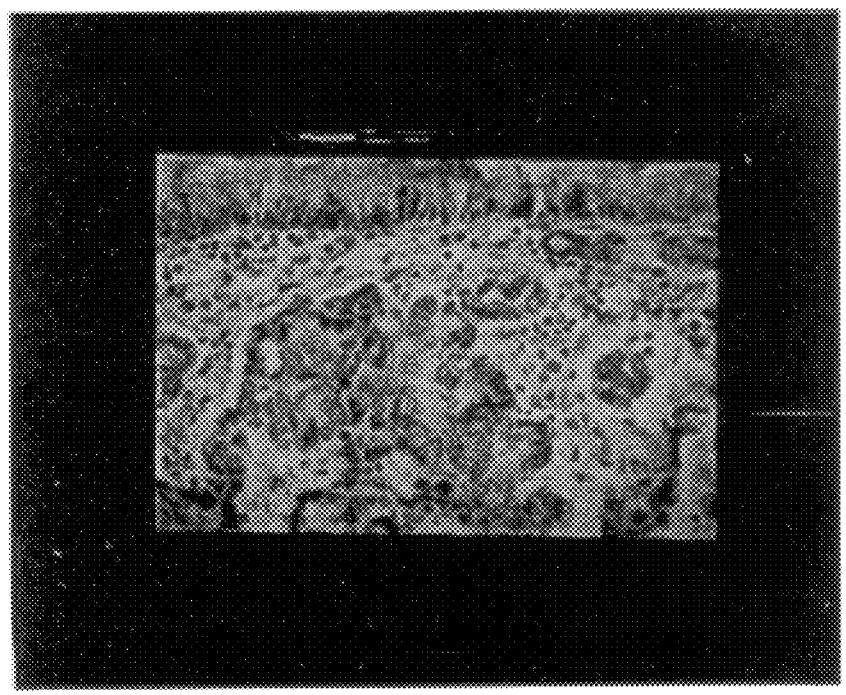
Figure 35C:
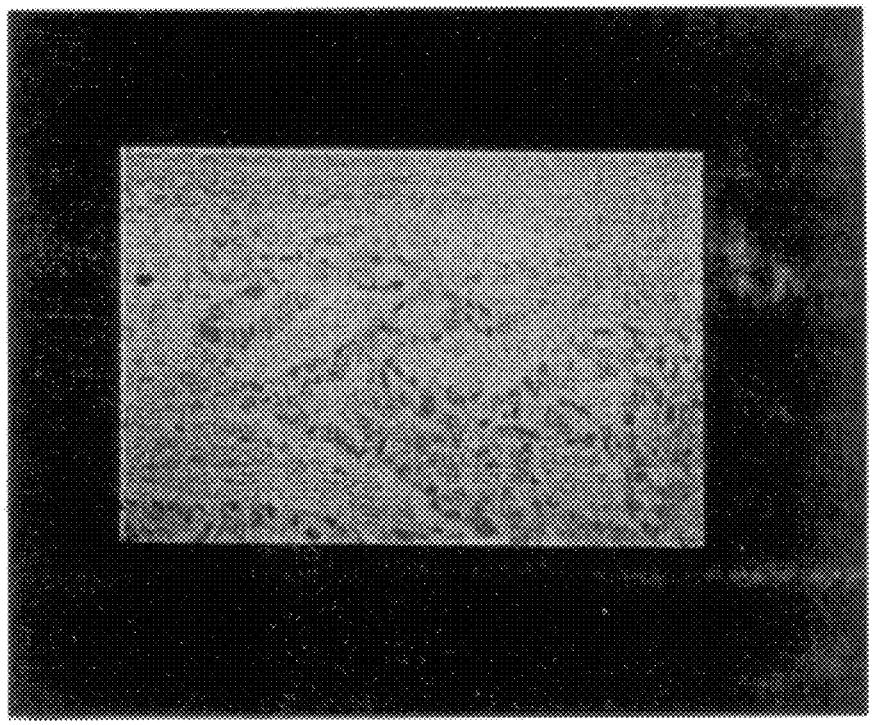
Figure 36A:
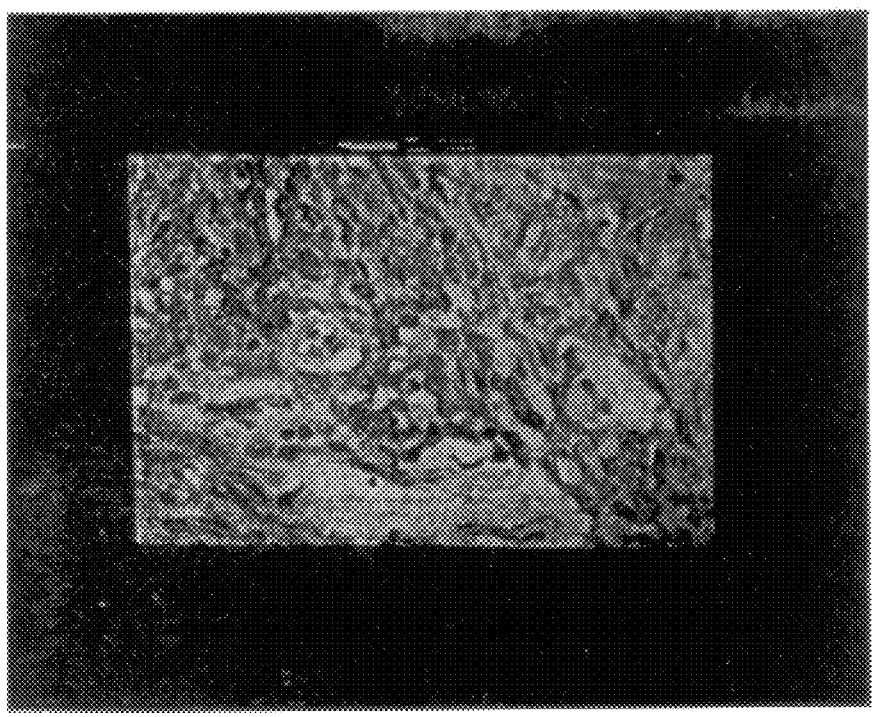
Figure 36B:
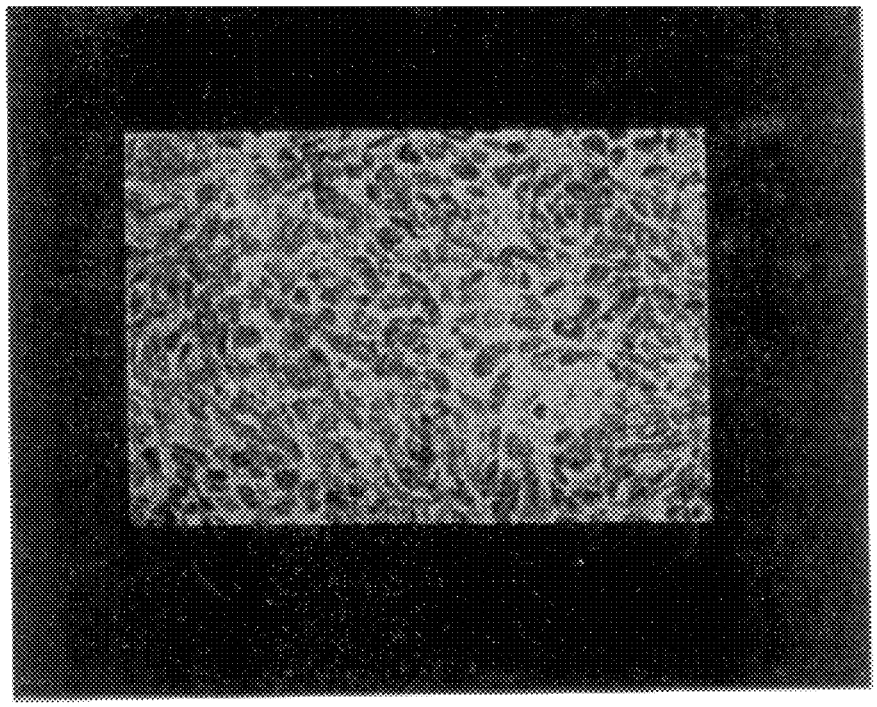
Figure 36C:
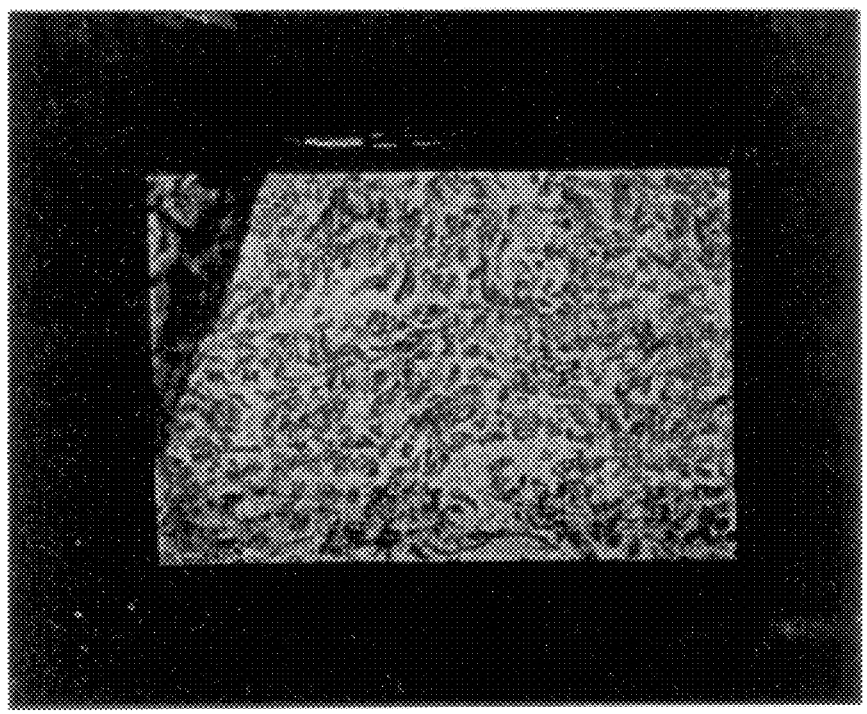
Figure 37A:
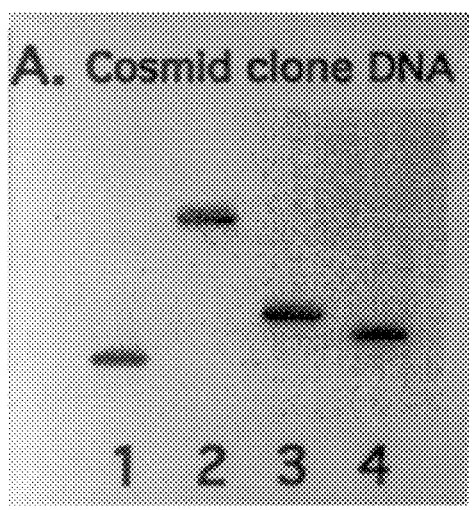
Figure 37B:
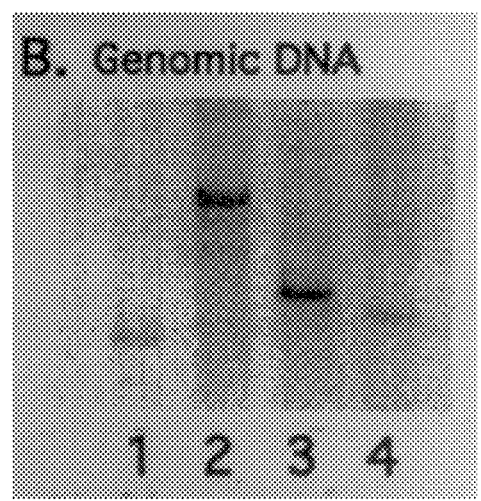
Figure 38A:
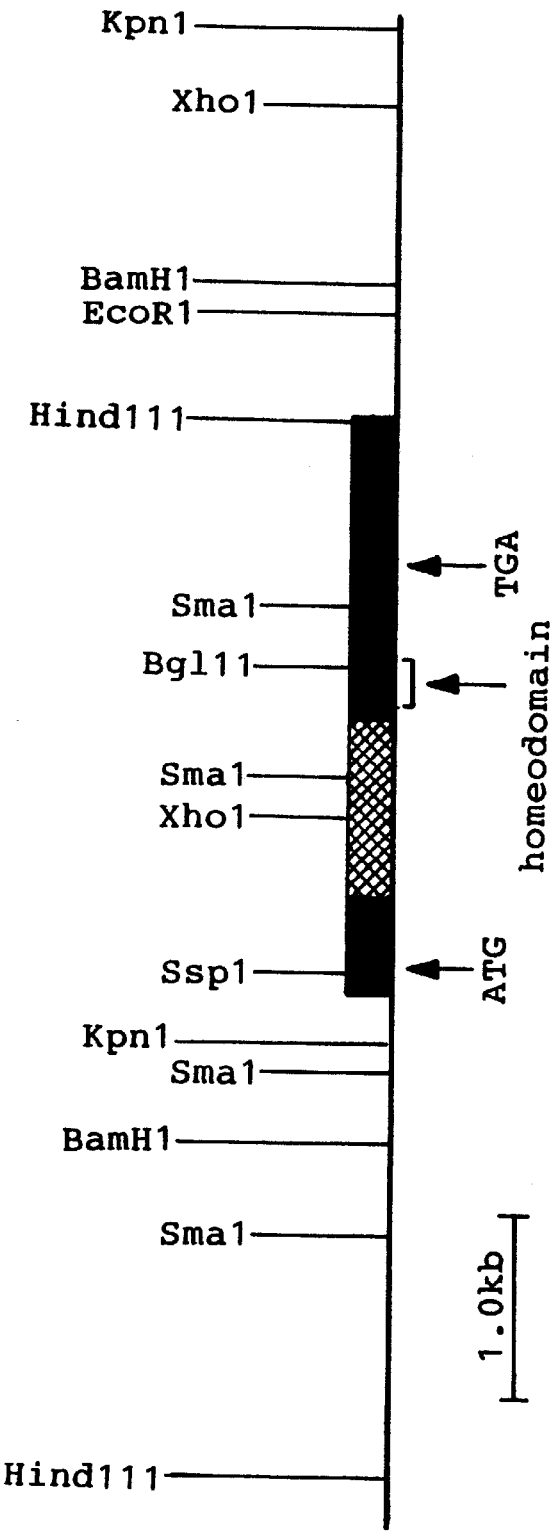
Figure 38B:
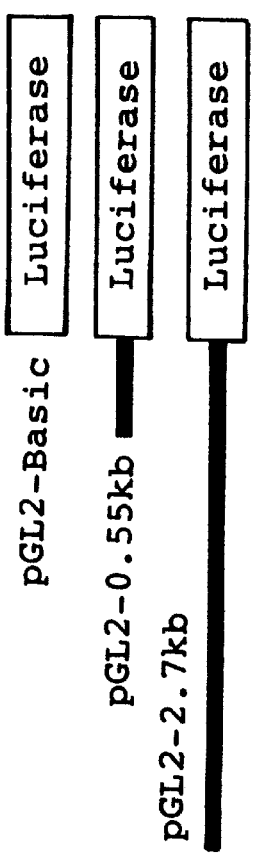
Figure 40A:
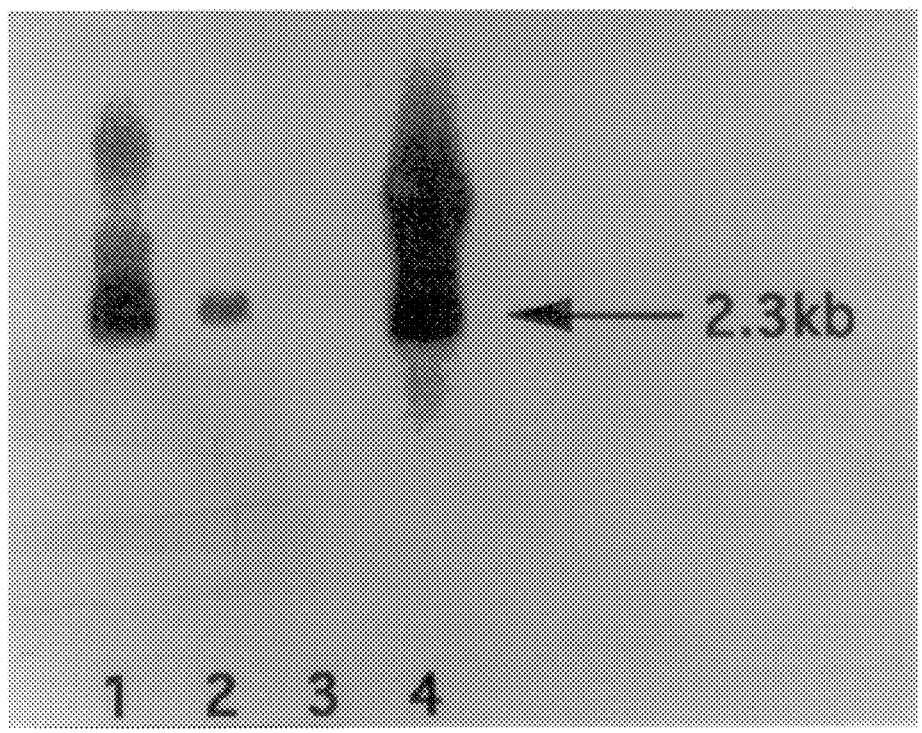
Figure 40B:
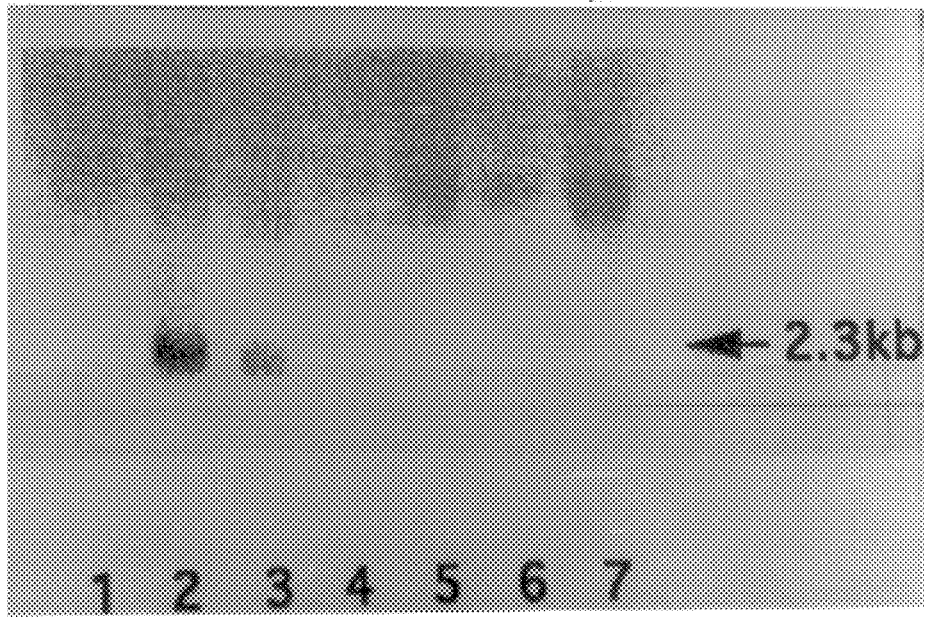
Figure 41:
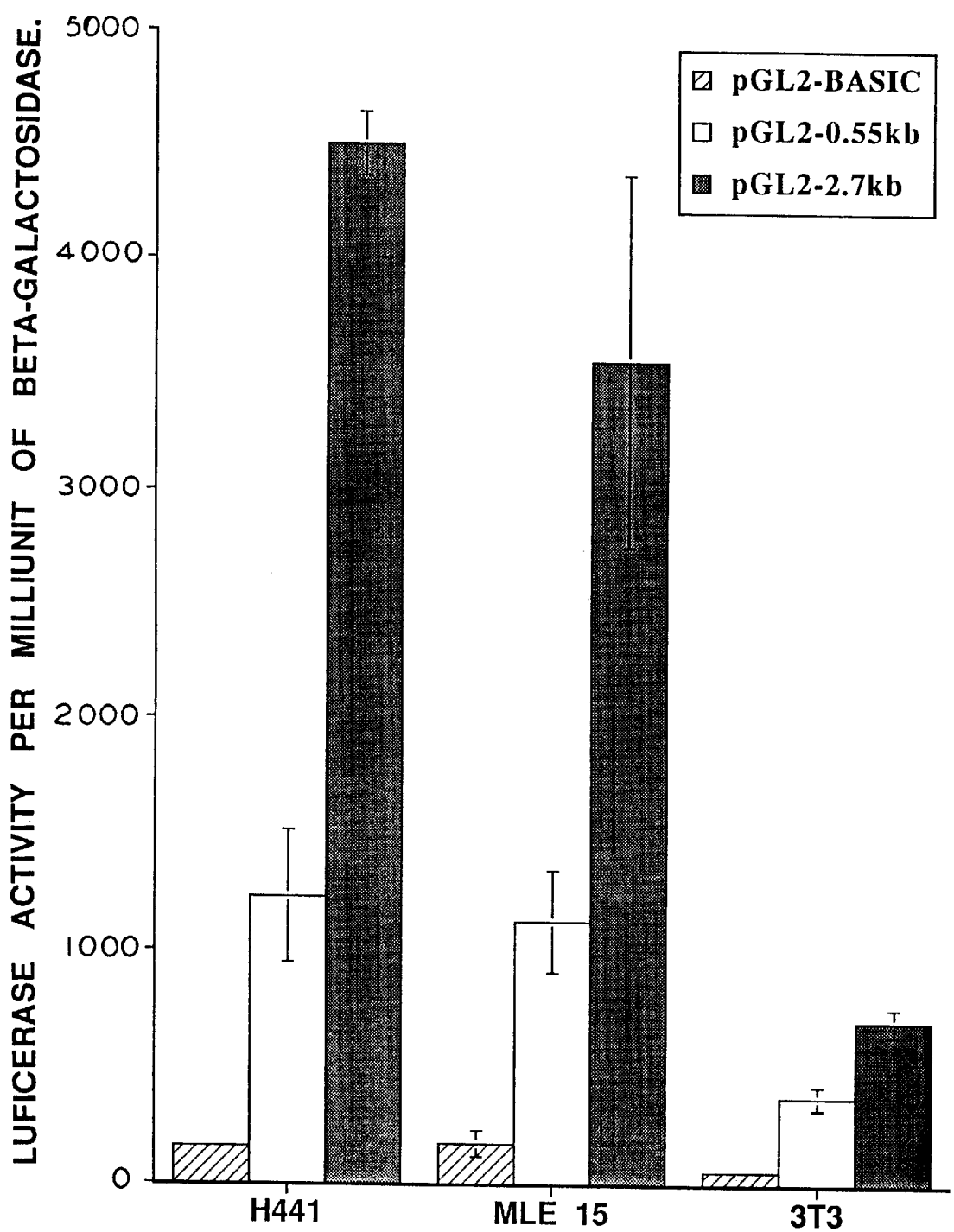

FIG. 10C is a blot of an EMSA assay in which unlabeled competitors f1, C, and f2 were added to an SPB-f1 probe;

FIG. 10D is a blot of an EMSA assay in which unlabeled competitors, antisera to TTF-1, were added to SPB-f1 or SPB-f2, probes, which were tested for binding to MLE-15 nuclear extract or the TTF-1 homeodomain;

FIG. 11A depicts the locations of the TTF-1 and HNF-3 binding sites identified in the SP-B promoter (SEQ ID NO: 51);

FIG. 11B provides relative CAT activity in H441 and HeLa cells transfected with vectors containing wild type or mutated SP-B promoters;

FIGS. 11C and 11D are blots of EMSA assays performed with mutated SP-B probes;

FIG. 12 is a map of plasmid p2244/436;

FIG. 13 is a map of plasmid pBLCAT6;

FIG. 14 is a map of plasmid p218/41-WT;

FIG. 15A is a blot obtained when wild type (WT), TT, or H SP-B promoter constructs were co-transfected with an internal control plasmid pCMVB-gal and either an empty vector or an vector containing the full length TTF-1 cDNA into the HeLa cell line;

FIG. 15B is a blot obtained when a CCSP, SP-C, TTR, or TK promoter was co-transfected with pCMVB-gal and an empty vector or an vector containing the full length TTF-1 cDNA into the HeLa cell line;

FIG. 16 is a schematic of the construction of plasmid pHR;

FIG. 17 is a schematic of the construction of a plasmid including an adenovirus 5' ITR, an encapsidation signal, a Rous Sarcoma Virus promoter, and an adenovirus 5 tripartite leader sequence;

FIG. 18 is a schematic of the construction of plasmid pAVS6;

FIG. 19 is a map of plasmid pAVS6;

FIG. 20 is a map of plasmid pMSPB;

FIG. 21 is a map of plasmid PHSPB;

FIG. 22 depicts maps of adenoviral vectors Av1SPB2 and Av1SPB3;

FIG. 23 is a graph of relative chloramphenicol transferase (CAT) activity in MLE-15 cells, 3T3 cells, H441 cells, and HeLa cells transduced with plasmids containing or not containing TTF-1 binding sites of the murine surfactant protein A gene;

FIG. 24 is a graph of relative CAT activity in HeLa cells transfected with the plasmids depicted in FIG. 23, and wherein such HeLa cells were or were not co-transfected with pCMV-TTF-1;

FIG. 25 depicts the sequences of oligonucleotide probes (SEQ ID NO: 63) through (SEQ ID NO: 67) containing TTF-1 binding sites in the region from base −231 to base −168 of the murine surfactant protein A gene;

FIG. 26 is a blot of an electrophoretic mobility shift assay (EMSA) of surfactant protein A gene probes for binding of such probes with the TTF-1 homeodomain;

FIG. 27 is a blot of an EMSA of surfactant protein A gene probes with MLE-15 nuclear extract proteins;

FIG. 28A is a schematic of the location of mutations in plasmids which contain mutations in the TTF-1 binding sites in the murine surfactant protein A gene;

FIG. 28B is a graph of the relative CAT activity in MLE 15 cells transduced with the plasmid depicted in FIG. 28A;

FIG. 28C is an autoradiogram of CAT assays of MLE-15 cells transduced with the plasmids depicted in FIG. 28A;

FIG. 28D is a graph of the relative CAT activity of HeLa cells transfected with the plasmids depicted in FIG. 28A, wherein such cells were or were not co-transfected with pCMV/TTF-1;

FIG. 28E is an autoradiogram of representative CAT assays of HeLa cells;

FIG. 29A depicts the putative TTF-1 binding sites located in the distal promoter region from base −439 to base −331 (SEQ ID NO: 68) of the human surfactant protein B gene, as well as regions employed in designing oligonucleotides for mutagenesis studies of such putative binding sites;

FIG. 29B depicts schematics of the plasmid constructs (a) B; (b) B-218; (c) B-500; (d) SV40-P; (e) SV40-P F; (f) SV40-P R; and (g) PCR II-C;

FIG. 30 is a graph of SP-B promoter activity in H441 cells transfected with pCMV-Bgal and (i) B; or (ii) SV40-P; or (iii) TK; or (iv) B-218; or (v) B-500;

FIG. 31A is a graph of the inhibition of SP-B proximal promoter (base −218 to base −41) in H441 cells transduced with pCMV-B gal and (i) B; or (ii) B-218; (iii) B-500; and (i) PCR II-C or (ii) PCR II;

FIG. 31B is a blot of an electrophoretic mobility shift assay of the human surfactant protein B (base −439 to base −331) enhancer fragment incubated with H441 cell cytoplasmic or nuclear extracts;

FIG. 32A is a blot of a radio labeled human surfactant protein B (SP-B) enhancer probe (base −439 to base −331) incubated with cytoplasmic or nuclear extracts of H441 cells in the presence of no competitor, self-competitor, or an $F_1$ fragment containing a TTF-1 protein binding site of the SP-B gene;

FIG. 32B is a blot of a radio labeled human surfactant protein B enhancer probe (base −439 to base −331) incubated with recombinant TTF-1 homeodomain protein in the presence of no competitor, self-competitor, an $F_1$ fragment, or an $F_2$ fragment containing an HNF-3 binding site;

FIG. 33A is a graph of the TTF-1 dependent enhancer activity of the SP-B (base −439 to base −331) element on human SP-B promoters;

FIG. 33B is a graph of the TTF-1 dependent enhancer activity of the SP-B (base −439 to base −331) element on the SV40 promoter;

FIG. 34A depicts wild type and mutant oligonucleotides (SEQ ID NO: 69) through (SEQ ID NO: 74) in the SP-B distal promoter element (base −439 to base −331) which were used in EMSA analysis;

FIG. 34B is a blot of an electrophoretic mobility shift assay of the wild type and mutant oligonucleotides shown in FIG. 34A incubated with TTF-1 recombinant homeodomain protein;

FIG. 34C is a graph of the transcriptional activity of wild type B-218 and B-500 plasmids, as well as of mutated B-500 plasmids containing the mutated oligonucleotides shown in FIG. 34A, in H441 cells;

FIG. 35A is a slide of (300×) of a lung adenocarcinoma stained with SP-A antibody;

FIG. 35B is a slide (300×) of a lung adenocarcinoma stained with SP-B antibody;

FIG. 35C is a slide (300×) of a lung adenocarcinoma stained with TTF-1 antibody;

FIG. 36A is a slide (500×) of a small cell carcinoma showing cytoplasmic staining for SP-B;

FIG. 36B is a slide (500×) of a small cell lung carcinoma showing nuclear staining for TTF-1;

FIG. 36C is a slide (500×) of a small cell lung carcinoma showing lack of expression of SP-A;

FIGS. 37A and 37B are Southern blot analyses of the human TTF-1 gene;

FIG. 38A is a restriction map of the human TTF-1 gene;

FIG. 38B is a schematic of the plasmids pGL2, pGL2-0.55 kb, and pGL2-2.7 kb;

Figures 39, 39A, 39C:
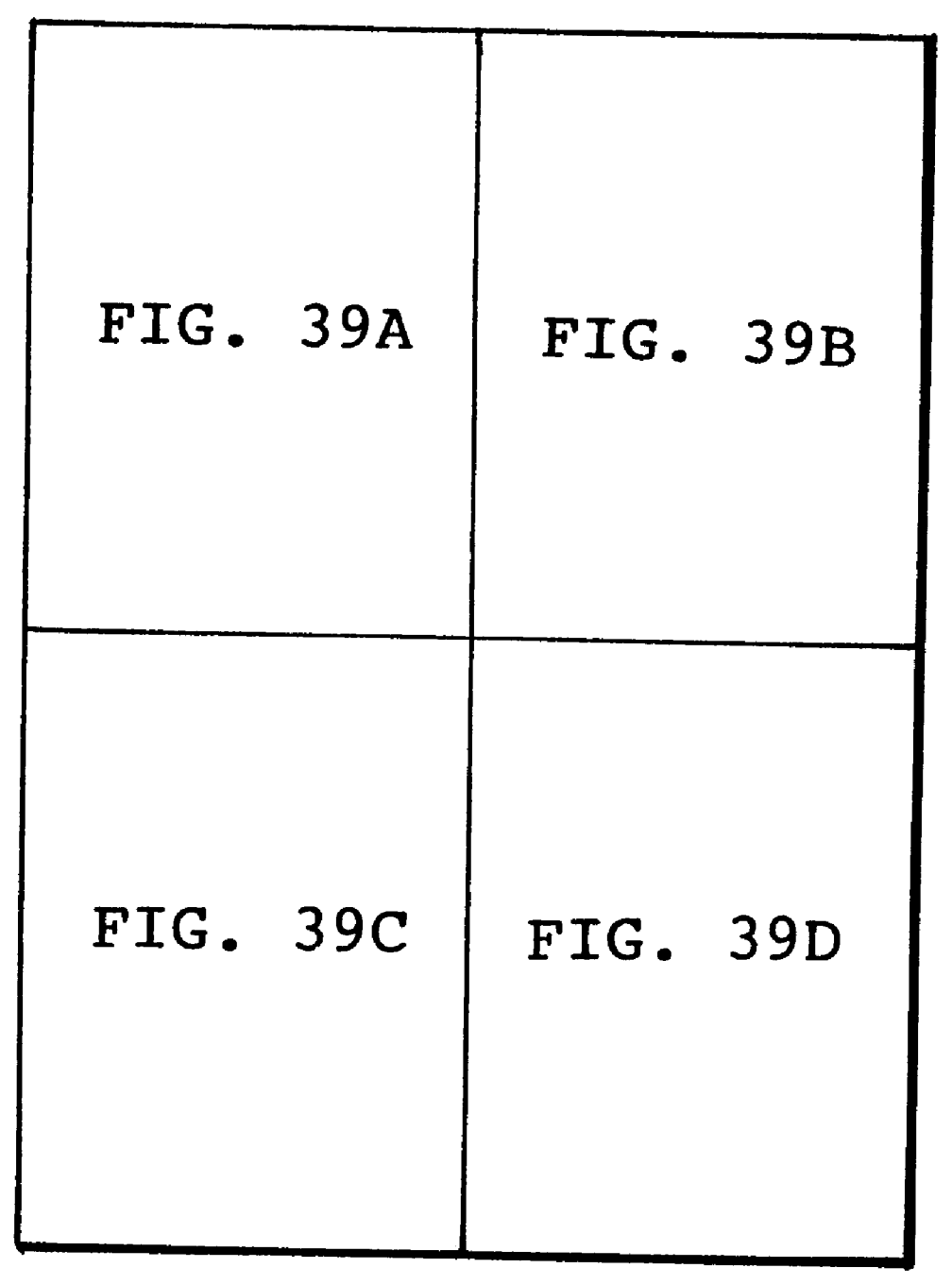

FIG. 39 is the nucleotide (SEQ ID NO: 75) and predicted amino acid (SEQ ID NO: 75) sequence of the human TTF-1 gene. The major start of transcription is marked +1, and the polyadenylation signal (AATAAA) is underlined;

FIGS. 40A and 40B are Northern blot analyses of TTF-1 mRNA in mouse lung and human and mouse pulmonary adenocarcinoma cells;

FIG. 41 is a graph of luciferase activity of pGL2, pGL2-0.55 kb, and pGL2-2.7 kb in pulmonary adenocarcinoma cells and 3T3 fibroblasts; and FIGS. 42A, 42B, 42C, 42D, 42E, and 42F are microscope slides of fetal, newborn, and adult lung tissue stained for the presence of TTF-1.

EXAMPLES

The invention now will be described with respect to the following examples; however, the scope of the present invention is not intended to be limited thereby.

Example 1

Identification of Cis-active Elements Controlling Human Surfactant Protein B Gene Expression Materials and Methods DNase I hypersensitivity—H441 and RAJI cells were disrupted by Dounce homogenization in polyamine buffers modified from that of Hewish, et al., *Biochem. Biophys. Res. Commun.*, Vol. 52, pgs. 504–510 (1973).

The use of the polyamine buffer was critical in that DNA purified from nuclei that contained calcium exhibit substantial cleavage at the typical hypersensitive sites even in the absence of added DNase I. The polyamine buffer contained 0.34 M sucrose, 53 mM KCl, 13 mM NaCl, 2 mM EDTA, 0.5 mM EGTA, 0.13 mM spermine, 0.5 mM spermidine, 14 mM freshly prepared 2-mercaptoethanol, 0.1% Triton X-100, 13 mM Tris-HCl, pH 7.4, 3 mM $MgCl_2$, and 1mM freshly prepared phenylmethylsulfonyl fluoride. Nuclei were prepared from the homogenates and centrifuged at 2,400×g for 30 minutes over a cushion of 1.2 M sucrose in polyamine buffer. The nuclear pellet was washed twice in polyamine buffer without sucrose and detergent and resuspended in a DNase I digestion buffer that contained 60 mMKCl, 5 mM $MgCl_2$, 0.1 mM EGTA, 0.5 mM dithiothreitol, 5% glycerol, and 15 mM Tris-HCl, pH 7.5. Nuclei were resuspended at a concentration of $1.25 \times 10^7$ to $3.5 \times 10^7$ nuclei/ml, and gentle DNase I digestions were carried out in a volume of 0.2 ml with 7 units of DNase I (Bohringer Mannheim) at 30° C. for 1, 2.5, 5, 10, and 15 minutes. Zero time points were not subjected to DNase I. DNA was prepared from nuclei treated or untreated with DNase I by the addition of an equal volume of a buffer that contained 0.6 M NaCl, 20 mM EDTA, 20 mM Tris-HCl, pH 7.5, and 0.5% SDS. The nuclear lysates were digested with 40 µg/ml of heat-treated RNase A for 2 hours at 50° C. followed by 300 µl/ml of proteinase K overnight at 37° C. DNA was purified by phenol extraction and ethanol precipitation and quantitated spectrophotometrically. DNA samples were digested with HindIII, electrophoresed through agarose gels, blotted to Nytran, and hybridized to probe radio labeled by means of random primers. The probe was a 1044-bp PCR subfragment of the SPB genomic clone PG13-2 (bp 6053–7096) and is shown to scale in FIG. 1C.

Plasmids—The isolation and cloning of the entire SPB gene has been reported in Pilot-Matias, et al., DNA, Vol. 8, pgs. 75–86 (1989). Clone λ PG13-2 contains the entire SPB gene and more than 2.2 kb of 5' flanking sequence (Pilot-Matias, et al., 1989). λ PG13-2 was used to clone sequence for all SPB constructions.

Plasmids pSV40-CAT, pRSV-CAT, and pCMV-βgal have been described in Gorman, et al., *Mol.Cell.Biol.*, Vol. 2, pgs. 1044–1051 (1982) and Miller, *Experiments in Molecular Genetics*, Cold Spring Harbor Laboratory, Cold Spring Harbor, N.Y., pgs. 352–355 (1972). p2244/436-CAT contains SPB genomic sequence from −2244 to +436 in the HindIII site of pSVO-CAT and was constructed in three steps. First, the 2.2-kb SalI-KpnI SPB genomic fragment (bp −2244 to −4) was subcloned into the corresponding sites of pUC19. Second, these sequences were liberated from the polycloning site of pUC-19 by digestion with HindIII and EcoRI and introduced into the HindIII site of pSVO-CAT with HindIII linkers in a 5' to 3' orientation with respect to the CAT gene to give plasmid p2.2-CAT. Sequences downstream of the KpnI site (−5 to +436) were amplified from λ PG13-2 using the PCR to generate a Kpn I-HindIII- linkered fragment containing a single base pair substitution at +15 (A to T). This fragment was cloned into the KpnI and downstream HindIII site of p2.2-CAT to give p2244/436-CAT. The single base pair change at +15 alters the translation start signal encoded in SPB exon I (AUG to DUG) and was necessary to prevent the generation of an SPB-CAT fusion protein. (Alam, et al., *Biotechniques*, Vol. 10, pgs. 423–425 (1991)).

5'-Flanking deletions were constructed from p2244/436-CAT by digestion with NdeI followed by complete digestion with SacI (pΔ5'−1993), SauI (pΔ'−1552), BstEII (pΔ5'−1414). StuI (pΔ5'−900), PpuMI (pΔ5'−650), SfiI (pΔ5'−366), or BstXI (pΔ5'−218). Recessed 5' or 3' termini were subsequently blunt ended with T4 DNA polymerase and plasmids recircularized with T4 DNA ligase. pΔ5'−80 was constructed using PCR to generate a HindIII-linkered SPB subfragment (bp −80 to +436) which was subcloned into the HindIII site of pSVO-CAT.

Plasmid (pdl (+112/+318)) was constructed by digestion of p2244/436-CAT with AvrII and XbaI followed by recircularization. pΔ3'+41 was constructed by complete digestion of Δ5'−1993 with HindIII and BspMI followed by end filling with T4 DNA polymerase and recircularization. pΔ3'+7 contains SPB sequence −2244 to +7 and represents the assembly of SalI and PstI subfragments in the HindIII site of pSVO-CAT. Plasmid (pdl(+8/+38)) was constructed from p2244/436-CAT by partial digestion of PstI followed by recircularization. p218/41 was constructed by digestion of pΔ5'−218 with BspMI and HindIII followed by recircularization. Following propagation in DH5α *Escherichia coli*, the identity of all constructions was confirmed by restriction mapping, and PCR subfragment sequences were confirmed by dideoxy sequence analysis.

Cell Culture—Human lung adenocarcinoma cell line NCI-H441 was maintained in RPMI medium containing 10% fetal bovine serum. Human lung adenocarcinoma cell line A549 and HeLa cells were maintained in Dulbecco's modified Eagle's medium containing 10% fetal bovine serum. GM 4671 (RAJI) is a human B-lymphoid cell line and was maintained as described in Aronow, et al., *Genes & Dev.*, Vol. 3, pgs. 1384–1400 (1989). All cell lines were cultured at 37° C. and 5% $CO_2$.

Transient Transfection—A mixture of 5 pmol of test plasmid was mixed with 2.5 pmol of the internal control plasmid pCMV-βgal and coprecipitated by the calcium phosphate procedure. Precipitates (1 ml) were added directly to the tissue culture medium. Eighteen to 24 hours subsequent to transfection the cells were washed and the medium was changed to RPMI with 10% fetal bovine serum. Cells were harvested by scraping 24 or 48 hours later. Assays for β-galactosidase were performed according to Miller, 1972. (CAT assays were performed as described by Gorman, et al., *Mol.Cell.Biol.*, Vol. 2, pgs. 1044–1051 (1982). Chloramphenicol, [dichloroacetyl-1, 2-$^{14}$C], and its derivatives were separated by thin layer chromatography. The percent acetylation was quantitated using a Molecular Dynamics PhosphorImager. To ensure linearity of the assay, data were quantitated from CAT assays in which less than 20% conversion had occurred. Relative CAT activities were calculated by comparing the activities of the promoter-containing plasmids with the activity of pSVO-CAT (which produced 0.082% acetylation/unit of β-galactosidase activity/h in H441 cells and 0.018% acetylation/unit of β-galactosidase activity/h in HeLa cells) within each cell line following correction for transfection efficiency. Although transfection efficiencies (units β-galactosidase activity/μg protein) and absolute CAT conversion varied between experiments (approximately 2–10-fold), relative CAT activities were similar between experiments.

DNase I footprinting-HeLa nuclear extracts were made according to Jacob, et al., *J.Biol.Chem.*, Vol. 266, pgs. 22537–22544 (1991). H441 extracts were made according to Shapiro, et al., *DNA*, Vol. 7, pgs. 47–55 (1988), with modifications as described in Stripp, et al., *J.Biol.Chem.*, Vol. 267, pgs. 14703–14712 (1992). DNA probes for footprint analysis were prepared by using the PCR and $^{32}$P-end-labeled synthetic oligonucleotide primers. The SPB genomic clone, λ PG13-2, was used as template for the amplification of sequence between base pairs −221 and +81. The upstream and downstream primers used were (5'-CAGGAACATGGGAGTCTGGG) (SEQ ID NO.: 29) and (5'-CAGTGCCTGGGCCACAGAGC), (SEQ ID NO.: 30) respectively. The upstream or downstream primer (3 pmol) was $^{32}$P-end-labeled in a 20 μl kinase reaction mixture containing 30 pmol of [γ$^{32}$P] ATP as described. (Maniatis, et al., *Molecular Cloning: A Laboratory Manual*, 2nd ed., pgs. 11.31–11.32, Cold Spring Harbor Laboratory Press (1989).

Kinase reactions were terminated by incubation at 65° C. for 10 min and added directly to a standard 100-μl PCR reaction mixture containing 3 pmol of unlabeled primer oligonucleotide and 500 ng of template DNA. PCR products were isolated using Promega PCR Preps DNA Purification System.

The DNase I protection assay was performed in a 50-μl reaction. DNA binding reactions were carried out in a mixture containing 10 mM Tris, pH 7.5, 0.5 mM dithiothreitol, 5 mM MgCl$_2$, 0.1 mM EDTA, 75 mM KCl, 0.2 mM phenylmethylsufonyl fluoride, and 12% glycerol. Nuclear proteins were incubated with 2 μg of poly(dI.dC) competitor DNA for 15 min at 0° C. prior to the addition of 20,000 counts/min. of labeled DNA (about 0.3 ng). After another 60-min incubation at 0° C., the samples were set at room temperature and after 5 min. digested with DNase I (Promega) for 2 min. The reactions were stopped by the addition of 350 μl of stop buffer containing 230 mM NaCl, 17 mM EDTA, 1.14% SDS, 11.4 mM Tris, pH 7.8, and 230 μg/ml proteinase K. DNA was purified by phenol extraction and ethanol precipitation. DNA samples were fractionated on 6% polyacrylamide, 7 M urea sequencing gels.

RESULTS

Identification of DNase I hypersensitive Sites Flanking the SPB Promoter—Because many enhancer-like elements and other functional regions are associated with perturbations of chromatin structure, DNase I hypersensitivity (DH) assays were used to evaluate the SPB gene and 5'-flanking DNA. A 12.1-kb HindIII fragment was used to map DH sites. This fragment contained over 5 kb of 5'-flanking sequence and over 8 kb of intragenic sequence extending to HindIII site in intron 10. Autoradiograms of the indirectly end-labeled fragments that were generated by DNase I treatment of nuclei are shown in FIG. 1, A and B. Nuclei were analyzed from a human lung adenocarcinoma cell line (H441), a non-lung cell line (RAJI), and human thymus. A total of four hypersensitive sites were identified in H441 cell nuclei (Roman numerals, FIG. 1A). These sites, designated DNase I-hypersensitive sites I to IV (DHI-DHIV), were located proximal to the SPB promoter and within intron eight of the gene. Each site was mapped in two separate experiments by comparison of the DNase I liberated fragments to known molecular weight standards. The locations of these sites are summarized in FIG. 1C. An identical procedure detected no DH sites in preparations of RAJI cell nuclei (a non-lung human B-lymphoid cell line). (FIG. 1B.). These data suggest that chromatin in H441 cell nuclei, but not non-lung cell nuclei, exists in a unique structure which is sensitive to DNase I and indicates that important regulatory regions may lie in close proximity to the promoter or within the gene.

Figure 2A:
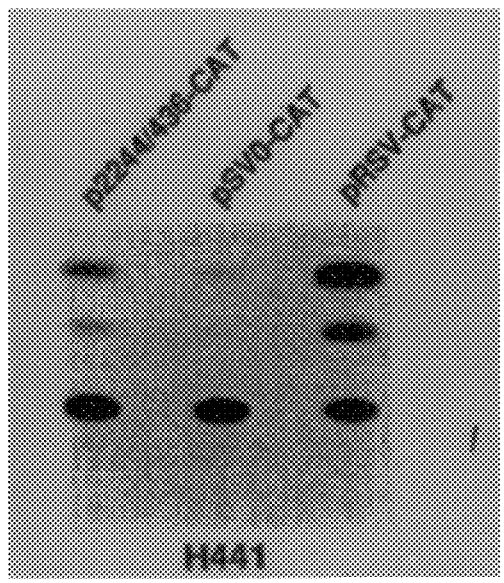
FIGS. 2A, 2B, and 2C are blots of cell-specific function of the SPB promoter region in H441, A549, and HeLa cells.
Figure 2B:
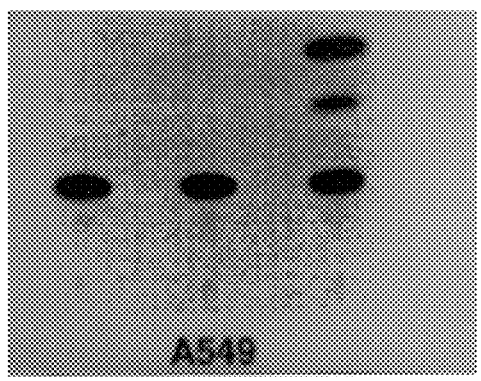
Figure 2C:
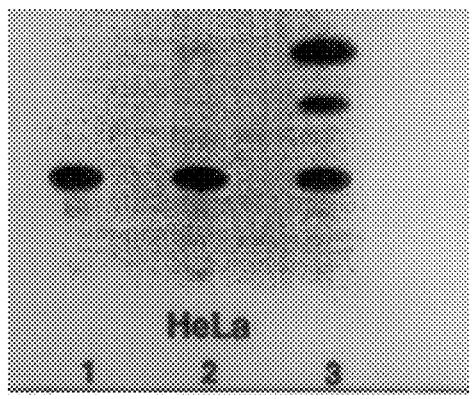

Sequences Flanking the SPB Promoter Direct Lung Cell-specific Expression—To determine if sequences encompassing DNase I hypersensitive sites I and II were associated with functional transcriptional regulatory domains, 2.7 kb of sequence (−2244 to +436) was linked to a CAT reporter gene. The transcriptional activity of this construction (p2244-436-CAT) in the indicated cell lines was determined by transient transfection. Each plasmid (5pmol) containing the CAT reporter gene was co-transfected along with pCMVβ-gal into H441, A549, and HeLa cell lines. CAT activity was measured 48 hrs. later and normalized to β-galactosidase activity. The activity in each cell line is compared to that of pSV40-CAT. pRSV-CAT was employed as an external positive control for CAT activity. Increased transcription of the CAT reporter was observed only in H441 cells, where an approximate 10-fold increase in expression relative to promoterless vector pSVO-CAT was observed (FIG. 2A, lanes 1 and 2). Transfection of p2244/436 into A549 cells, a human pulmonary adenocarcinoma cell line that does not express SPB, or HeLa cells did not support CAT transcription above promoterless vector (FIG. 2, B and C, lanes 1 and 2). This result indicated that a human lung adenocarcinoma cell line, H441, was capable of expressing chimeric SPB-CAT genes and that the human SPB gene promoter and flanking sequences contained within −2244 to +436 was transcriptionally active in a cell type-specific manner.

To determine if sequence encompassing hypersensitive sites III and IV contained additional regulatory elements, a genomic subfragment spanning intron eight was subcloned into the BamHI site downstream of the CAT reporter gene and SPB promoter and flanking sequence (−2244 to +436). The transcriptional activity of this construction was similar to p2244/436-CAT (data not shown). This result suggested that DHIII and DHIV were not associated with a typical enhancer element.

Figure 3:
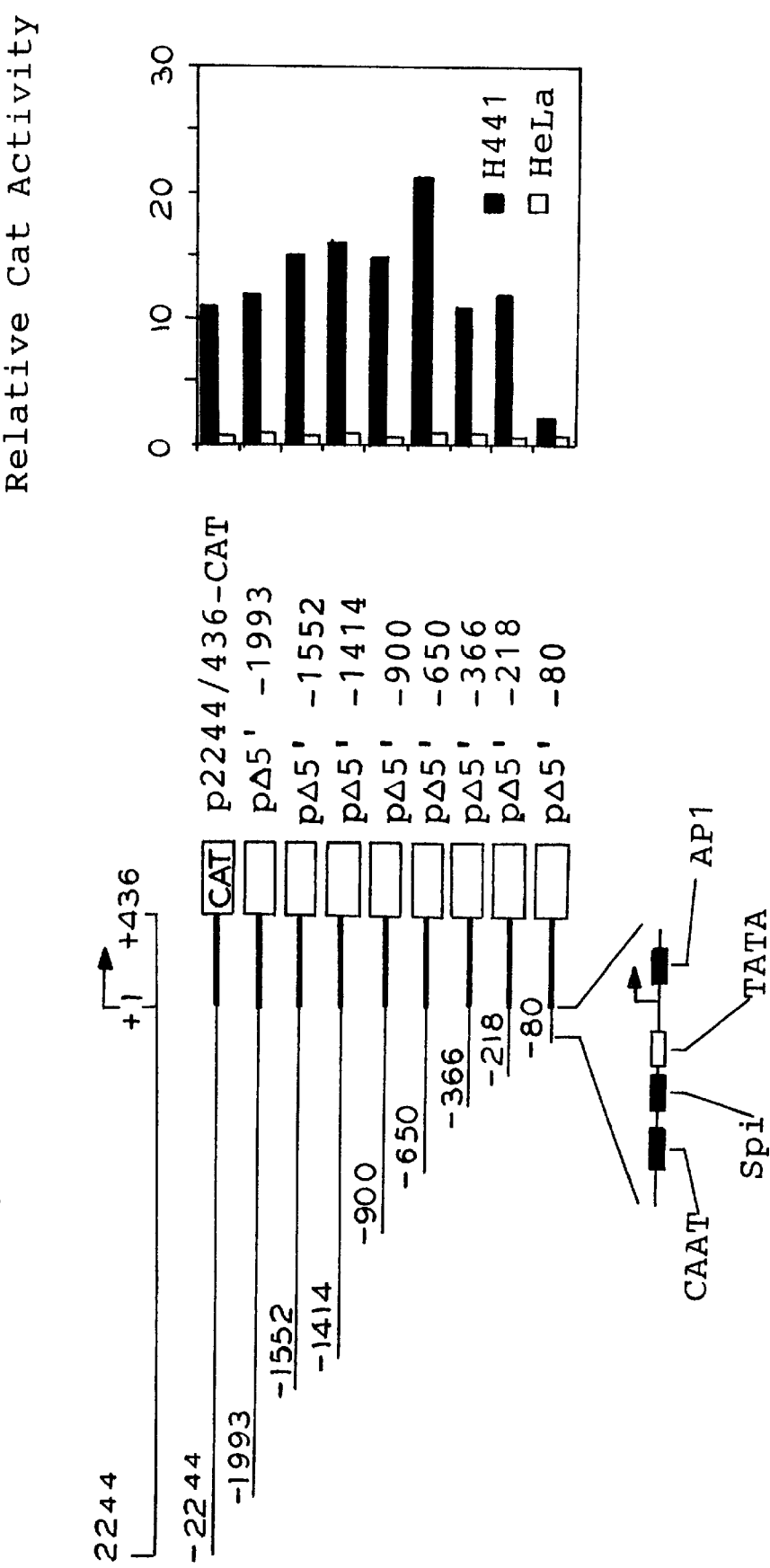
FIG. 3 depicts a schematic of plasmids having 5' deletions in the SPB promoter region, and including a CAT gene, and depicts a graph of relative CAT activity of these plasmids when transfected into transfected into H441 and HeLa cells.

Deletion Analysis of Sequence Flanking the SPB Promoter—To delineate better the cis-acting sequences that regulate SPB transcription in H441 cells, a series of 5'-flanking deletions of SPB sequence were analyzed in transient expression assays. The deletion mutants were constructed as hereinabove described, and each 5' deletion mutant had the same 3' end point at +436, containing sequence into SPB exon 2. Each plasmid was co-transfected with pCMV-β-galactosidase activity. Relative CAT activities were calculated by comparing the activities of the SPB promoter containing plasmids with those of pSV40-CAT as hereinabove described. A summary of the results obtained from transfection of these CAT reporter constructs is shown in FIG. 3. As shown in FIG. 3, the lower line shows the location of consensus binding site motifs found within the SPB promoter region. Each construction was assayed for expression in both H441 and HeLa cell lines. CAT activity varied in H441 cells with deletion of 5'-flanking DNA to −218 (pΔ5'-218), but there was no loss of activity relative to p2244/436-CAT and no construction expressed above the level of pSVO-CAT in HeLa cells. However, deletion of sequence to −80 (pΔ5'-80) resulted in 82% reduction in reporter activity compared to p2244/436-CAT, suggesting that a positive cis-active element was located between −218 and −80.

In order to determine if additional regulatory elements were located downstream of the SPB transcription site, a series of 3' introgenic deletion mutants was constructed. The extent of each deletion is shown relative to p2244/436 by broken lines. Each 3' deletion mutant had the same 5' end point at −2244 bp. Each plasmid was co-transfected with pCMV-βgal into H441 and HeLa cells, and CAT activity was normalized to β-galactosidase activity. Relative CAT activities were calculated by comparing the activities of the SPB promoter-containing plasmids with those of SV40CAT as hereinabove described.

Figure 4:
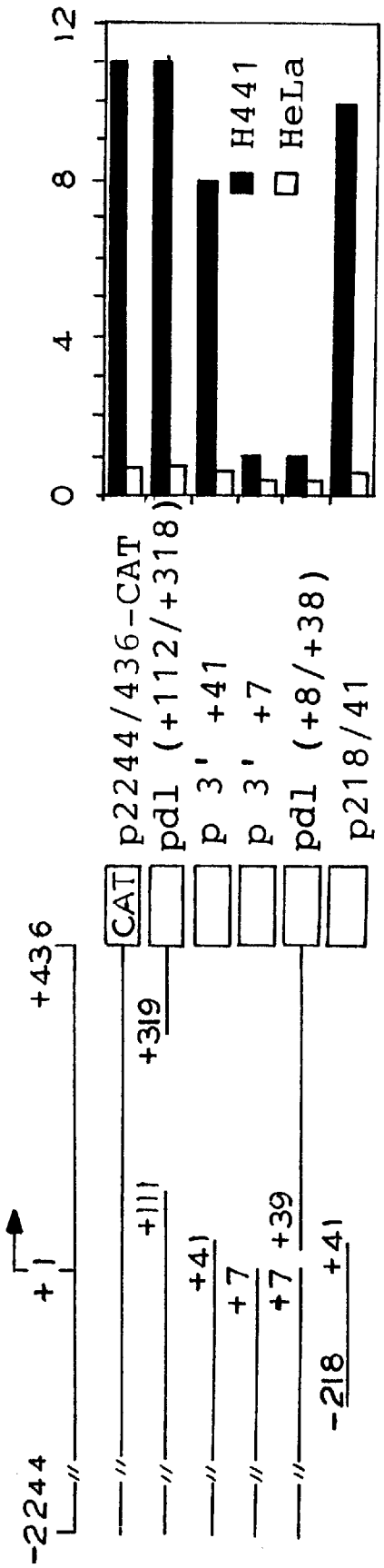
FIG. 4 depicts a schematic of plasmids having 3' deletions in the SPB promoter region, and including a CAT gene, and depicts a graph of relative CAT activity of these plasmids when transfected into H441 and HeLa cells.

A summary of the results obtained from transient expression of these CAT reporter constructs in H441 and HeLa cells is shown in FIG. 4. Deletion of 3'-flanking DNA to +41 (pΔ3'+41) or internal deletion of sequence encompassing most of the first intron (pdl(+112/+318)) did not significantly alter reporter gene activity. Further deletion of 3'-flanking DNA to +7 (pΔ3'+7) reduced reporter gene activity by 91% compared to p2244/436-CAT. In addition, internal deletion of sequence encompassing nucleotides +8 to +38 (pdl(+8/+38)) also reduced transcriptional activity by 91%. This result suggests the existence of a second positive regulatory element located between +8 and +38. Finally, the deletion of both 5'-flanking DNA to −218 and adjacent intragenic DNA to +41 (p218/41) demonstrated that a 259-bp promoter fragment was sufficient to support a level of cell type-specific CAT expression similar to p2244/436-CAT.

Figures 5A, 5B:
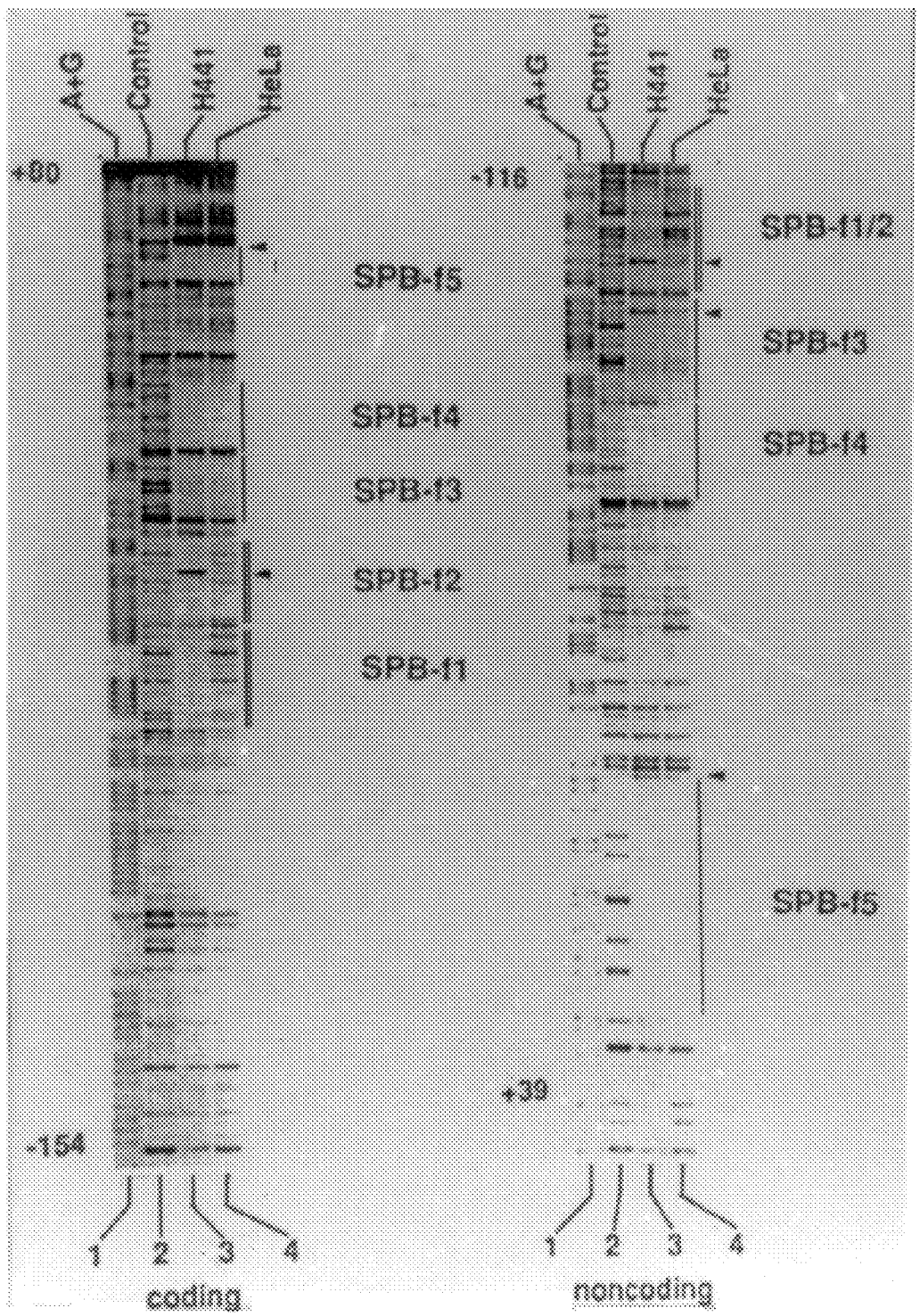
FIGS. 5A and 5B are a blot of DNase I footprint analysis of the SPB cell-specific promoter using H441 lung cell and HeLa cell nuclear extracts.

Identification and Cellular Specificity of Nuclear Protein-binding Sites within the SPB Promoter—To identify nuclear protein-binding sites within the SPB promoter and flanking sequence, DNase I footprinting experiments were performed using extract prepared from lung (H441) and non-lung (HeLa) cell lines. A 300bp fragment (bp −220 to +80) containing the SPB lung cell-specific promoter was subjected to DNase I footprint analysis using H441 lung cell and HeLa cell nuclear extracts. The coding (FIG. 5A) and non-coding (FIG. 5B) strands of the 300 bp fragment were end labeled and incubated in the absence (control, lane 2) or presence of H441 (lane 3) or HeLa (lane 4) nuclear extracts before partial digestion with DNase I. Standard Maxam and Gilbert purine (A+G) sequencing reactions of the same fragments were run in parallel (lane 1). Protected sequences identified within H441 nuclear extract are indicated with double lines in FIGS. 5a and 5B and labeled SPB-f1 and SPB-f2. Sequences protected by both H441 and HeLa nuclear extracts are indicated in FIGS. 5A and 5B with single lines and labeled SPB-f3, SPB-f4 and SPB-f5. Arrowheads in FIGS. 5A and 5B denote sites hypersensitive to DNase I.

Five nuclear protein-binding sites were identified using H441 nuclear extracts on both the coding and non-coding DNA strands (single and double lines, FIG. 5, A and B). In addition, multiple DNase I hypersensitive sites, reflected as more intense bands of digestion, were observed between and within some of the footprinted regions (arrowheads, FIG. 5, A and B). This type of DNase I footprint has been described previously for complex promoters and enhancers containing multiple closely spaced cis-active elements and may reflect the bending of DNA adjacent to these sites (Gottschalk, et al., *Mol.Cell.Biol.*, Vol. 10, pgs. 5486–5495 (1990); Ho, et al., *Proc.Nat.Acad.Sci.*, Vol. 86, pgs. 6714–6718 (1989)).

Two footprinted regions, designated SPB factor 1 (SPB-f1; bp −107 to −93) and SPB factor 2 (SPB-f2; bp −90 to −73), were protected only with H441 cell nuclear extract (double lines, FIG. 5, A and B). The 5'-most binding site, SPB-f1, did not contain any previously identified enhancer or promoter motif. SPB-f2 contained a sequence motif for hepatocyte nuclear factor 5 (HNF-5; TGTTTGT) (SEQ ID NO:31), a transcription factor previously described in liver. (Rigaud, et al., *Cell*, Vol. 67, pgs. 977–986 (1991); Grange, et al., *Nucleic Acids Res.*, Vol. 17, pgs. 8695–8709 (1989)).

Three additional nuclear protein-binding sites were identified in both H441 and HeLa cell nuclear extracts (single lines, FIG. 5, A and B) and designated SPB factor 3 to 5 (SPB-f3 to SPB-f5). SPB-f3 contained a six of nine match to the consensus CAAT box. SPB-f4 contained a TATA box and Sp1-binding site motif. Notably, SPB-f5 was located entirely within the protein coding region of the gene and encompassed a consensus AP1-binding site motif (5'-TGAGTCA) (SEQ ID NO: 32). The locations of protected sequences and binding site motifs are summarized in FIG. 6.

As shown in FIG. 6, nuclear protein-binding sites identified within the SPB lung cell-specific promoter region are indicated for the coding and non-coding DNA strands above and below the nucleotide sequence, respectively. Sites detected only with H441 lung cell nuclear extract are indicated by double lines and labeled SPB-f1 and SPB-f2. Sites protected by both H441 and HeLa nuclear extract are indicated with single lines and labeled SPB-f3, SPB-f4 and SPB-f5. The numbers correspond to the limits of protection for each binding site. The TATA box, CAAT box, Sp1, and AP1 consensus binding site motifs are indicated in boldface print. The SPB-f2 site contains an HNF 5 motif on the non coding strand (5'-TGTTTGT3'-). The transcription start site is indicated by an arrow and labeled +1.

Comparison of the human SPB promoter proximal region to the corresponding murine sequence revealed uninterrupted conservation of 11 (TGGAGGGCTCT) (SEQ ID NO: 33) and 12 (CAAACACTGAGG) (SEQ ID NO: 34) nucleotides in the SPB-f1 and SPB-f2-binding sites, respectively. Much less conservation was found in regions protected by both H441 and HeLa cell nuclear extract. Only 4 of 16, 6 of 24, and 15 of 19 nucleotides were conserved in the SPB-f3-, SPB-f4- and SPB-f5-binding sites, respectively. Within SPB-f4, the murine sequence did not contain an Sp1 motif; however, a 7-bp TATA box element was conserved. Although an AP1-binding site motif was not identified within the murine sequence corresponding to SPB-f5 in exon 1, this motif was identified 7 bp downstream of the murine TATA box. Taken together, these experiments demonstrate that the SPB promoter proximal region contains five nuclear protein-binding sites, two of which bind novel lung cell-specific nuclear protein complexes. In particular, with the exception of the HNF-5 motif in SPB-f2, the sequence of the DNase I footprints specifically protected in H441 cells does not correspond to any known promoter or enhancer binding site motif and was conserved between the human and murine genes, suggesting that these elements represent novel lung cell-specific transcriptional regulatory pathways.

The above results demonstrate that lung cell-specific transcription of the SPB gene is dependent on a 259 bp promoter fragment from base −218 to base +41 of the SPB gene.

In order to identify putative distal regulatory elements, the DNase I hypersensitivity assay was exploited. (Gross, et al., *Ann.Rev.Biochem.*, Vol. 57, pgs. 159–197 (1988); Eissenberg, et al., *Ann.Rev.Genetics*, Vol. 19, pgs. 485–536 (1985)). This method has provided consistent correlation between the location of DNA regulatory elements, such as enhancers or silencers, and the occurrence of DNase I hypersensitive sites. (Gross, et al., 1988; Eissenberg, et al., 1985). The most striking finding in examining the DNase I hypersensitivity pattern of the SPB gene and 5'-flanking region was the cellular specificity of DH sites found close to or within the SPB promoter region and the lack of additional hypersensitivity within 5 kb of additional upstream sequence. Because those enhancers which have been examined are associated with DH sites (Gross, et al., 1988; Eissenberg, et al., 1985), this result suggested that sequence far upstream of DHI and DHII did not contain characteristic enhancer domains. In agreement with this finding, deletion of sequence between −2241 and −218 did not significantly alter the maximal transcriptional activity of the SPB promoter in transient expression assays. Taken together, these data demonstrate that sequences sufficient to direct lung cell-specific expression of SPB reside within the proximal promoter region.

DNase I footprint analysis of the human SPB promoter revealed five nuclear protein-binding sites between bp −102 and +32. The two 5'-most binding sites, SPB-f1 and SPB-f2, interacted with nuclear proteins present only in H441 cells, and deletion of these sites resulted in significant reduction in the transcriptional activity of the SPB promoter. With the exception of an HNF5 motif identified in SPB-f2, the sequence of SPB-f1 and SPB-f2 did not contain significant homology to more than 150 functional elements for vertebrate genes (Faisst, et al., *Nucleic Acids Res.*, Vol. 20, pgs. 3–26 (1992)).

A search of the 5'-flanking regions of genes that are expressed in the lung, including human and murine surfactant proteins A and C, and rat Clara cell secretory protein, did not reveal elements with significant homology to SPB-f1 or SPB-f2. However, it is possible that once important bases for binding are identified and/or transcriptional proteins are isolated or cloned, binding sites in these or other lung genes will become evident. Comparison of the human and murine SPB 5'-flanking sequence demonstrated that SPB-f1 and SPB-f2 were evolutionarily conserved in spite of sequence divergence outside of this region. The final indication that SPB-f1 and SPB-f2 are important to the lung cell specificity of SPB gene regulation was the low promoter activity in HeLa cells which lacked SPB-f1 and SPB-f2 binding activity but contained SPB-f3 to SPB-f5 binding activity.

The finding that SPB promoter region contains two evolutionarily conserved and previously undescribed nuclear protein-binding sites and that at least one of these sites is not related to any previously described lung regulatory region or to other consensus sites, strongly suggests the existence of novel lung cell-specific transcription factors. These results should facilitate studies designed to elucidate the mechanisms of cell type-specific gene expression within the lung.

Example 2

Identification of TTF-1 and HNF-3 Binding Sites in SPB Promoter Region

In Example 1, and in Bohinski, et al., 1993, a region of the human SP-B promoter was identified, which was protected specifically by lung cell nuclear proteins in DNase I footprinting experiments. Comparison to homologous sequences from the mouse SP-B gene promoter revealed two, 14 bp blocks of uninterrupted identity within these footprinted regions. (FIG. 7A). In FIG. 7A, vertical lines indicate identity between the mouse and human SP-B promoters, and dashes are gaps inserted for maximal alignment. The shaded regions are DNase I footprints determined in the study described in Bohinski, et al., 1993. The 55 bp region was used as a probe in electrophoretic mobility shift assays, and several specific and non-specific complexes were observed. Resolution of these complexes was simplified, and non-specific binding was reduced by designing sub-probes of this region based on the blocks of conserved sequences and DNase I protection. This resulted in two probes, designated SPB-f1 and SPB-f2, as shown as thick horizontal lines in FIG. 7A. In order to aid in the identification of important complexes, the evolutionary conservation of this region, and the idea that the cognate cell-type specific transcription factors would also be conserved, were exploited. In this example, electrophoretic mobility shift assays were conducted upon nuclear extracts from human H441 and mouse MLE-15 lung adenocarcinoma cell lines.

H441 and MLE-15 nuclear extracts were prepared using a 'mini-extract' procedure adapted from Schreiber et al., *Nucl. Acids Res.*, Vol. 17, pg. 6419 1989). All procedures for nuclear extraction were performed on ice with ice-cold reagents. Confluent monolayers from 1–4, 10-cm dishes were washed twice with 10 ml ice-cold phosphate buffered saline (PBS), harvested by scraping into 1 ml PBS and pelleted in a 1.5 ml microcentrifuge tube at 3,000 rpm for 5 min. The cell pellet was washed once in 1 ml PBS and pelleted as above. The pellet was resuspended in one packed cell volume of fresh Buffer A (10 mM HEPES, pH 7.9; 10 mM KCl; 0.1 mM EDTA; 1.5 mM $MgCl_2$; 0.2% v/v Nonidet P-40; 1 mM Dithiothreitol, DTT; 0.5 mM phenylmethylsulfonyl fluoride, PMSF), and cells were lysed during a 5 minute incubation with occasional gentle vortexing. A nuclear pellet was obtained by microcentrifugation at 3,000 rpm for 5 minutes, and the supernatant was the cytoplasmic extract. The nuclear pellet was resuspended in one packed nuclear volume of fresh Buffer B (20 mM HEPES, pH 7.9; 420 mM NaCl; 0.1 mM EDTA; 1.5 mM $MgCl_2$; 25% v/v glycerol; 1 mM DTT; 0.5 mM PMSF) and nuclei were extracted during a 10 minute incubation with occasional gentle vortexing. Extracted nuclei were pelleted in a microcentrifuge at 14,000 rpm for 10 minutes. The supernatant was recovered and typically contained 5.0–10.0 $\mu g\ \mu l^{-1}$ of extracted nuclear protein. Nuclear extracts were stored at −80° C. without loss of activity for at least six months.

For the electrophoretic mobility shift assays, oligonucleotides were annealed at 10 μM in 100 μl Buffer M (10 mM Tris pH 7.5; 10 mM $MgCl_2$; and 50 mM NaCl) by placing the mixture in a preheated 95° C. dry block which was then slowly cooled to room temperature. $A_{260}$ was determined and dilutions of this mixture were made in TE (10 mM Tris pH 8.0; 1 mM EDTA) and used directly in EMSA as unlabeled competitor DNA. For use as probe in EMSA 20 μl of the annealed mixture was gel purified using a 4% BIO-GEL and MERmaid kit as specified by the manufacturer (BIO 101). $A_{260}$ was determined and 1.5 pmol of annealed and gel-purified oligonucleotide were end-labeled using [$\gamma$-$^{32}$P]ATP and T4 polynucleotide kinase. End-labeled probe was purified from unincorporated [$\gamma$-$^{32}$P]ATP using a Pharmacia Nick Column and recovered in 400 μl TE for an activity of approximately 25,000 dpm/$\mu l^{-1}$.

The electrophoretic mobility shift assay (EMSA) was adapted from Hennighausen and Lubon, *Meth. Enzymol.*, Vol. 152, pgs. 727–735 (1987). Briefly, nuclear extract (1–2 μl) and, when indicated, unlabeled oligonucleotide competitor DNA were preincubated in 20 μl Buffer C (12 mM HEPES, pH 7.9; 4 mM Tris-Cl pH 7.9; 25 mM KCl; 5 mM MgCl$_2$; 1 mM EDTA; 1 mM DTT; 50 ng μl$^{-1}$ poly[d(I-C)], Boehringer Mannheim; 0.2 mM fresh PMSF) for 10 minutes on ice. Probe (100,000 dpm) was added and incubated an additional 20 minutes on ice. For antibody supershift and interference assays, 1 μl of antibody was added after the addition of probe and incubated an additional 20 minutes on ice. TTF-1 antibody is described in Lazzaro et al., *Development*, Vol. 113, pgs. 1093–1104 (1991). HNF-3α, β, and γ antibodies were kindly provided by Dr. J. E. Darnell, Jr. (Lai et al., *Genes and Devel.*, Vol. 5, pgs. 416–427 (1991)). Recombinant, bacterially expressed TTF-1 homeodomain protein (TTF-1 HD) is described in Guazzi et al., *EMBO J.*, Vol. 9, pgs. 3631–3639 (1990). Assays were performed using 1 μl TTF-1 HD in place of nuclear extract. Bound and free probe were resolved using non-denaturing polyacrylamide gel electrophoresis. 5% gels (acrylamide:bisacrylamide, 29:1, 0.5×TBE (44.5 mM Tris; 44.5 mM Borate; 1 mM EDTA; pH 8.3); 2.5% v/v glycerol; 1.5 mm thick) were run in 0.5×TBE running buffer at constant current (30 mA) for approximately 90 minutes. Gels were blotted to Whatman 3MM paper, dried under vacuum and exposed to X-ray film for 1–3 hours at –80° C. with an intensifying screen.

Figure 7B:
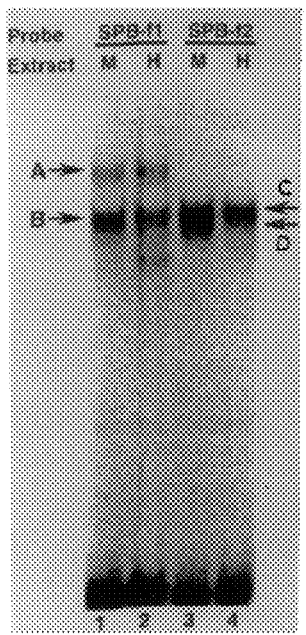
FIG. 7B is an EMSA blot of the binding of SPB-f1 and SPB-f2 to nuclear extracts of MLE-15 (M) and H441 (H) cells.
Figure 7C:
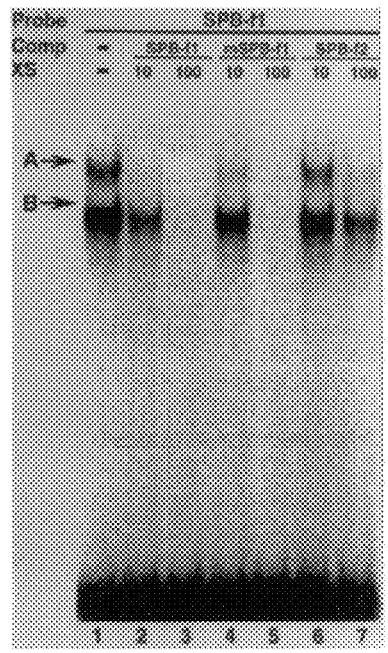
FIGS. 7C and 7D are EMSA blots in which unlabeled competitor probes were added to the EMSA reactions.
Figure 7D:
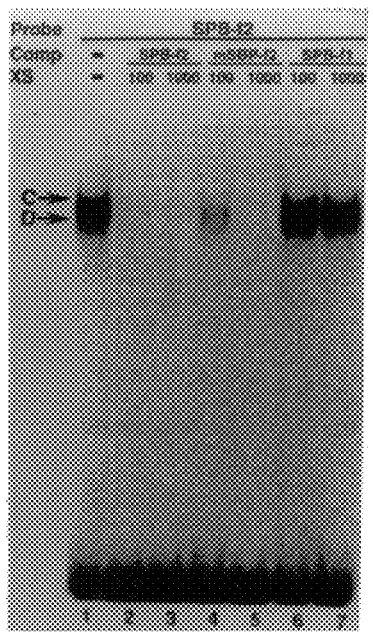

Nuclear extracts from both the H441 and MLE-15 cell lines formed two complexes of identical electrophoretic mobility with SPB-f1 (FIG. 7B, lanes 1 and 2, A and B arrows) and, similarly, one complex of identical electrophoretic mobility with SPB-f2 (FIG. 7B, lanes 3 and 4, C arrow). Complex D (FIG. 7B, lane 3, D arrow) resolved from Complex C by extended electrophoresis, and only appeared using MLE-15 nuclear extracts. A complex of low abundance and high mobility, apparent with H441 nuclear extract and SPB-f1 (FIG. 7B, lane 2), was not reproducible under these conditions. In order to identify Complex D as well as the conserved Complexes A, B, and C, MLE-15 nuclear extract was used for further study. The binding specificity of these complexes was determined by the addition of unlabeled competitor oligonucleotides, referred to in FIGS. 7C and 7D as Comp. Each competitor was added in the molar excesses shown in FIGS. 7C and 7D. This resulted in efficient competition for complexes A, B, C, and D by an excess of self (FIGS. 7C and 7D, lanes 2 and 3), the mouse homologue of self (FIGS. 7C and 7D, lanes 4 and 5), but not the respective adjacent binding site (FIGS. 7C and 7D, lanes 6 and 7). For SPB-f2, the human sequence appeared to be a better competitor than the mouse, but both were significantly more efficient competitors than the adjacent binding site SPB-f1. Because SPB-f1 and SPB-f2 did not cross compete in these assays, it was concluded that at least two distinct and evolutionarily conserved nuclear factors specifically bound this region.

SPB-f2 contained a TGT3 motif (TGTTTGC) (SEQ ID NO: 35) that occurs in the regulatory elements of diverse liver-specific genes (Jackson, et al., *Mol. Cell Biol.*, Vol. 13, pgs. 2401–2410 (1993)). Because of its apparent novelty, this motif also was termed HNF-5 to distinguish it from motifs recognized by other liver transcription factors, including HNF-3 (Grange, et al., *Nucleic Acids Research*, Vol. 19, pgs. 131–139 (1990); Rigaud, et al., *Cell*, Vol. 67, pgs. 977–986 (1990)). This motif binds HNF-3 proteins (Drewes, et al., *Nucleic Acids Research*, Vol. 19, pgs. 6383–6389 (1991); Jackson, et al., 1993; Nitsch, et al., *Genes & Devel.*, Vol. 7, pgs. 308–319 (1993); Pani, et al., *Mol. Cell. Biol.*, Vol. 12, pgs. 552–562 (1993)). SPB-f2 was not clearly related to the HNF-3 motif identified in the transthyretin (TTR) and α-1-antitrypsin liver-specific regulatory regions (FIG. 8A, Costa, et al., *Nucleic Acids Research*, Vol. 19, pgs. 4139–4145 (1989)). As shown in FIG. 8A, nucleotides that match SPB-f2 are shaded in the TGT3 and TTR-S oligos. TGT3 is oligo S4 (Grange, et al., 1990) from the tyrosine aminotransferase gene enhancer. TTR-S is oligo TTR-S from the TTR gene promoter. (Costa, et al., 1989). mTGT3 contains a 2 bp mutation that eliminates specific binding of HNF-3 and is the same as oligo S4 mut. (Grange, et al., 1990.) oligonucleotides representative of each HNF-3 motif were employed as unlabeled competitors in an electrophoretic mobility shift assay, and efficient cross competition between the motifs was found. As shown in FIG. 8B, unlabeled competitors were added to the EMSA assays at a 1,000-fold molar excess as compared to probe. A TGT3 site from the tyrosine aminotransferase gene enhancer (Grange, et al., 1990) or the strong HNF-3 site from the TTR gene promoter, TTR-S (Costa, et al., 1989), were efficient competitors for complexes C and D (FIG. 8B). A mutant TGT3 motif (mTGT3) which does not bind HNF-3 (Grange, et al., 1990) did not compete for complex C or D (FIG. 8B). Antisera to electrophoretic mobility shift assay reactions specific for each HNF-3 protein (anti-HNF-3α, β, and γ) (Lai, et al., 1991), were added, and the binding of both HNF-3α and HNF-3β to SPB-f2 was shown using MLE-15 nuclear extracts. H441 nuclear proteins formed only Complex C. The protein was determined to be HNF-3α. Anti-HNF-3α and anti-HNF-3β significantly interfered with the formation of Complex C and Complex D, respectively, and formed only minor supershifted complexes of lower mobility. (FIG. 8C, α and β asterisks). The identification of the lowest mobility complex as HNF-3α was consistent with the relative mobilities of HNF-3 proteins in liver cells where HNF-3β complexes migrate only slightly faster than HNF-3α and the two complexes appear as a single broad band in an electrophoretic mobility shift assay. (Lai, et al., 1991). Simultaneous addition of both anti-HNF-3α and anti-HNF-3β eliminated all major complex formation with SPB-f2, and indicated that other proteins did not independently bind this region (FIG. 8C, lane 5). These results were due to specific behavior of anti-HNF-3α and anti-HNF-3β because they did not significantly affect Complex A and Complex B (FIG. 8C, lanes 6 and 7), and supported the idea that factors bound to SPB-f1 were distinct. In addition, anti-HNF-3γ did not affect specifically major complex formation (FIG. 8, lane 4), consistent with its lack of expression in the lung (Lai, et al., 1991). These observations were supported using Northern blot analysis, and expression of HNF-3α and HNF-3β was detected in MLE-15 cells, and only HNF-3α in H441 cells.

An informative cis-active motif was not apparent in SPB-f1. In electrophoretic mobility shift assay (EMSA), Complex A appeared at high nuclear protein concentration, and was eliminated before Complex B by unlabeled self-competitor (data not shown). This suggested that two factors might bind SPB-f1 independently to form a trimeric protein-DNA complex. This hypothesis was tested by using 5' (5'f1) or 3' (3'f1) sub-fragments of SPB-f1 as competitors and probes in EMSA (FIGS. 9A and 9B). The sub-fragments were extended 4 bp beyond SPB-f1 in this region to prevent the oligonucleotide from being too small for EMSA. Unlabeled competitors were added to the EMSA reactions at a 100-fold molar excess compared to probe. The 5' and 3' sub-fragments of SPB-f1 were specific and equivalent competitors for Complex A and Complex B, but slightly less efficient than the parent fragment (FIG. 9B, lanes 1–5), and this agreed with the idea that each sub-fragment had only half the number of binding sites as compared with the parent. When labeled and used as a probe, the two sub-fragments formed complexes of identical mobility as compared to each other, but different from either Complex A or Complex B (FIG. 9B, lanes 6 and 7). This could be due to the binding of a factor which induces a DNA bend closed to the center of each sub-fragment, but closer to each end of the parent fragment. When such a factor binds to the center of a DNA molecule, its migration is more retarded in polyacrylamide matrices than when bound to the end of the DNA molecule (Wu, Nature, Vol. 308, pgs. 509–513, (1984)). The idea that the same factor bound to each end of SPB-f1 prompted a detailed self to self comparison of these sequences. Maximal alignment of 5'f1 and 3'f1 showed less than 50% identity, but revealed a short, conserved inverted palindrome motif, CTNNAG (FIG. 10A). The first two lines of FIG. 10A show this maximal alignment. The two CTNNAG motifs were spaced exactly 10 base pairs from their center point within SPB-f1 and were part of larger but distinct inverted palindromes (FIG. 10A). A consensus (also known as SPB-f1 con) from this alignment was determined (FIG. 10A), and was compared manually to a list of cis-active motifs for vertebrate-encoded transcription factors (Faisst, et al., *Nucleic Acids Res., Vol.* 20, pgs. 3–26 (1992)) with emphasis on the CTNNAG motif. The SPB-f1 con sequence is shown in line 3 of FIG. 10A, and compared with the reported TTF-1 consensus, shown in line 4 of FIG. 10A. The sequence of the strong TTF-1 binding site from the thyroglobulin gene promoter, oligo C, is shown in line 5 of FIG. 10A. FIG. 10B depicts the organization of CTNNAG motifs (shaded) within SPB-f1. Each motif is embedded in a larger inverted palindrome indicated above and below the sequence by opposing arrows, and labeled PAL I and PAL II. The motifs are separated by exactly 10 bp from their centers of dyad symmetry. Several motifs shared the CTNNAG core; however, the limited identity to the TTF-1 binding site was found to be the most attractive because this factor is expressed in the developing lung epithelium (Lazzaro, et al., 1991). Using the same strategy as hereinabove described for the identification of the HNF-3 binding sites, it was found that a high affinity binding site for TTF-1 from the thyroid-specific thyroglobulin promoter, oligo C (Civitareale, et al., *EMBO J.*, Vol. 8, pgs. 2537–2542 (1989)) was a more efficient competitor for Complex A and Complex B than self. (FIG. 10C, lanes 2–4). In the experiment in which the results are shown in FIG. 10C, unlabeled competitors were added at a 100-fold molar excess as compared to probe. When used as a probe, oligo C formed a complex of identical mobility to Complex B, consistent with the single TTF-1 binding site in this oligo (FIG. 10C, lanes 1 and 2). Oligo C, however, diverges from the consensus and does not contain a perfect CTNNAG motif. (FIG. 10A). This favored recognition of the defined TTF-1 binding site in oligo C as opposed to circumstantial recognition of a CTNNAG motif. Affinity purified, polyclonal antisera to TTF-1 in EMSA reactions (anti TTF-1, Lazzaro, et al., 1991) was employed, and binding of TTF-1 to two independent sites in SPB-f1 was shown. Addition of anti-TTF-1 to EMSA reactions containing either MLE-15 or H441 nuclear proteins resulted in the elimination of Complex A and Complex B, and the formation of a lower mobility complex of similar abundance (FIG. 10D, lanes 1 and 2, and data not shown). This reaction was specific because anti-TTF-1 did not alter HNF-3 and SPB-f2 complex formation (FIG. 10D, lanes 3 and 4). For lanes 5–8 of FIG. 10D, unlabeled competitors were added to the EMSA reaction at a 100-fold molar excess as compared to probe. Further, a recombinant fragment of TTF-1 containing the homeodomain (TTF-1, HD, Guazzi, et al., 1990) specifically bound to SPB-f1 and formed a two-banded pattern (A' and B' in FIG. 10D, lanes 5–8). Complex A' formed at higher protein concentrations and depended on the integrity of both CTNNAG motifs in SPB-f1 (FIG. 11C). As will be explained hereinbelow, disruption of either CTNNAG core motif resulted in complete loss of Complex A' and a reduction in Complex B' (FIG. 11C, lanes 2 and 3). Disruption of both sites completely eliminated formation of a specific complex (FIG. 11C, lane 4). The binding of recombinant TTF-1 HD to either site alone formed complexes of slightly different mobility which were evident only when the other site was mutated.

FIG. 11A depicts the relative location and identity of TTF-1 and HNF-3 binding sites which have been identified. Line one in FIG. 11A shows the locations of TTF-1 and HNF-3 binding sites identified in the SP-B promoter. Mutations at each site then were constructed, and binding was shown to be dependent upon a specific sequence because a 2 bp mutation at each site severely impaired factor binding in EMSA experiments. The shaded nucleotides in line two indicate the 2 bp mutations that were made at each binding site.

Plasmids containing mutated TTF-1 and HNF-3 binding sites were constructed as follows:

The human surfactant protein B gene promoter (bp −218 to 44) was isolated from p2244/436 (Bohinski et al., 1993) (FIG. 12) using PCR and linker primers to create 5' HindIII and 3' SalI sites. The product was digested with HindIII and SalI and cloned into the respective sites of M13mp-18 (Gibco-BRL, catalog no. 18227-017) and used as template for site directed mutagenesis performed by the method of Kunkel, *Proc. Nat. Acad. Sci.*, USA, Vol. 82, pgs. 488–492 (1985). The wild type and mutated promoters were isolated from M13 replicative form by HindIII and SalI digestion and cloned into the respective sites of pBLCAT6 (Boshart, et al., *Gene*, Vol. 110, pgs. 129–130 (1992)). (FIG. 13) These SPB promoter-CAT plasmids were designated p218/41-WT (FIG. 14), -5T, -3T, -TT, -H, or -TTH, and identities were confirmed dideoxy sequencing of double stranded templates. Plasmid p128/41-WT contains no mutations in the human surfactant protein B gene promoter region. Plasmid p218/41-5T contains a mutation in the 5' TTF-1 binding site in the region from bp−118 to bp−64 of the human surfactant protein B gene promoter region. Plasmid p218/41-3T contains a mutation in the 3' TTF-1 binding site in the region from bp−118 to bp−64 of the human surfactant protein B gene promoter region. Plasmid p218/41-TT contains mutations in the 5' TTF-1 binding site and in the 3' TTF-1 binding site in the region from bp−118 to bp−64 of the human surfactant protein B gene promoter region. Plasmid p218-41-H contains a mutation in the HNF-3 binding site in the region from bp−118 to bp−64 of the human surfactant protein B gene promoter region. Plasmid p218/41-TTH contains mutations in the 5' TTF-1 binding site, the 3' TTF-1 binding site, and the HNF-3 binding site in the region from bp−118 to bp−64 of the human surfactant protein B gene promoter region. The 5' deletion mutant pΔ−80 contains human SPB (bp −80 to 41) in the HindIII and SalI sites of pBLCAT6 (FIG. 13) and was made using PCR and linker primers as above. The rat CCSP gene promoter (bp −2338 to 49) was cloned into the polylinker of pBLCAT6 (FIG. 13) as described in Stripp, et al., *Genomics*, Vol. 20, pgs. 27–35 (1994) and was kindly provided by Dr. B. R. Stripp. The mouse SPC gene promoter (bp −4680 to 18) was isolated as an XbaI and HpaII fragment, digested with nuclease Bal31 at its 3' end, repaired with T4 DNA polymerase to bp 18, and cloned as an XbaI and 3' XhoI-linked fragment into the respective sites of pBLCAT6 (FIG. 13). pBLCATS contains the thymidine kinase promoter (bp −105 to 51) (Boshart, et al., 1992). TTR-CAT contains the mouse transthyretin promoter (bp −202 to 9) and was kindly provided by Dr. J. E. Darnell, Jr. (Lai, et al., 1991).

NCI-H441-4 (H441) and MLE-15 cells (used in nuclear extract procedure) were maintained exactly as described in O'Reilly, et al., 1988 and Wikenheiser, et al., Proc. Nat. Acad. Sci., Vol. 901, pgs. 11029–11033 (1993). HeLa cells were maintained in Dulbecco's Modified Eagle Medium containing 10% heat inactivated fetal bovine serum. The day before transfection confluent monolayers were split (1:5–1:8 for H441 cells; 1:20 for HeLa cells) into 10-cm dishes. Four hours before transfection cells were switched to transfection medium (Dulbecco's Modified Eagle Medium containing 10% heat inactivated fetal bovine serum and 1% penicillin-streptomycin, Gibco BRL). Transfections were performed using the calcium phosphate coprecipitation method essentially as described (Rosenthal, Meth. Enzymol., Vol. 152, pgs. 704–720 (1987)) except glycerol shock was not used. For the analysis of point mutants in H441 cells precipitates were prepared using 5.0 pmol of promoter-CAT fusion plasmid and 2.5 pmol of the internal control plasmid, pCMV-βgal, (MacGregor, et al., Nucleic Acids Res., Vol. 6, pg. 2365 (1989)) per 10-cm dish. Precipitates were added dropwise to the medium covering the cells. The cells were incubated with precipitate for 14–18 hours, washed once with calcium and magnesium free Hanks' Balanced Salt Solution, returned to maintenance medium and cultured for an additional 24 hours. Cells were harvested and freeze-thaw lysates were prepared in 100 μl of 0.25M Tris, pH7.8, and aliquots assayed for CAT activity and β-galactosidase activity as described in Rosenthal (1987) and MacGregor, et al., Methods in Molecular Biology, Murray, ed., Vol. 7, pgs. 217–235, Humana Press, Clifton, N.J. (1991). To correct for variations in transfection efficiency, lysates were normalized for β-galactosidase activity that CAT enzyme assays contained equivalent amounts of β-galactosidase activity. Thin layer chromatograms of $^{14}$C-chloramphenicol and its acetylated derivatives were quantitated using a Molecular Dynamics Phosphor Imager.

The results of the transfection experiments were as follows. The mutated version of SPB-f2 (H) did not compete for or bind HNF-3 proteins (FIG. 11D), and, as discussed above, TTF-1 binding depended upon the integrity of the CTNNAG motif. (FIG. 11C). For the experiments in which the results are shown in FIG. 11C, 1 μl of TTF-1 HD was used in place of nuclear extract, and incubated with the wild type SPB-f1 probe (f1) or, with one of the mutant probes 5T, 3T, or TT in EMSA assays. For the experiments in which the results are shown in FIG. 11D, the wild type SPB-f2 probe was compared to the mutant probe H in an EMSA assay using MLE-15 nuclear extract. Unlabeled competitors were added at a 1,000-fold molar excess compared to probe. In order to determine if these sites were transcriptionally active, site-directed mutagenesis was used to construct these binding site mutations in the SPB gene promoter. As hereinabove described, the wild type (WT) and mutant promoters were linked to a CAT reporter gene and assayed for transcriptional activity in H441 and HeLa cells. (FIG. 11B). For the wild type promoter, CAT activity equals 1.00. The results shown are average values from 3 independent experiments where the standard error of the mean was less than 10%. All mutations resulted in a statistically significant reduction in CAT activity in H441 cells, and no mutation affected activity in HeLa cells, thus demonstrating the restricted cellular activity of factors bound to this region. Mutation of the 5' TTF-1 binding site (5T) was less dramatic than mutation of the 3' TTF-1 binding site (3T), and mutation of both TTF-1 sites (TT) was no different than for the 3T mutation, suggesting that the 5' site depended on the 3' site for activity. Mutation of all three binding sites (TTH) resulted in an activity that was not different from gross deletion of all sequences upstream of −80 (Δ−80). This indicated that no other sites were present between −218 and −80 or that no other site in this region could affect SPB promoter function in the absence of the defined TTF-1 and HNF-3 sites. Although each site demonstrated transcriptional activity, complementary HNF-3 (H) and TTF-1 (TT) mutations accounted for only 41% of wild type activity. Thus, it is concluded that TTF-1 and HNF-3 proteins synergistically activate SPB promoter function from this region.

It was then reasoned that TTF-1 would function as a binding site depending transactivator of SPB and other target promoters, and the SPB promoter and binding site mutants were employed to develop an assay for the DNA-binding and transcriptional activating function of TTF-1. HeLa cells were transfected with plasmids containing wild-type or mutant SPB promoters, and either the empty vector pRc/CMV (Invitrogen) or an vector containing the entire TTF-1 open reading frame (pCMV-TTF-1) (Francis-Lang, et al., Mol. Cell Biol., Vol. 12, pgs. 576–588 (1992)). For the TTF-1 transactivation experiments in HeLa cells each 10 cm dish was treated with a precipitate prepared using 15.0 μg promoter-CAT fusion plasmid, 2.0 μg pCMV-βgal, 7.5 μg pUC19, and 0.5 μg of either the empty vector pRc/CMV (Invitrogen), or the pCMV-TTF-1 vector containing the entire TTF-1 open reading frame. Precipitates were added dropwise to the medium covering the cells. Cells were incubated with precipitate for 14–18 hours, washed once with calcium and magnesium from Hanks' Balanced Salt Solution, returned to maintenance medium, and cultured for an additional 48 hours. Cells were harvested and freeze-thaw lysates were prepared in 100 μl 0.25 M Tris, pH 7.8, and aliquots were assayed for CAT and β-galactosidase activity essentially as described in Rosenthal (1987) and MacGregor, et al. (1991). In order to correct for variations in transfection efficiency, lysates were normalized for β-galactosidase activity so that CAT enzyme assays contained equivalent amounts of β-galactosidase activity. Thin layer chromatograms of $^{14}$C-chloramphenicol and its acetylated derivatives were quantitated using a Molecular Dynamics Phosphor Imager. For the experiments in which the results are shown in FIG. 15A, the wild type (WT), TT, or H SPB promoter constructs were co-transfected transiently with the internal control plasmid pCMVβ-gal and either the empty vector (−), or vector containing the full length TTF-1 cDNA (+), into the HeLa cell line. Each (+) or (−) determination is representative of three independent experiments that were normalized from β-galactosidase. For the experiments in which the results are shown in FIG. 15B, CCSP, SPC, TTR, or TK promoter constructs were co-transfected (−) or (+) into the HeLa cell line as hereinabove described, and each determination is representative of three independent experiments. As shown in FIG. 15A, TTF-1 dramatically increased activity from the wild-type SPB promoter (FIG. 15A, lanes 1 and 2), but had no effect on the TTF-1 mutant promoter (FIG. 15A, lanes 3 and 4). Co-transfected TTF-1 also strongly activated the HNF-3 mutant promoter (FIG. 15A, lanes 5 and 6). Because TTF-1 transactivation was dependent strictly on the integrity of TTF-1 binding sites, these results demonstrated further a direct effect of TTF-1 on SPB promoter activity. This system then was employed to demonstrate the transcriptional response of other lung-specific promoters to TTF-1. TTF-1 dramatically increased the activity of the lung-specific CCSP and SPC gene promoters, but had no effect on the liver-specific TTR or the constitutive thymidine kinase (TK) gene promoters (FIG. 15B).

Example 3

Construction of an Adenoviral Vector for Lung Surfactant Gene Therapy Which Expresses the Surfactant Protein B Gene and Utilizes the Cognate Surfactant Protein B Gene Promoter The purpose of developing this vector for gene therapy for human surfactant protein deficiency states is to improve upon existing adenoviral vectors including DNA encoding human surfactant protein B. One current vector, AvSPB1 (disclosed in U.S. patent application Ser. No. 08/044,406, filed Apr. 8, 1993, now abandoned, incorporated herein by reference), expresses human surfactant protein B under control of the Rous Sarcoma Virus (RSV) long terminal repeat. This expression, however, is constitutive and not regulated by the usual transcriptional signals which modulate the endogenous SP-B gene in health and disease. The new vector Av1SPB2 (FIG. 22), the construction of which is described hereinbelow, is designed to express the human surfactant protein B gene under the control of its cognate human surfactant protein B gene promoter. This will allow for lung specific gene expression, and further, will allow for correct regulation of the gene after transfer into the patient's lung cells.

A similar vector, Av1SPB3 (FIG. 22), the construction of which is described hereinbelow, is designed to express the human surfactant protein B gene under the control of the murine surfactant protein B gene promoter. Construction of this vector allows evaluations to be carried out in a murine model to verify the tissue-specificity in an animal model prior to evaluations of the cognate human promoter-structural SPB gene in human clinical trials of SPB deficiency states.

A. Construction of pAVS6

The adenoviral construction shuttle plasmid pAvS6 was constructed in several steps using standard cloning techniques including polymerase chain reaction based cloning techniques. First, the 2913 bp BglII, HindIII fragment was removed from Ad-dl327 and inserted as a blunt fragment into the XhoI site of pBluescrpt II KS-(Stratagene, La Jolla, Calif.) (FIG. 16).

Ad-dl327 (Thimmappaya, et al., Cell, Vol. 31, pg. 543 (1983)) is identical to adenovirus 5 except that an XbaI fragment including bases 28591 to 30474 (or map units 78.5 to 84.7) of the Adenovirus 5 genome, and which is located in the E3 region, has been deleted. The complete Adenovirus 5 genome is registered as Genbank accession #M73260, incorporated herein by reference, and the virus is available from the American Type Culture Collection, Rockville, Md., U.S.A. under accession number VR-5.

Ad-dl327 was constructed by routine methods from Adenovirus 5 (Ad5). The method is outlined briefly as follows and previously described by Jones and Shenk, Cell 13:181–188 (1978). Ad5 DNA is isolated by proteolytic digestion of the virion and partially cleaved with Xba 1 restriction endonuclease. The Xba 1 fragments are then reassembled by ligation as a mixture of fragments. This results in some ligated genomes with a sequence similar to Ad5, except excluding sequences 28593 bp to 30470 bp. This DNA is then transfected into suitable cells (e.g. KB cells, HeLa cells, 293 cells) and overlaid with soft agar to allow plaque formation. Individual plaques are then isolated, amplified, and screened for the absence of the 1878 bp E3 region Xba 1 fragment.

The orientation of this fragment was such that the BglII site was nearest the T7 RNA polymerase site of pBluescript II KS. This plasmid was designated pHR. (FIG. 16).

Second, the ITR, encapsidation signal, Rous Sarcoma Virus promoter, the adenoviral tripartite leader (TPL) sequence and linking sequences were assembled as a block using PCR amplification (FIG. 17). The ITR and encapsidation signal (sequences 1–392 of Ad-dl327 [identical to sequences from Ad5, Genbank accession #M73260] incorporated herein by reference) were amplified (amplification 1) together from Ad-dl327 using primers containing NotI or AscI restriction sites. The Rous Sarcoma Virus LTR promoter was amplified (amplification 2) from the plasmid pRC/RSV (sequences 209 to 605; Invitrogen, San Diego, Calif.) using primers containing an AscI site and an SfiI site. DNA products from amplifications 1 and 2 were joined using the "overlap" PCR method (amplification 3) (Horton, et al., BioTechniques, 8:528–535 (1990)) with only the NotI primer and the SfiI primer. Complementarity between the AscI containing end of each initial DNA amplification product from reactions 1 and 2 allowed joining of these two pieces during amplification. Next the TPL was amplified (amplification 4) (sequences 6049 to 9730 of Ad-dl327 [identical to similar sequences from Ad5, Genbank accession #M73260]) from cDNA made from mRNA isolated from 293 cells (ATCC Accession No. CRL 1573) infected for 16 hrs. with Ad-dl327 using primers containing SfiI and XbaI sites respectively. DNA fragments from amplification reactions 3 and 4 were then joined using PCR (amplification 5) with the NotI and XbaI primers, thus creating the complete gene block.

Third, the ITR-encapsidation signal-TPL fragment was then purified, cleaved with NotI and XbaI and inserted into the NotI, XbaI cleaved pHR plasmid. This plasmid was designated pAvS6A⁻ and the orientation was such that the NotI site of the fragment was next to the T7 RNA polymerase site (FIG. 18).

Fourth, the SV40 early polyA signal was removed from SV40 DNA as an HpaI-BamHI fragment, treated with T4 DNA polymerase and inserted into the SalI site of the plasmid pAvS6A- (FIG. 18) to create pAvS6 (FIGS. 18 and 19).

The vectors Av1SPB2 and Av1SPB3 then are constructed as follows. First, the region of SP-B promoter which contains the essential SP-B regulatory elements (bp−439 to bp +41; Bohinski, et al., 1993) are cloned into the promoter position in pAvS6 (FIG. 19) in place of the RSV promoter which is first removed, by standard PCR cloning methods. The murine SPB promoter was cloned by using the following 5' and 3' primers:

```
Murine SPB5':5'-TGGACAGGCGCGCC CGGCACTTACCC TGCGTCAAGAGCCAGGAAGG-3'        (SEQ ID NO.:36)
                     AscI Murine SPB3':5'-CGTCATGGCCATATGGGCC TAGCCACTGCAG TAGGTGCGACTTGGCCATGG-3'   (SEQ ID NO.:37)
                      SfiI
```

The human SPB promoter was cloned by using the following 5' and 3' primers:

```
Human SPB5':5'-TGGACAGGCGCGCC CAGGGCTTGCCCTGG GTTAAGAGCCAGGCAGG-3'         (SEQ ID NO.:38)
                    AscI Human SPB3':5'-CGTCATGGCCATATGGGCC CAGCCACTGCAG CAGGTGTGACTCAGCCATGG-3'    (SEQ ID NO.:39)
                     SfiI
```

Second, after PCR amplification of the correct region from the SPB promoter containing plasmid (PMSPB (murine) (FIG. 20); pHSPB (human) (FIG. 21)), the PCR product is cloned into a minimal promoter expression plasmid containing the critical left end viral elements used in the adenovirus vector construction shuttle plasmid pAvS6. (FIG. 19).

The resulting plasmid vector contains the following sequential elements: the Ad5 left inverted terminal repeat (ITR), the encapsidation signal sequence, the SPB promoter element (from −439 bp to +44 bp for the human promoter, or from −382 bp to +41 bp for the murine promoter) followed by the remainder of pAvS6 (FIG. 19).

Third, this plasmid is linearized at the EcoRV site, the human SP-B gene is inserted so that the 5' end of the coding strand is closest to the promoter element. This plasmid then is linearized and co-transfected with the large fragment of Ad dl327 in 293 cells to generate the final adenoviral vector shown in FIG. 22.

The SP-B-adenoviral vector is formulated for aerosol instillation or for direct tracheal or intravascular injection by diluting the vector to approximately $10^6$–$10^{12}$ pfu per ml in normal saline and delivering (0.5–5 ml) of this solution by the chosen route; whether intravenous, intracheal, or aerosol. If plasmid vectors are utilized, approximately 1–2 mg of plasmid DNA is mixed with cationic lipids; for example, DOTMA Lipofectin or Lipofectamine in approximate ratios of 1:10 to 1:100 and delivered intratracheally by bronchoscope or vascularly, intravenously or by aerosol administration.

The efficacy and lung cell specificity of the lung specific vector can be assessed in vitro and in vivo. In vitro, H441-4 cells (human bronchiolar adenocarcinoma cells that express endogenous human SP-A and SP-B) are transfected with viral or plasmid constructs driven by the SP-B promoter element (or chimeric element containing TTF-1 and/or HNF-3 α and β binding sites). Approximately 24–48 hours after transfection, expression of the chimeric gene is assessed by RNA analysis (S1, RT-PCR, or Northern blots), by the synthesis and secretion of the gene products which are assessed by ELISA, Western blot, immunocytochemistry or by biological assays, or by immunoprecipitation of $^{35}S$ cysteine/methionine labeled proteins assessed by autoradiography after SDS-PAGE of either media or cell lysates obtained from the transfected cells. In one embodiment, H441-4 cells and control HeLa cells (which normally do not express human surfactant protein B) are transfected with the viral or plasmid constructs hereinabove described, and evaluated for expression as described in Bohinski, et al., *J. Biol. Chem.*, Vol. 268, pgs. 11160–11166 (1993). Cell specificity of the chimeric SP-B promoter driven transgene is assessed by transfection of non-lung cells, such as 3T3 fibroblasts, HeLa, CHO, or other appropriate mammalian cell systems.

To test the efficacy of and specificity of the SP-B driven constructs, the recombinant virus is instilled intratracheally, via tracheal cannulae or by aerosolization or by direct injection in 50 μl of diluent containing $1\times10^8$–$1\times10^{11}$ pfu per ml of the adenovirus, administered into the trachea of rodent or other mammalian models, such as mice, Cotton rats or hamsters. Larger volumes are utilized for larger animals, depending on the expected sites of delivery. After 24–72 hours, lungs are excised, the transfer of the gene assessed by measuring the recombinant protein in lavage, or lung homogenates, by ELISA, Western blot, or by biological assay. organ specificity can be assessed readily by RNA analysis (S1 nuclease, RT-PCR, Northern blot or by in situ hybridization). Alternatively, immunocytochemistry, comparing lung and other tissues is utilized to assess the specificity and abundance of expression of the chimeric gene. Constructs expressing in a lung epithelial cell-specific or selective manner and providing appropriate abundance of gene transcripts, which are likely to result in genetic correction of the metabolic defect targeted by the vector, are utilized for clinical testing and use.

In one embodiment, Av1SPB3 is administered in vivo to the lungs of mice, followed by in situ hybridization of sense (control) and antisense (SPB specific) cRNA probes to lung tissue as described in Yei, et al., *Am. J. Cell. and Molec. Biol.*, (in press).

Example 4

Identification of TTF-1 Binding Sites in Murine Surfactant Protein A (SP-A) Gene Plasmid Constructions and Site-directed Mutagenesis-5' Flanking sequences of the mouse SP-A gene (base pairs −255 to +45) were isolated from pCPA-1.4 (Korfhagen, et al., *Am. J. Physiol.*, Vol. 263, pgs. L546–L554 (1992)) using polymerase chain reactions and linker primers to create a 5'-HindIII and 3'-PstI sites. The product was digested with HindIII and PstI and cloned into pCPA-0 to generate pCPA-0.3. To generate the TTF-1 site mutants, the pCPA-0.3 was used as template for the polymerase chain reactions. Oligomers were made to each of the three TTF-1 binding sites, replacing each with a restriction enzyme sequence. The TTF-1 site located at position −223 to −218 was changed to a SalI site, the site located at −200 to −195 was changed to a NcoI site, and the TTF-1 site at position −190 to −185 was changed to a BamHI restriction site. These oligomers were then used in polymerase chain reactions with pCPA-0.3 as template and linker primers used to generate the wild-type sequences. The products were then digested with appropriate endonucleases and cloned into pCPA-0. These SP-A promoter-chloramphenicol acetyltransferase (CAT) fusion plasmids were designated pCPA-0.3T-1,3, pCPA-0.3T-3, and pCPA-0.3T-3,4 and their identities were confirmed by dideoxy sequencing of M13 mp19 templates. The sequence originally published for the 5'-flanking sequence was incorrect at position −4. There is no C in that position. Therefore, all sequences in this example differ by −1 from the published sequences. (Korfhagen, et al., 1992).

Cell Culture, Transfection, and Reporter Gene Assays—Cells were cultured and transfection experiments were performed essentially as previously described (Bohinski, et al., *Mol. Cell. Biol.*, Vol. 14, pgs. 5671–5681 (1994)). MLE-15 cells were derived from lung tumors produced in transgenic mice expressing SV40 large T antigen (SV40 TAg) driven by the lung-specific human SP-C promoter (Wikenheiser, et al., *Proc. Nat. Acad. Sci.*, Vol. 90, pgs. 11029–11033 (1993)). MLE-15 is a clonal cell line expressing SP-A, SP-B, and SP-C. For TTF-1 transactivation experiments with HeLa cells, 10-cm dishes were treated with precipitates prepared by using 7.5 pmol of promoter-CAT fusion plasmid, 4 pmol of pCMV-βgal, and 1 pmol of either the empty expression vector (pRc/CMV) (Invitrogen), which includes a CMV promoter, a multiple cloning site and a neomycin resistance gene, or an expression vector containing the entire TTF-1 open reading frame (pCMV/TTF-1) as previously described (Bohinski, et al., 1994). Cell lysates were assayed for β-galactosidase and CAT activities. To minimize variability, cells used for each construct were plated at the same density, transfected, and harvested at the same time.

Nuclear Extract Preparation—MLE-15 nuclear extracts were prepared by using a modified extract procedure as described by Bohinski et al., 1994. Nuclear extraction was performed at +4° C. or on ice with ice-cold reagents. Confluent monolayers from six 10-cm-diameter dishes were washed twice with 10 ml of ice-cold phosphate-buffered saline (pH 7.2) and harvested by scraping into 1 ml of phosphate-buffered saline. Cells were pelleted in a chilled 1.5-ml microcentrifuge tube at 3000 rpm for 5 min. The pellet was washed once in phosphate-buffered saline and repelleted as described above. The cell pellet was resuspended in 1 cell volume of fresh (lysis) buffer A (10 mM Hepes, pH 7.9, 10 mM KCl, 0.1 mM EDTA, 1.5 MM $MgCl_2$, 0.2% (v/v) Nonidet P-40, 1 mM dithiothreitol, 0.5 mM phenylmethylsulfonyl fluoride). Cells were lysed in this buffer during a 5-min incubation with occasional vortexing. The nuclear pellet was obtained by centrifugation at 3000 rpm for 5 min and was resuspended in 1 volume of fresh (extract) buffer B (20 mM Hepes (pH 7.9), 420 mM NaCl, 0.1 mM EDTA, 1.5 mM $MgCl_2$, 25% (v/v) glycerol, 1 mM dithiothreitol, 0.5 mM phenylmethylsulfonyl fluoride). Nuclei were extracted during a 10-min incubation with occasional gentle vortexing. Extracted nuclei were pelleted by centrifugation at 14,000 rpm for 10 min. The supernatant was saved as the extracted nuclear protein. Extracts typically contained 5.0–10.0 µg of nuclear protein per µl. Nuclear extracts were quick frozen and stored at −80° C.

Synthetic oligonucleotides—Single-stranded oligonucleotides were synthesized on an ABI oligonucleotide synthesizer by the Oligonucleotide Synthesis Core Facility, Children's Hospital Medical Center. Single-stranded oligonucleotides were annealed at 10 µM in 100 µl annealing buffer M (10 mM Tris (pH 7.5), 10 mM $MgCl_2$, 50 mM NaCl) in a 95° C. dry heat block and then slowly cooled to room temperature. The absorbance of 260 nm ($A_{260}$) was determined, and dilutions of this mixture were made in TE (10 mM Tris (pH 8.0), 1 mM EDTA). These double-stranded oligomers were either used directly as cold competitors in an electrophoretic mobility shift assay (EMSA) or gel purified for labeling. For use as a probe in the EMSA, 20 µl of the annealed oligomer was gel purified using a 4% Biogel and a MERmaid kit as specified by the manufacturer (Bio 101, Inc.). The $A_{260}$ was determined, and 1.5 pmol of annealed and gel-purified oligonucleotide was end labeled using [$\gamma^{32}$P]ATP and T4 polynucleotide kinase. End-labeled probe was purified from unincorporated nucleotide by using a Pharmacia nick column and recovered in 400 µl of TE.

EMSA—Nuclear extracts (5.0–10.0 µg of protein) and unlabeled oligonucleotide competitors were preincubated in 12.5 µl of buffer containing 12 mM Hepes (pH 7.9), 4 mM Tris-Cl (pH 7.9), 50 mM KCl, 5 mM $MgCl_2$, 1 mM EDTA, 1 mM dithiothreitol, 75 ng/µl poly(dI-dC) (Boehringer Mannheim), 0.2 mM phenylmethylsulfonyl fluoride for 10 min on ice. Radiolabeled oligonucleotide or DNA fragments were added to the mixture and incubated an additional 20 min. on ice. For antibody supershift assays, 1 µl of TTF-1 antibody was added following addition of the nuclear extract and incubated as above. The TTF-1 antibody was previously described by Lazzaro et al., *Development*, Vol. 113, pgs. 1093–1104 (1991). Recombinant TTF-1 homeodomain protein (TTF-1 HD) was expressed in *Escherichia coli* and used as described by Damante and Di Lauro, *Proc. Nat. Acad. Sci.*, Vol. 88, pgs. 5388–5392 (1991). Assays were performed with 1 µl of TTF-1 HD in place of nuclear extract. The protein-DNA complexes were resolved from free probe by nondenaturing polyacrylamide gel electrophoresis with 5% gels (29:1, acrylamide/bisacrylamide; 0.5×TBE (44.55 mM Tris, 44.5 mM borate, 1 mM EDTA, pH 8.3); 2.5% (v/v) glycerol; 1.5 mm thick) were electrophoresed in 0.5×TBE buffer at constant current (30 mA) for approximately 90 min. Gels were blotted to Whatman 3MM paper, dried under vacuum, and exposed to x-ray film for 1 h at −80° C. with an intensifying screen.

Cell-specific Activity of SP-A Gene Constructs in Murine Lung Epithelial Cells (MLE-15 Cells)—SP-A is expressed specifically in the distal pulmonary epithelium. To determine sequences controlling SP-A gene expression, MLE-15, 3T3, H441, and HeLa cells were transfected with plasmids containing murine SP-A flanking sequences and the bacterial reporter gene, CAT. (FIG. 23) As shown in FIG. 23, to the left, the 5'-flanking region and portion of exon 1 of the mouse surfactant protein A (SP-A) gene are depicted. Potential binding sites for TTF-1 or hepatocyte nuclear factor-5 (HNF-5) are depicted above the line. Nucleotide positions are depicted below the line, and cat indicates the position of the chloramphenicol transferase gene. To the right of each clone, CAT activity is plotted relative to the promoterless plasmid, pCPA-O. The transfection data are representative of at least five separate transfections for MLE-15 and 3T3, and two experiments for HeLa and H441. Presented data were calculated from two experiments with triplicate samples for each constrct (n=6). Values represent mean±standard error. The values of pCPA 1.4 and pCPA 0.3 in HeLa or H441-4 cells were less than for pCPA-O and therefore are not distinguished in the graph.

MLE-15 cells are murine lung epithelial cells expressing SP-A, -B, and -C (Wikenheiser, et al., *Proc. Nat. Acad. Sci.*, Vol. 90, pgs. 11029–11033 (1993)). Plasmids containing SP-A sequences from nucleotides −255 to +45 from the start of transcription were approximately 20-fold more active than the promoterless plasmid pCPA-0. A larger construct containing sequences from −1401 to +45 was approximately 2-3-fold more active than the −255 to +45 construct in MLE-15 cells. The SP-A-CAT constructs were no more active in 3T3, H441, or HeLa cell lines than pCPA-O.

Murine SP-A Sequences Are Transactivated by TTF-1 in HeLa Cells—The nucleotide sequences of the proximal 5'-flanking region of murine SP-A gene contained consensus motifs predicting TTF-1 binding. To determine whether these sequences were transactivated by TTF-1, deletion constructs of the 5'-flanking region of the murine SP-A gene were cotransfected into HeLa cells with pCMV-TTF-1 (FIG. 24). As shown in FIG. 24, CAT activity is plotted relative to the activity of the promoterless plasmid. Activity was assessed with and without cotransfection with pCMV-TTF-1. CAT activity from pCPA-0.1 or pCPA-O was not appreciably altered by cotransfection with pCMV-TTF-1. The transfection data are representative of four separate transfections. Presented data were calculated from two experiments with triplicate samples for each construct (n=6). Value represents mean±standard error. Absence of an error bar means that the standard error was too small to be indicated on the graph. The standard error was not greater than +20% on those lanes.

The SP-A-CAT construct containing −255 to +45 was approximately 15-fold more active after transfecting cells with the TTF-1 expression vector than with a promoterless plasmid, pCPA-O. Although consensus motifs for TTF-1 were present in the region from −1401 to −256, this construct was only slightly more active (20- versus 15-fold) than the SP-A-CAT construct containing sequences from −255 to +45. Sequences from −57 to +45 were not transactivated by TTF-1 but retained low level promoter activity in HeLa cells.

TTF-1 Binds to the SP-A Gene—Since sequences from −255 to +45 markedly activated CAT expression in transfected MLE-15 cells, we focused our studies to this region. To determine whether the TTF-1 binding motifs bound TTF-1, EMSAs were performed with recombinant TTF-1 homeodomain protein and double-stranded DNA fragments from sequences −231 to −168 as depicted in FIG. 25. As shown in FIG. 25, the corresponding nucleotide positions of the SP-A 5'-flanking region are listed with the top sequence (probe A). The positions of the TTF-1 binding motifs are underlined and numbered 1, 2, 3, or 4.

The TTF-1 homeodomain had been shown to bind to TTF-1 motifs within the SP-B gene (Bohinski, et al., 1994). TTF-1 homeodomain protein bound the SP-A DNA fragments in mobility shift assays. Four distinct TTF-1-DNA bands were identified with probe A (base −231 to base −168), two with probe B, and one with probes C and D (FIG. 26). As shown in FIG. 26, letters A–D at the top of the figure indicate the probe used in each lane. Probe means the presence (+) of the labeled oligomer in each lane. TTF-1 is the presence (+) or absence (−) of TTF-1 homeodomain. With probe A, four bands were detected; two were detected with probe B, and one each was detected with probes C and D. The slowest migrating band for probe A is faint in this exposure, so its position is marked with an arrow. Free probe is marked with an arrowhead.

The heterogeneity of complex formation with this region of the SP-A gene supported the concept that probes A and B contained multiple TTF-1 binding sites.

MLE-15 Cells Contain TTF-1 Nuclear Proteins Interacting with SP-A Sequences—To determine if MLE-15 extracts contained TTF-1 protein that bound to SP-A gene sequences, EMSAs were performed with MLE-15 extracts and a polyclonal antibody to TTF-1 (FIG. 27). This antibody was raised to three peptides of TTF-1 as described by Lazzaro et al., 1991. In previous studies of Bohinski et al., 1994, this antibody caused a supershift in EMSAs with the SP-B gene. As shown in FIG. 27, Letters B–E at the top of the figure indicate the probe used in each lane. Probe means the presence (+) of labeled oligomer in each lane. MLE-15 means the presence (+) of nuclear extracts; α-TTF-1 means the presence (+) or absence (−) of TTF-1 antibody. Position of major bands are marked with arrowheads, and the supershifted band is marked with an arrow. Exposures are 1 hr. at −80° C. for B, 18 hrs. at room temperature for C, 30 min at −80° C. for D, and 24 hrs. at room temperature for E.

As assessed by EMSA (FIG. 27), TTF-1 in nuclear extracts of MLE-15 cells bound to SP-A sequences. Since fragment B formed two bands with TTF-1 (FIG. 26), probe E was used to identify a second TTF-1 binding site. Nuclear extracts from MLE-15 cells bound to the E gene fragment, consistent with the presence of a distinct TTF-1 binding site in this region. Thus, four distinct TTF-1 binding sites were identified in the SP-A gene fragment −231 to −168.

Mutation of TTF-1 Consensus Motifs Decreases Activity in MLE-15 Cells—Interpretation of DNA footprint analysis of −231 to −168 was complicated by the multiple protein-DNA interactions in the region that obscured precise identification of footprint sites (data not shown). Therefore, the function of some of the TTF-1 binding sites in the SP-A gene was determined in SP-A-CAT constructs, in which multiple base changes were introduced into the likely TTF-1 sites. Mutations in each of three TTF-1 binding sites reduced expression of the SP-A-CAT constructs in transfected MLE-15 cells about 10-fold and reduced transactivation in HeLa cells (FIG. 28).

As shown in FIG. 28, Panel A is a schematic representation of the TTF-1 sites with mutated sequences indicated with asterisks. Panel B is transfection analysis of MLE-15 cells, and relative CAT activity is presented relative to the activity of the promoterless pCPA-O plasmid. The transfection data are representative of four separate transfections. Presented data were calculated from two experiments with triplicate samples for each construct (n=6). Value represents mean±standard error. Panel C is an autoradiogram of representative CAT assays of MLE-15 cells. Each construct is presented in duplicate. Panel D is transactivation with TTF-1 in HeLa cells. The transfection data are representative of two separate transfections. Relative CAT activity is presented relative to the activity of the promoterless pCPA-O plasmid. Presented data were calculated from both experiments with triplicate samples for each construct (n=6). Value represents mean±standard error. Panel E is an autoradiogram of representative CAT assays of HeLa cells. Each construct is presented in duplicate. Absence of error bars means that the standard error was too low to be represented in the graph. Standard error did not exceed ±20% in those lanes.

TTF-1 site 3 appeared to have the highest affinity for TTF-1 in EMSA (note FIG. 27), so it was tested separately. Mutation of sites 1 or 4 in combination with site 3 did not markedly reduce the effect of the site 3 mutation. Site 2 had the least affinity for TTF-1 and was therefore not tested by mutational analysis. The combination of EMSA and mutational analysis supports the model that each of the sites indicated in FIGS. 25 and 28 is required for full transcriptional activity of SP-A sequences in MLE-15 cells.

Example 5

Identification of TTF-1 Binding Sites in Distal Promoter Region of Human Surfactant Protein B (SP-B) Gene Plasmid Constructions and PCR-mediated Site-Directed Mutagenesis The human SP-B promoters with various length and regions were generated by polymerase chain reaction (PCR)

using Taq DNA polymerase (BRL), synthetic oligonucleotide primers and the pΔ5'-650 SP-B CAT construct as a template (Bohinski, et al., *J. Biol. Chem.*, Vol. 268, pgs. 11160–11166 (1993)). The upstream primer with the Mlu I site for the B-281 construct is 5'-CGCACGCGTGAACATGGGAGTCTGGGCAGG. (SEQ ID NO.: 40) The upstream primer with the Mlu I site for the B-500 construct is 5'-CGCACGCGTCAGAAGATTTTTCCAGGGGAA. (SEQ ID NO.: 41) The downstream primer with the Xho I site for the B-281 and the B-500 construct is 5'-GCGCTCGAGCCACTGCAGCAGGTGTGACTC. (SEQ ID NO.: 42) The upstream primer with the Mlu I site for the SV40-P F construct is 5'-CGCACGCGTCAGGGCTTGCCCTGGGTTAAG. (SEQ ID NO.: 43) The downstream primer with the Xho I site for the SV40-P F construct is 5'-GCGCTCGAGGCCTGGGTGTTCCCCTCCCAT. (SEQ ID NO.: 44) The upstream primer with the Mlu I site for the SV40-P R construct is 5'-CGCACGCGTGCCTGGGTGTTCCCCTCCCAT. (SEQ ID NO.: 45) The downstream primer with the Xho I site for the SV40-P R construct is 5'-GCGCTCGAGCAGGGCTTGCCCTGGGTTAAG. (SEQ ID NO.: 46) The PCR products were digested with Mlu I and Xho I restriction enzymes (BRL) and ligated with Mlu I/Xho I digested pGL2-B or pGL2-P luciferase reporter plasmids (Promega). The oligonucleotide sequences for the PCR II-C construct are: upstream primer 5'-CAGGGCTTGCCCTGGGTTAAG; (SEQ ID NO.: 47) downstream primer 5'-GCCTGGGTGTTCCCCTCCCAT. (SEQ ID NO.: 48) The PCR product was directly subcloned into the PCR II vector as described by the manufacturer (Invitrogen).

To generate the site-specific mutants of B-500 construct at the TTF-1 binding sites, two steps of PCR were conducted. For the first PCR, proper mutant PCR oligonucleotides were synthesized with mutations at the position indicated in FIG. 34A. The mutant primers were mixed with the pGL2-B vector primer GLprimer 1 and GLprimer 2 (Invitrogen) to make two sets of PCR products that were subsequently purified by low melting point (LMP) agarose gel electrophoresis and the QIAquick gel extraction kit. The purified PCR products were then mixed together along with GLprimer 1 and GLprimer 2 primers for the second PCR. The second PCR products were digested with Mlu I/Xho I restriction enzymes for 3 hrs. at 37° C. The DNA fragments (553 bp) with Mlu I and Xho I flanking sites at each end were purified by LMP gel electrophoresis as described above and ligated into the Mlu I/Xho I digested pGL2-B plasmid to generate B-500 Ba$^m$, B-500 Bb$^m$ and B-500 Bcm mutant luciferase constructs. The correctness of all the wild type and mutant plasmid constructs were confirmed by DNA sequencing.

Cell culture, transfection and reporter gene assays

H441 cells were maintained in RPMI medium (BRL) supplemented with 2 mM glutamine and 10% fetal calf serum (BRL). One day before transfection, 5×10$^5$ cells were seeded into 60 mm dishes. Each dish was transfected with 12.5 μg of total plasmid DNA using the calcium phosphate precipitation method and incubated in Dulbecco's Modified Eagle medium overnight. The next day, media was changed to RPMI and the cells incubated for 2 days prior to assay. Cell lysis and luciferase assays were performed using the luciferase assay system purchased from Promega. The light units were assayed by luminometry (monolight 2010, Analytical Luminescence Laboratory, San Diego, Calif.). Transfection efficiency was normalized to β-galactosidase activity. Multiple transfections (n=2 to 8) were carried out for each experiment and the mean values were used for data presentation. Standard deviations were generally less than 20%. Plasmids pCMV-Rc and pCMV-TTF-1 were kind gifts from Dr. R. Di Lauro, Stazione Biologic, Naples, Italy.

Nuclear extracts and EMSA

H441 cells were grown in 75 mm flasks. Before harvesting, cells were washed twice in Hank's solution (HBSS). The cell pellet was then resuspended in 5 volumes of lysis buffer (50 mM Tris-Cl, 100 mM NaCl, 5 mM $MgCl_2$ and 0.5% (vol/vol) Nonidet P-40) for 5 minutes on ice. After centrifugation, the supernatant was saved as cytoplasmic protein extract. The nuclear pellet was resuspended in 100 μl of nuclear buffer (0.5 M KCl, 20 mM Tris-Cl, pH 7.6, 0.2 mM EDTA, 1.5 mM $MgCl_2$, 25% glycerol and 1 mM DTT) and incubated on ice for 30 min. The resulting DNA pellet was spun down and the supernatant was used as nuclear extract (NE). Protein extract (5 μg) was used for electrophoresis mobility shift assay (EMSA) as described previously (Yan, et al., *J. Biol. Chem.*, Vol. 265, pgs. 20188–20194 (1989)). Recombinant rat TTF-1 homeodomain (HD) was the kind gift from Dr. Di Lauro. The probes for EMSA were made from either the synthetic oligonucleotides or the PCR product (hSP-B −439/−331 fragment).

Expression of SP-B, SV40 and TK promoters in H441 cells.

As shown in FIG. 29A, the underlined nucleotide consensus sequences (CAAG) are the putative TTF-1 binding sites. Bars Ba, Bb, and Bc represent the regions used to design the oligonucleotides for the mutagensis study described hereinbelow.

FIG. 29B depicts schematics of the plasmid constructs used in this example. B is a promoterless pGL2-B luciferase reporter vector. B-218 is a pGL2-B vector containing the human SP-B promoter region from −218 to +41 bp. B-500 is a pGL2-B vector containing the human SP-B promoter region from −500 to +41 bp. SV40-P is a pGL2-B vector containing the SV40 promoter. SV40-P F is the SV40 vector fused with the human SP-B distal promoter region from −439 bp to −331 bp, with the enhancer in the forward orientation. In SV40-P R, the enhancer is in the reverse orientation. PCRII-C is the PCRII vector containing the human surfactant protein B distal promoter region from −439 bp to −331 bp and the proximal promoter from bp −218 to bp +41 at the EcoRI site.

FIG. 30 shows SP-B promoter activity in H441 cells. Plasmid DNA (12.5 μg/60 mm dish) was used to transfect H441 cells. Cells were transfected with 5 μg pCMV-β gal (a plasmid including a B-galactosidase gene under the control of a CMV promoter) and 7.5 μg of B (lane 1), SV40-P (lane 2), TK (lane 3), B-218 (lane 4), and B-500 (lane 5). The TK vector contains a luciferase gene under the control of a Herpes Simplex Virus thymidine kinase (TK) promoter. Such vector was constructed by digesting pBLCAT5 (Boschart, et al., *Gene*, Vol. 110, pgs. 129–130 (1992)) with BamHI and BglII in order to obtain a 165 bp fragment including the Herpes Simplex Virus thymidine kinase promoter. This fragment then was cloned into BamHI and BglII digested pGL2-B (also sometimes known as pGL2-Basic) to form the TK plasmid vector construct. The luciferase assays were carried out in duplicate two days after transfection.

When the constructs including the B-218 and B-500 promoters were compared with the SV40 and TK promoters in H441 cells using transient transfection assays, both B-218 and B-500 constructs were more active than the SV40 and TK promoters (FIG. 30). Activity of B-500 was 3–4 fold greater than B-218 indicating a potential enhancer element located in the distal upstream region.

Transcriptional activity and DNA Protein binding of hSP-B (−439 to −331)

Nucleotide sequences in the 5'-flanking regions of the human and mouse SP-B genes share 95% identity from −439 to −331 bp (human) and −382 to −282 bp (mouse). Deletion of this region in the mouse SP-B gene dramatically reduced the transcriptional activity (50 fold reduction) as assayed by transient transfection of the mouse lung epithelial (MLE-15) cell line, using the chloramphenicol acetyl transferase (CAT) reporter gene (Whitsett, et al, unpublished observations). In order to determine the biological function of the stimulatory element in the human gene, the hSP-B(−331/−439) sequence was subcloned into the PCR II vector. The final construct PCR II-C (FIG. 29B g) was generated using the standard PCR procedure. Transient transfection of the B-500 construct with an excess amount of PCR II-C competitor plasmid reduced transcriptional activity from B-500 to the level of B-218 activity (FIG. 31A, lane 4), compared to the 4 fold activity without the PCR II-C competitor.

In this experiment, the results of which are shown in FIG. 31A, total plasmid DNA of 12.5 µg/60 mm dish was used in transfection, which contains 2.5 µg pCMV-βgal, 1.5 µg of B (lane 1), B-218 (lane 2), B-500 (lane 3 and 4) and 8.5 µg of PCR II-C (lane 4) or PCR II vector (lane 1, 2 and 3). This figure represents two separate experiments, each assay performed in duplicate. Mean values (fold stimulation) and standard deviations are: lane 1, 0±0; lane 2, 1±0, lane 3, 3.7±0.8; lane 4, 1.2±0.17.

The competition experiments suggested the presence of trans-acting factors that interact with the hSP-B(−331 to −439) element. EMSA was used to examine the nuclear proteins binding to the hSP-B −331 to −439 region. In such experiment, the results of which are shown in FIG. 31B, the hSP-B(−439/−331) enhancer fragment was end-labeled by [$\gamma$-$^{32}$P]ATP with T4 kinase. The probe with 20,000 dpm was incubated with 5 µg of H441 cytoplasmic (C) or nuclear (N) extracts and run on a 4% polyacrylamide gel. Only one DNA-binding protein (BP) complex was observed in the nucleus after gel electrophoresis and autoradiography.

No shift in mobility was observed with the cytoplasmic fraction from H441 cells (FIG. 31B).

TTF-1 binds to the hSP-B(−439/−331) fragment of the human SP-B gene

Three distinct CAAG motifs (Damante, et al., *Nucleic Acids Research*, Vol. 22, pgs. 3075–3083 (1994)) were present in the hSP-B(−439/−331) fragment. This fragment was tested to determine whether this fragment contains TTF-1 binding site(s) (FIG. 29A). DNA oligonucleotide $F_1$, a TTF-1 binding site previously identified in the proximal element of the human SP-B gene (Bohinski, et al., *Mol. Cell. Biol.*, Vol. 14, pgs. 5671–5681 (1994)), was used as a competitor in EMSA to test whether the nuclear protein binding to the hSP-B(−439/−331) fragment was TTF-1. In one EMSA experiment, the results of which are shown in FIG. 32A, radio-labeled human SP-B (−439 to −331 bp) enhancer probe (35,000 dpm) was incubated with 5 µg of H441 cytoplasmic (C) or nuclear (N) extracts in the presence of no competitor (−), self-competitor (S), or F, fragment ($F_1$ contains other TTF-1 binding sites of the human SP-B gene) and run on a 4% polyacrylamide gel. The DNA-binding protein (BP) complex was inhibited by S or $F_1$ DNA competitors.

FIG. 32A demonstrates that the specific interaction between the H441 nuclear protein and the radio-labeled hSP-B(−439/−331) fragment was inhibited by adding 50 fold molar excess of $F_1$ fragment or self competitor. This protein-DNA complex was retarded with TTF-1 antibody in the supershift analysis (data not shown).

In another EMSA experiment, the results of which are shown in FIG. 32B, radio-labeled hSP-B(−439/−331) enhancer probe (40,000 dpm) was incubated with 3 µg of purified recombinant TTF-1 homeodomain protein in the presence of no competitor (−), self-competitor (S), $F_1$ fragment ($F_1$) and the $F_2$ fragment ($F_2$ contains an HNF-3 binding site) of the human SP-B gene and separated on 4% polyacrylamide. Three protein-DNA complexes (a, b and c) were detected by the EMSA.

When the radio-labeled hSP-B(−439/−331) fragment was incubated with the purified TTF-1 HD protein, three protein-DNA complexes were observed (FIG. 32B), lane 1), consistent with the presence of three TTF-1 binding sites in the DNA fragment −439/−331. These TTF-1 complexes were inhibited by adding 50 fold molar excess of self-competitor and the $F_1$ fragment (FIG. 32B, lane 2 and 3), confirming that TTF-1 interacts with multiple binding sites in the hSP-B(−439/−331) fragment.

hSP-B(−439/−331) activates transcription from SV40 and SP-B promoters pCMV-TTF-1 was co-transfected with B-218 and B-500 into H441 cells. pCMV-TTF-1 activated transcription of B-218 approximately 4 fold. In one experiment, the results of which are shown in FIG. 33A, H441 cells were transfected with plasmid DNA (12.5 µg/60 mm dish) containing 2.5 µg pCMV-βgal, 5µg of B (lane 1, 2), B-218 (lane 3, 4), B-500 (lane 5, 6) and 5 µg of pCMV-Rc (lane 1, 3, 5) or pCMV-TTF-1 (lane 2, 4, 6). B-218 activity is set as 1. TTF-1 transactivated both B-218 and B-500. The figure represents four separate experiments, each assay performed in duplicate. Mean values of fold stimulation and standard deviations are: lane 1, 0±0; lane 2, 0.016±0; lane 3, 1±0; lane 4, 4.2±0.57; lane 5, 3.6±0.47; lane 6, 12.3±1.4.

pCMV-TTF-1 further activated B-500 transcription (11 fold), FIG. 33A. Since there are two active TTF-1 sites in B-218, it was not possible to discern the distinct contributions of the activity from the three putatitive TTF-1 sites in the hSP-B(−439/−331) fragment from those in the proximal ($F_1$) element located −111 to −73 bp. The hSP-B(−439/−331) fragment was therefore isolated and ligated to an SV40 promoter-luciferase construct in the forward and reverse orientation producing SV40-P F and SV40-P R, FIG. 29B.

Another experiment (results are shown in FIG. 33B) thus was conducted similar to that hereinabove described, wherein the results were shown in FIG. 33A, except that construct B (lane 1, 5), SV40-P (lane 2, 6), SV40-P F (lane 3, 7) and SV40-P R (lane 4, 8) were co-transfected with pCMV-Rc (lane 1, 2, 3, 4) or pCMV-TTF-1 (lane 5, 6, 7, 8). SV40 activity is set as 1. TTF-1 transactivated both SV40-P F and SV40-P R. The figure represents two separate experiments, each performed in duplicate. Mean values and standard deviations are: lane 1, 0±0; lane 2, 1±0; lane 3, 3.5±0.24; lane 4, 8.9±0.24; lane 5, 0±0; lane 6, 1.9±0.3; lane 7, 8.3±0.38; lane 8, 18.1±1.9. The hSP-B(−439/−331) fragment stimulated the SV40 promoter transcriptional activity in both orientations. SV40-P R was more active than SV40-P F, FIG. 33B. Co-transfection of H441 cells with pCMV-TTF-1 increased SV40-P F activity 9 fold and Sv40-P R activity 19 fold, FIG. 33B.

Mutations in the hSP-B(−331/−439) abolished or reduced the TTF-1 response

To confirm further that the putative TTF-1 binding to the sites in the hSP-B(−439/−331) fragment mediated transactivation, three wild type TTF-1 sites and three mutant oligonucleotides were synthesized (FIG. 34A), radio-labeled and incubated with recombinant TTF-1 homeodomain (HD) protein and separated by EMSA. As shown in FIG. 34A, the core nucleotides (CAAG) of the TTF-1 binding sites were changed to ATTC in the mutants as underlined. The locations of the Ba, Bb, and Bc oligonucleotides in the hSP-B (−439/−331) enhancer fragment are indicated in FIG. 29A.

In the EMSA experiment, the results of which are shown in FIG. 34B, oligonucleotides were end-labeled with T4 kinase.

Probes (100,000 dpm) were incubated with 2 μg of TTF-1 purified recombinant homeodomain and separated on 4% polyacrylamide gel and subjected to autoradiography. w is for wild type oligonucleotides and m is for mutant oligonucleotides.

While all three wild type oligonucleotides were shifted by TTF-1 HD, the mobility of mutant oligonucleotides was not altered, FIG. 34B. The mutants lacking binding to TTF-1 HD were introduced into the B-500 luciferase construct. Wild type and mutant B-500 constructs mutated at the positions $Ba^m$, $Bb^m$, and $Bc^m$ were transfected into H441 cells.

In this transfection analysis, the results of which are shown in FIG. 34C, the wild type B-218 (2 and 8), B-500 (lane 3 and 9) and mutant B-500 at $Ba^m$ (lane 4 and 10), $Bb^m$ (lane 5 and 11) and $Bc^m$ (lane 6 and 12) were transfected into H441 cells and activity assessed by luciferase assays. Lane 1 and 7 contained a promoterless construct B. Mutations in the TTF-1 binding sites decreased transcriptional activity of all three B-500 mutants. This figure represents three separate experiments, each performed in duplicate transfections. Mean values of fold stimulation and standard deviations are: lane 1, 0±0; lane 2, 1±0; lane 3, 4.35±0.46; lane 4, 0.9±0.07; lane 5, 1.03±0.18; lane 6, 1.9±0.11; lane 7, 0.02±0; lane 8, 3.24±0.48; lane 9, 10.7±0.93; lane 10, 2.22±0.24; lane 11, 2.89±0.40; lane 12, 6.12±1.3.

As illustrated in FIG. 34C, site specific mutations in the B-500 constructs decreased transcriptional activity. Mutations at the position Bar and Bbm reduced transcription to the level of the minimal promoter (B-218) and completely abolished the stimulatory response produced by cotransfection with pCMV-TTF-1. Mutation at the position $Bc^m$ only moderately impaired activity. Transcription from the hSP-B(−439/−331) fragment was therefore highly dependent on TTF-1 binding to the region.

In the above example, an upstream enhancer sequence was identified in the 5′ flanking region of hSP-B(−439/−331). This distal element is active in the context of the proximal SP-B promoter-enhancer region, and also stimulates transcription from a minimal SV40 promoter construct regardless of the orientation. TTF-1 binds to and activates the enhancer at three distinct sites located within the region −439 to −331 of the human SP-B gene. This conclusion is based on several observations: 1) TTF-1 HD binds to the enhancer sequence and forms three distinct complexes; 2) nuclear proteins bind to the upstream SP-B enhancer sequence, and were competed off by a known TTF-1 binding sequence ($F_1$) and supershifted by the TTF-1 antibody; 3) pCMV-TTF-1 expression vector stimulated the SP-B and the SV40 promoters linked to the upstream SP-B enhancer sequence; and 4) mutations at the three putative TTF-1 binding sites on the hSP-B(−439/−331) fragment reduced or abolished TTF-1 HD binding transcriptional activity.

Example 6

Sixty-six cases of lung carcinomas and 48 breast adenocarcinomas from equal number of patients were obtained. The lung neoplasms included 54 non-small cell carcinomas; 43 adenocarcinomas, 10 squamous cell carcinomas, and one adenosquamous carcinoma obtained from either wedge excision, lobectomy or pneumonectomy, and 12 small cell carcinomas, all obtained by transbronchial biopsy. The breast adenocarcinomas, obtained from excisional biopsies, included 41 invasive ductal carcinomas, 4 invasive lobular carcinomas, 2 lobular carcinomas in situ and 1 medullary carcinoma. The tissues were fixed in 10% neutral formalin and subsequently paraffin embedded. Hematoxylin and eosin sections were independently reviewed, the diagnoses confirmed, and the histologic differentiation of the tumors was obtained according to the World Health Organization classification (*Am. J. Clin. Pathol.*, Vol. 77, pg. 123 (1982)). Perioperative clinical work-up on the 114 patients studied did not reveal information that might have indicated the possibility of additional non-pulmonary or breast primary tumors. Blocks containing the predominant pattern in each individual case were chosen for immunohistochemical studies after review of the hematoxylin and eosin stained slides in order to ensure adequate representation of the tumor cells and normal parenchyma within each slide.

Primary antibodies

Surfactant protein A was detected with rabbit antihuman SP-A antibody prepared against the deglycosylated forms of SP-A as previously described (McMahon, et al., *Obstet. Gynecol.*, Vol. 70, pg. 94 (1987); Whitsett, et al., *Pediatr. Res.*, Vol. 19, pg. 501 (1985)). This SP-A antiserum selectively stains normal adult lung tissues, serous cells in tracheal-bronchial glands, subsets of nonciliated epithelial cells in the conducting airway, and alveolar Type II epithelial cells (Phelps, et al., *Experimental Lung Res.*, Vol. 17, pg. 985 (1991); Snyder, et al., *Pulmonary Surfactant: Biochemical, Functional, and Clinical Concepts*, Bourbon, ed., pg. 105, Boca Raton, CRC Press (1991)). Staining for surfactant protein B utilized antiserum generated against the purified SP-B protein obtained from bovine pulmonary surfactant (Stahlman, et al., *J. Histochem. Cytochem.*, Vol. 40, pg. 1471 (1992)). This antibody selectively stained bronchiolar and alveolar epithelial cells in the distribution pattern similar to that of SP-A. Immunostaining of both antibodies was completely ablated by pre-incubation of the antisera with purified SP-A or with SP-B, respectively. (Stahlman, et al., 1992; McMahan, et al., 1987). Rabbit polyclonal antibody against rat TTF-1 was kindly provided by Dr. Roberto DiLauro. This antibody was generated against recombinant rat TTF-1 peptide (F2) as previously described by Lazzaro et al., *Development*, Vol. 113, pg. 1093 (1991). In normal tissue, TTF-1 antibody stained thyroid and pulmonary epithelial cells in a highly selective manner in both human and murine tissues.

Immunohistochemistry:

For immunohistochemical analysis, four micron thick sections were deparaffinized in xylene and rehydrated through decreasing concentrations of ethanol to water. Microwave heating of the tissue sections to be incubated with TTF-1 antibody was performed prior to staining (Pavelic, et al., *J. Exp. Pathol.*, Vol. 5, pg. 143 (1990)). This method for antigen retrieval was not needed for the tissue sections to be incubated with SP-A or SP-B antibodies. No enzymatic pre-treatment was used for any of the three antibodies. Sections were immunostained using an indirect biotin-avidin method (Hsu, et al., *J. Histochem. Cytochem*, Vol. 29, pg. 577 (1981)) on a Ventana 320 automatic immunostainer (Ventana Medical Systems, Inc., Tucson, Ariz., USA). The Ventana 320 is a fully computerized bar code-driven, self-contained automatic immunostaining device that automatically dispenses reagents and controls washing, mixing, and heating to optimize immunohistochemical reaction kinetics. Dilutions of the antisera for SP-A was 1/500, SP-B was 1/250, and TTF-1 was 1/500. Sections of a moderately to poorly differentiated adenocarcinoma of the lung known to express SP-A and SP-B and a papillary carcinoma of the thyroid stained with TTF-1 antibody served as positive controls. Negative controls were prepared by substituting the primary antibodies with non-immune rabbit ascites fluid in parallel sections of study cases. Counterstain for TTF-1 was nuclear fast red and for SP-A and SP-B was Harris Hematoxylin.

The results of the immunostains were based on the estimated percentage of positive cells as follows: 0, no staining evident; staining of up to 10%; staining greater than 10% up to 50%; and staining greater than 50%. The results for each of the antibodies are shown in Table I below. The intensity of the stains was also independently evaluated: 0, no stain; 1, weak; 2, moderate; 3, strong reaction. A particular tumor was considered positive if more than 10% of the tumor cells reacted with any intensity. Comparison between groups was done using nonparametric testing including Chi square. The Odd's ratio was calculated and the 95% confidence interval determined by using the method of Gardner, et al., *British Medical Journal*, Vol. 299, pg. 690 (1989).

Because of the known heterogeneity of lesions in non-small cell carcinomas of the lung, diagnostic criteria were established on the basis of the pattern of growth and the level of differentiation. The degree of glandular formation, homogeneity of glandular architecture, the presence of solid areas, level of mitotic activity and the amount of necrosis was utilized to classify adenocarcinomas as described previously (Macay, et al., *Tumors of the Lung*, pg. 100, Philadelphia, W. B. Saunders Co. (1991)). On the basis of these criteria, 20 well-differentiated (including acinar and papillary types), 12 moderately differentiated (acinar and papillary types) and 11 poorly differentiated (solid type) adenocarcinomas were identified in the patient population. Pure bronchioalveolar carcinomas were not available for study. The extent of keratinization, degree of cellular pleomorphism and frequency of mitoses were used to discriminate and grade squamous cell carcinomas. Poorly differentiated carcinomas were also stained for mucicarmine and digested PAS for their assignment to either group, adenocarcinoma or squamous cell carcinomas. The only adenosquamous carcinomas diagnosed in this study had both components well-differentiated by this criteria. Diagnosis of small cell carcinomas was made using previously established histologic criteria using hematoxylin and eosin stained sections (Carter, *Am. J. Surg. Pathol.*, Vol. 7, pg. 787 (1983)). The invasive ductal breast carcinomas (n=41) were graded using the Page and Anderson criteria, grade II (31 cases) to grade III (9 cases) (Elston, *Diagnostic Histopathology*, Page, et al., eds., Edinburgh, Churchill Livingstone, pg. 300 (1987)).

Immunohistochemistry Results

The immunohistochemical staining profile for carcinomas of the lung are given in Table I below.

TABLE I

Immunohistochemical staining profile for carcinomas of the lung.
Number of positive cases based on percentage of stained cells.

|  | # of Cases | 0% | 1–10% | 11–50% | 51–100% | Total number of positive cases* (%) |
|---|---|---|---|---|---|---|
| SP-A |  |  |  |  |  |  |
| Adenocarcinoma | 43 | 16 | 4 | 8 | 15 | 23 (53%) |
| Squamous cell | 10 | 6 | 2 | 2 | 0 | 2 (20%) |
| Adenosquamous | 1 | 0 | 0 | 1 | 0 | 1 (10%) |
| Small cell | 12 | 11 | 0 | 0 | 1 | 1 (8%) |
| SP-B |  |  |  |  |  |  |
| Adenocarcinoma | 43 | 13 | 4 | 6 | 20 | 26 (60%) |
| Squamous cell | 10 | 7 | 3 | 0 | 0 | 0 (0%) |
| Adenosquamous | 1 | 0 | 0 | 1 | 0 | 1 (10%) |
| Small cell | 12 | 10 | 0 | 2 | 0 | 2 (16%) |
| TTF-1 |  |  |  |  |  |  |
| Adenocarcinoma | 43 | 11 | 0 | 2 | 30 | 32 (74%) |
| Squamous cell | 10 | 10 | 0 | 0 | 0 | 0 (0%) |
| Adenosquamous | 1 | 0 | 0 | 1 | 0 | 1 (10%) |
| Small cell | 12 | 2 | 0 | 3 | 7 | 10 (83%) |

*Positive case: >10% of tumor cells are immunoreactive.

SP-A was detected by immunohistochemistry in malignant cells of the tumors in 26 out of 54 non-small cell carcinomas of the lung. SP-A staining the tumors included 23 adenocarcinomas, 2 squamous cell carcinomas, and one adenosquamous carcinoma. The percentage of positive cells staining for SP-A is represented in Table I hereinabove. While SP-A rarely stained squamous cell carcinomas, the SP-A staining was detected in two of these tumors; one well differentiated and the other poorly differentiated. In general, SP-A stained the cytoplasm of malignant cells, primarily in a vesicular and granular patterns (FIG. 35A). Reactivity of three of the 23 adenocarcinomas was detected also in the cell membranes and two tumors had nucleoli staining. The adenosquamous carcinoma in this example showed reactivity in the cytoplasm of the cells and was limited to the glandular component of this tumor. SP-A was detected in the non-neoplastic regions of the lung in Type II epithelial cells and in the present example, care was taken to distinguish trapped non-neoplastic cells within regions of tumor. The pattern of staining for SP-A in Type II epithelial cells was that of a foam-like appearance. In only one case staining for SP-A was noted in the bronchial epithelium. Plasma cells showed immunoreactivity in three cases.

Surfactant Protein B:

The pattern of staining for surfactant protein B was similar to that of SP-A, staining 27 of the non-small cell carcinomas. Of these tumors, 26 were adenocarcinoma and one was adenosquamous. SP-B was detected in the cytoplasm of tumor cells (FIG. 35B). Squamous cell carcinomas were not stained with the antiSP-B antibody. AntiSP-B antibodies stained the single adenosquamous carcinoma in the more differentiated glandular components of the tumor in the manner similar to that of SP-A staining in this tumor. The Type II epithelial cells stained strongly for SP-B with cytoplasmic vesicular and foam-like staining pattern. Compared to SP-A, the plasma cells did not stain with SP-B antibody, but a higher number of nucleoli, bronchi, and bronchioles showed positive staining.

Thyroid Transcription Factor 1:

AntiTTF-1 antibody stained 33 of 54 non-small cell carcinomas in this study. Of these, 32 (74%) of the lung adenocarcinomas stained for TTF-1. The single adenosquamous carcinoma in our study stained for TTF-1. TTF-1 staining was limited to the nuclei and was characterized by a finely granular diffuse pattern in the majority of cells (FIG. 35C). Occasionally, the most intense areas were located at the periphery of the nucleus. Less intense staining of the nucleoli was also observed. TTF-1 antibodies accentuated nuclear foldings that were present in the tumor cell nuclei. The staining of nuclei in benign Type II epithelial cells was also prominent. In general, bronchial, bronchiolar, and tracheal epithelia, as well as lamina elastica of arterioles, plasma cells, and other cellular elements of the lung, were non-reactive for TTF-1.

Table I summarizes the staining characteristics of the various non-small cell carcinomas of the lung. Staining for surfactant proteins SP-A and SP-B was typical in the adenocarcinomas but was rarely observed in squamous cell carcinoma. In general, when tumors were positive for surfactant proteins, the majority of the malignant cells stained positively. This was also observed most clearly for TTF-1, where 50% of the cells stained for TTF-1. The extent of cellular staining for SP-A and SP-B was somewhat less than for TTF-1.

Pulmonary Adenocarcinomas

The majority of adenocarcinomas stained for SP-A (53%), SP-B (60%), and TTF-1 (74%). The level of cytodifferentiation was correlated with the percentage of tumors that were positive for specific stains as noted in Table II below, which shows the immunoreactivity of lung adenocarcinomas based on histologic grade. There was no correlation between the level of differentiation and the staining for surfactant proteins or TTF-1.

TABLE II

Immunoreactivity of lung
Adenocarcinomas based on histologic grade

|  | SP-A | SP-B | TTF-1 |
| --- | --- | --- | --- |
| Well differentiated (n = 20) | 11 (55%) | 14 (70%) | 15 (75%) |
| Moderately differentiated (n = 12) | 6 (50%) | 7 (50%) | 8 (67%) |
| Poorly differentiated (n = 11) | 6 (55%) | 5 (45%) | 9 (82%) |
| TOTAL 43 | 23 | 26 | 32 |

Breast Adenocarcinomas

None of the breast adenocarcinomas stained for SP-B and TTF-1. The benign epithelium of a breast in regions of extensive apocrine metaplasia demonstrated reactivity to the antiSP-A antibody in the metaplastic cells in areas distinct from the tumor. In this case, the tumor did not stain for SP-A. However, the SP-A antibody was clearly reactive with cells of the tumors of two cases of invasive ductal cell carcinoma, and in one invasive lobular carcinoma. In those cases, SP-A reactivity was limited to the cytoplasm, but the pattern of staining was different than that seen in carcinomas of the lung, being present in a discrete clumped cytoplasmic distribution rather than the granular pattern seen in pulmonary adenocarcinoma. As in the lung, plasma cells contained SP-A staining that was not detected with either SP-B or TTF-1 antibodies. SP-A, SP-B and TTF-1 were highly useful in differentiating lung and breast cancer, as shown in Table III below.

TABLE III

Immunoreactivity of lung and breast adenocarcinomas

|  |  |  | Lung vs. Breast | |
| --- | --- | --- | --- | --- |
|  | Lung | Breast | Sensitivity | Specificity |
| SP-A | 23/43* | 3/48 | 53% | 94% |
| SP-B | 26/43 | 0/48 | 60% | 100% |
| TTF-1 | 32/43 | 0/48 | 74% | 100% |

*Number with >10% positive stain/Total number tested

Small Cell Carcinomas

Small cell carcinomas of the lung (n=12) were stained 83% of the time with TTF-1, wherein TTF-1 immunostaining was located in finely granular and diffuse pattern in the nuclei of the tumor cells (FIGS. 36A, B, C). In most of the cases of small cell carcinomas, more than 50% of the tumor cells were immunoreactive for TTF-1. In contrast, SP-B and SP-A were detected with much less frequency. Only one of the tumors expressed SP-A and two SP-B, respectively. The SP-A positive small cell carcinoma was also stained by antiSP-B and TTF-1 and one case of small cell carcinoma reacted with all three antibodies. TTF-1 staining of small cell carcinoma reacted to the nucleus in a pattern similar to that in the non-small cell carcinomas.

Immunohistochemical lung epithelial cell selective markers SP-A, SP-B and TTF-1 was utilized to distinguish primary pulmonary from breast carcinomas. TTF-1 staining included subsets of non-small cell carcinomas expressing SP-A and SP-B but also included small cell carcinomas that generally lacked staining for the surfactant proteins. All three of these markers were highly useful in distinguishing pulmonary from breast carcinoma. SP-B and TTF-1 were never detected in breast carcinoma. These studies therefore support the concept that TTF-1 likely regulates epithelial cell specific gene expression that includes multiple cell types, including progenitor cells that may be shared by small and non-small cell carcinoma.

Thus, the finding that SP-B and TTF-1 and SP-A are commonly co-expressed in the lung tumors provides support for the general role of TTF-1 in lung epithelial cell gene expression. Surprisingly, small cell carcinoma cells, a cell type that rarely synthesizes surfactant proteins, commonly expressed TTF-1 (83% of cases). Thus, TTF-1 provides a useful role in marking both non-small cell and small cell carcinoma arising from the respiratory epithelium. The finding that TTF-1 is commonly expressed in small cell carcinoma also supports its potential role in the differentiation as well as gene expression in the small cell carcinoma cell type.

The present example confirms previous work that demonstrated the presence of SP-A in pulmonary adenocarcinomas and in adenocarcinoma cell lines of the lung. SP-A has been detected mostly in bronchioalveolar carcinomas (Dempo, et al., *Path. Res. Pract.*, Vol. 182, pg. 669 (1987); Kitinya, *Acta Pathol. Japan*, Vol. 36, pg. 127 (1986); Singh, et al., *Am. J. Path.*, Vol. 102, pg. 195 (1981); Espinoza, et al., *Cancer*, Vol. 54, pg. 2182 (1984)), which accounts for only about 2% of all primary carcinomas and examples of this tumor type were not available in the present study. The number of studies disclosing information on the immunohistochemical profile of SP-A on other types of lung carcinomas and malignancies arising in other body sites is small (Singh, et al., 1981; Mizutani, et al., *Cancer*, Vol. 61, pg. 532 (1988)). SP-A is not expressed in non-pulmonary tissues in the human as assessed by in situ hybridization or immunohistochemistry (Floros, et al., *J. Biol. Chem.*, Vol. 261, pg. 828 (1986)). Staining for SP-A, however, was also detected in the breast tumors in the present study, but the tinctorial quality and the distribution of intracellular staining of SP-A were distinct in the breast tumors compared to the lung tumors, raising the possibility that the immunostaining for SP-A in breast carcinoma represents cross reactivity with other cellular proteins. A close relationship of the structure of SP-A to a number of cellular proteins may contribute to lack of specificity of the SP-A antiserum observed in the three breast tumors in the present study and the presence of trace amounts of reactivity also described in rare carcinomas of the thyroid gland (Shimosato, et al., *Lung Cancer Differentiation: Implications for Diagnosis and Treatment*, Bernal, et al., eds., New York, Marcel Dekker, Inc., pgs. 275 (1992)) and breast (Linnoila, et al., *Am. J. Clin. Pathol.*, Vol. 97, pg. 233 (1992)). In contrast, staining for SP-B was entirely specific for lung carcinomas. Like SP-A, SP-B is expressed only in respiratory epithelial cells as assessed by in situ hybridization and immunostaining in a pattern similar to that of SP-A (Stahlman, et al., 1992). Specificity of staining of adenocarcinoma for SP-B supports its utility as a marker and diagnosis of pulmonary adenocarcinoma.

The present example was designed to test the applicability of immunostaining for antisera generated against SP-A, SP-B and TTF-1 for routine use for assessment of surgical specimens. Antibody staining procedures utilized in the present example were useful for routine pathological analysis of bronchial biopsies and surgical pathologic specimens. The use of these relatively reliable cell markers in routine pathological specimens, may help to distinguish adenocarcinomas of the lung from those arising in other tissues, such as, for example, the breast. The presence of TTF-1 in both non-small cell and small cell carcinomas of the lung supports the theory of a common histogenesis for both groups of malignancies.

Example 7

Gene sequence of human TTF-1 protein

Reagents, Bacterial Strains, and Plasmids—Restriction endonucleases and enzymes used in cloning reactions were purchased from Life Technologies, Inc. A random primer kit (Stratagene) was used to radio-label cDNA fragments with [$\alpha^{32}$P] dCTP. Oligonucleotides were labeled with [$\gamma^{32}$P] ATP by kinase reaction. Radioisotopes were purchased from DuPont NEN. *Escherichia coli* DH5α or DH5αF$^1$ was used as a host strain for pUC and pBluescript plasmids and M13 phage.

Identification of Genomic Clone—A human cosmid (pWE15, Stratagene) genomic library was kindly provided by Dr. A. Menon (University of Cincinnati College of Medicine) and screened using a 1.3-kb rat TTF-1 cDNA clone, a gift from Dr. R. Di Lauro (Stazione Zoologica "Anton Dohrn," Naples, Italy). Hybridization was performed at 60° C. under conditions recommended for Hybond (Amersham Corp.). The final wash was in 0.2×SSC (1×SSC, pH 7.0:150 mM NaCl, 15 mM sodium citrate) at 65° C. Positive colonies were screened at lower density an additional three times to achieve colony purity. Filters were exposed to Kodak XAR film at −80° C. for 2 nights. Three genomic equivalents were screened in duplicate, and two positive clones were identified. Initial restriction analyses of the two clones were identical, so one clone was selected for more detailed analysis.

Southern Blot Analysis—DNA from human lung adenocarcinoma line H441-4 and from the cosmid clone was digested with BamHI, EcoRI, HindIII, and KpnI, electrophoresed through an agarose gel, transferred to Hybond (Amersham), and probed with the labeled rat TTF-1 cDNA. Filters were washed at a final stringency of 0.2×saline/sodium phosphate/EDTA, 0.1% SDS at 65° C. and exposed to Kodak XAR film at −80° C. In addition, the cosmid clone DNA was digested with additional restriction enzymes, subjected to Southern analysis, and probed under less stringent conditions with labeled oligonucleotide probes made to various regions of the rat TTF-1 cDNA.

DNA Sequence Analysis—A 5.7-kb XhoI-HindIII fragment and a 4.6-kb BamHI fragment containing the human TTF-1 gene were subcloned into pUC18 and −19 and into M13 mp 18 and 19. The TTF-1 gene was sequenced using the U.S. Biochemical Corp. sequenase kit, using either single-stranded or double-stranded DNA. Human TTF-1 specific oligonucleotides were synthesized and used as primers as the sequence was generated. The resulting DNA sequence was stored and analyzed on a MacIntosh IIs, using the program DNA Star.

RNA Extraction and Northern Analysis—Cell lines were maintained in standard tissue culture prior to harvest including HeLa cervical epithelial cells, 3T3 fibroblasts, A549, H441, H820, 9/HTEo-, and BEAS-2B pulmonary adenocarcinomas, H441 and H345 small cell carcinomas were obtained from ATCC and maintained as suggested prior to harvest. Total RNA was isolated by an adapted method of Chirgwin et al., *Biochemistry*, Vol. 18, pgs. 5294–5299 (1979). Tissue was homogenized in 4M guanidine thiocyanate, 0.5% N-lauroylsarcosine, 25 mM sodium citrate, and 0.1 M β-mercaptoethanol. Cells grown in culture were lysed directly on the plate using the same buffer. Thereafter, Phase Lock gels (5 Prime→3 Prime, Inc., Boulder, Colo.) were used to prepare RNA. RNA quantity was determined by absorbance at 260 nm.

Total RNA (20 μg) was electrophoresed through a 1.0% agarose, 7% formaldehyde gel, transferred to Hybond (Amersham) or Nytran (Schleicher & Schuell), and bound to the filter by UV cross-linking. Filters were hybridized overnight at 42° C. in 50% formaldehyde plus standard sodium phosphate-EDTA solution as recommended, using $^{32}$P-random primer-labeled rat TTF-1 cDNA as probe. Filters were washed to a final stringency of 0.2×saline/sodium/phosphate/EDTA, 0.1% SDS at 60° C. and exposed to Kodak XAR-2 film.

Luciferase Assays—The pGL2 vector, a luciferase reporter vector, was purchased from Promega. Two human TTF-1 gene fragments, HindIII/SspI and SmaI/SspI, were cloned into the multiple cloning site of the pGL2 basic construct to generate pGL2-2.7 kb and pGL2-0.55 kb, respectively, as seen in FIG. 38B.

Human NCI-H441-4 (H441) and mouse MLE-15 cells were maintained as described previously (Bohinski et al., 1994; Wikenheiser et al., 1993). NIH-3T3 cells (3T3) were maintained in Dulbecco's modified Eagle's medium containing 10% heat-inactivated bovine serum. Transfections were performed by the calcium phosphate co-precipitation method as described by Rosenthal, *Methods Enzymol.* Vol. 452, pgs. 704–720 (1987), except that glycerol shock was not used. Luciferase reporter plasmid (5 pmol) and 2.5 pmol of the internal control plasmid, pCMV-βgal (MacGregor et al., *Methods Mol. Biol.*, Vol. 7, pgs. 1–9 (1989)) were co-transfected. Cells were incubated for approximately 18 hrs., washed once with Hanks' balanced salt solution (Life Technologies, Inc.), and returned to culture in original media for an additional 24 hrs. for MLE-15 cells, 72 hrs. for H441 cells, and 48 hrs. for 3T3 cells. Cells were harvested with reporter lysis buffer (Promega) followed by a rapid single freeze-thaw cycle. The lysates were prepared, and aliquots were assayed for β-galactosidase activity (Bohinski et al., 1994) and for luciferase activity using a luminometer (Analytical Luminescence Laboratory, San Diego, Calif.). To correct for variations in transfection efficiency, assays were normalized to β-galactosidase activity.

Immunohistochemical Localization of Human TTF-1—Immunohistochemistry was performed on post-mortem samples of formalin-fixed tissues of human fetal and neonatal or adult lung obtained under protocols approved by the Human Research Committee, Vanderbilt University, Nashville, Tenn. Immunoperoxidase methods using a streptavidin-biotin kit (Biogenex) or an avidin biotin kit (Vectastain Elite ABC kit, Vector Laboratories) were used for immunolocalization of the antigen (Sternberger, ed., *Immunocytochemistry*, 2nd Ed., pgs. 104–114, John Wiley & Sons, Inc., New York (1979)). Antigen retrieval systems, using microwave heating, markedly enhanced TTF-1 staining and were routinely used. Anti-rat TTF-1 serum, produced in rabbits, was kindly provided by Dr. R. Di Lauro and used at a dilution of 1:1000 to 1:2000. Specificity was established by replacing the specific TTF-1 antibody with nonimmune rabbit antisera. Staining was completely blocked by preadsorption of the antisera with recombinant TTF-1 (data not shown). Sections were counterstained with hematoxylin or nuclear fast red prior to photography. The staining represents data from more than 20 distinct samples obtained at post-mortem at ages 11 weeks of gestation through adulthood.

Cloning and Nucleotide Sequence Analysis of the Human TTF-1 Gene—Two identical genomic TTF-1 clones were isolated from an amplified human genomic library by hybridization screening with the rat TTF-1 cDNA under stringent conditions. Restriction fragment analysis of the cosmid clone was similar to that of DNA from human adenocarcinoma cell line H441 (FIG. 37), indicating the presence of only one human TTF-1 gene.

As shown in FIG. 37, 20 µg of DNA from the cosmid clone (FIG. 37A) or from H441 cells (FIG. 37B) was digested with BamHI (lane 1), EcoRI (lane 2), HindIII (lane 3), or KpnI (lane 4), and subjected to Southern analysis using the rat TTF-1 cDNA as a probe.

The TTF-1 locus was contained within a 4.6-kb BamHI fragment consisting of two exons and one intron (FIG. 38A). The predicted human TTF-1 peptide of 371 amino acids shared close identity with the amino acid sequence predicted by the rat TTF-1 cDNA sequence and 92.4% identity with the nucleotide sequence of the rat TTF-1 cDNA. The human TTF-1 gene consisted of two exons interrupted by a single exon of approximately 1 kb flanked by consensus splice donor acceptor sites that fit splice-acceptor donor rules. The restriction map, location of the exons, and nucleotide sequence are provided in FIGS. 38A and 39. The cosmid clone included the transcriptional start site previously identified for rat TTF-1 and termination signals consistent with the size of the 2.3-kb mRNA detected by Northern blot analysis of RNA from rat lung tissue (data not shown) and mouse and human pulmonary adenocarcinoma cells (H441) (FIG. 40).

FIG. 40A is the Northern blot analysis of 20 µg of total RNA from MLE-15 (lane 1), MLE-F6 (lane 2), 3T3 (lane 3), and H441 cells (lane 4). The probe employed was the rat TTF-1 cDNA. FIG. 40B is the Northern blot analysis of 15 µg of total RNA from human cell lines HeLa (lane 1), H441 (lane 2), H345 (lane 3), H446 (lane 4), BEAS-2B (lane 5), 9/HTE$_o$- (lane 6), and A549 (lane 7). The probe used was a SacII-Sau 3AI fragment of rat TTF-1 cDNA.

TTF-1 mRNA was detected in human pulmonary adenocarcinoma cells H441 and H820 (data not shown) and small cell carcinoma H345 but was not detected in 9/HTE$_o$- or BEAS-2B (tracheal-bronchial epithelial cell lines), A549, HeLa, or 3T3 cells, demonstrating the cell selectivity of TTF-1 expression. The size of TTF-1 mRNA was similar to that previously described in the rat thyroid and thyroid carcinoma cells (Guazzi, et al., *EMBO, J.*, Vol. 9, pgs. 3631–3639 (1990)). The start of transcription was mapped by S1 analysis of mRNA from MLE-15 and H441 cells demonstrating three closely apposed transcriptional start sites located approximately −196 base pairs from the ATG initiator methionine in both species (data not shown).

Transcriptional Activity of the 5'-Region of the TTF-1 Gene—Genomic fragments of 2.7 and 0.55 kb of the 5'-region of the TTF-1 gene were ligated into a firefly luciferase plasmid and transfected into H441, MLE-15, and 3T3 fibroblast cell lines. The TTF-1 luciferase constructs expressed luciferase activity in pulmonary adenocarcinoma cells H441 and MLE-15; activity of these constructs was detected, albeit at lower levels, in 3T3 cells (FIG. 41).

The cells were co-transfected with a CMV-βgal construct as hereinabove described, and results are plotted as units of luciferase activity per unit of β-galactosidase and represent at least three separate experiments performed in quadruplicate.

Activity of the TTF-1-luciferase constructs was approximately 10–20-fold higher in mouse lung epithelial cells (MLE-15) and H441- 4 cells than in 3T3 cells. Luciferase activity was higher in the 2.7-kb TTF-1-luciferase construct than in the 0.55-kb TTF-1-luciferase constructs in all cell types.

Figure 42A:
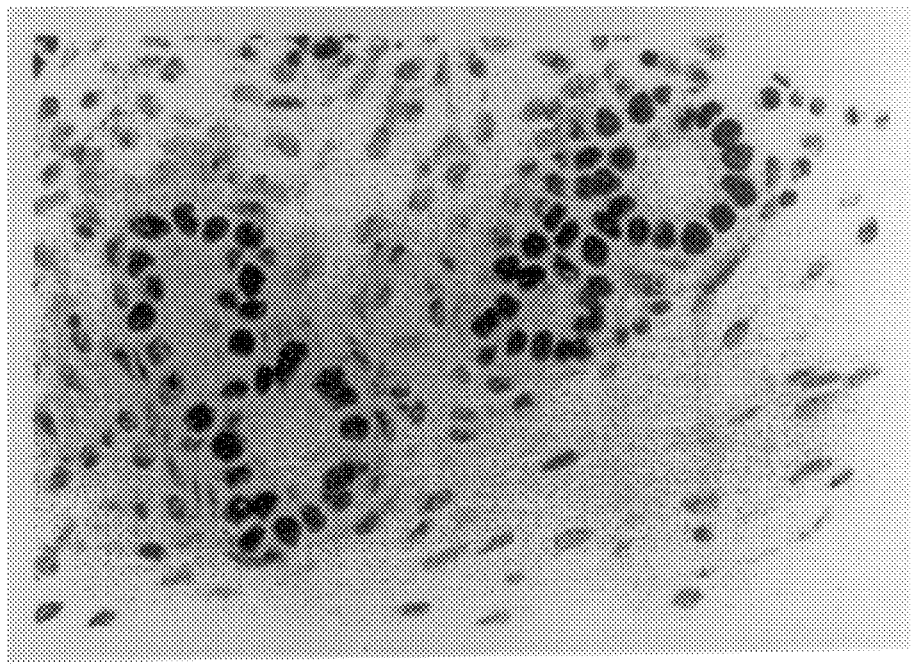
Figure 42B:
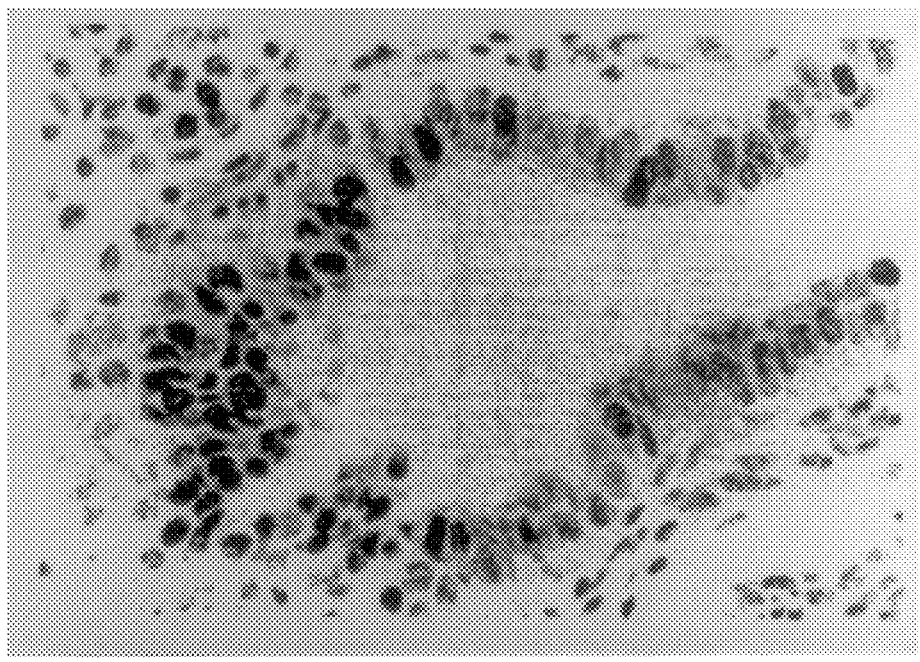
Figure 42C:
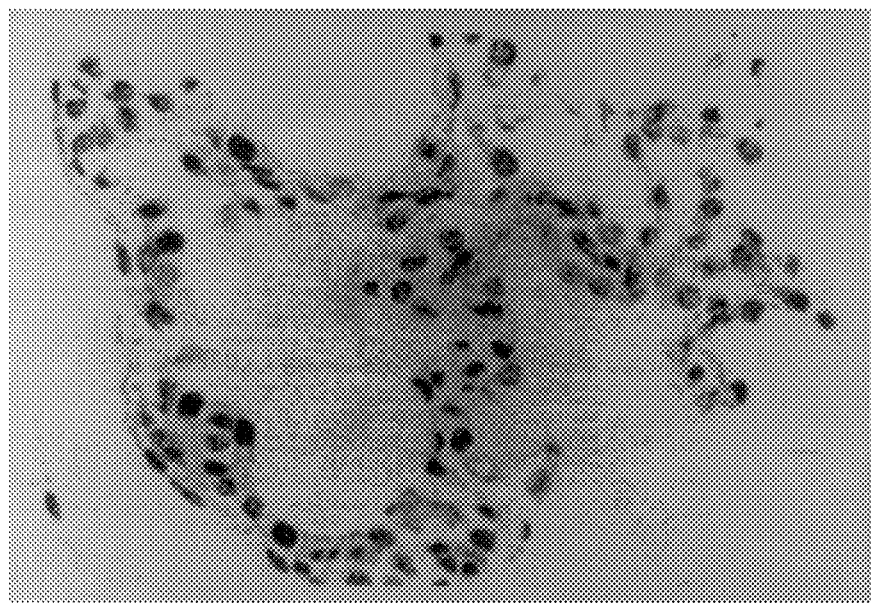
Figure 42D:
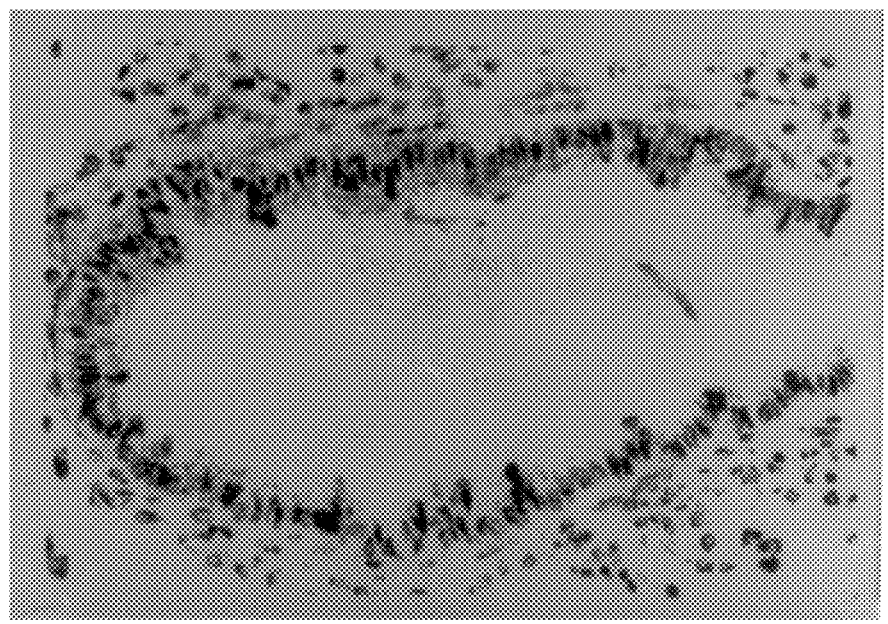
Figure 42E:
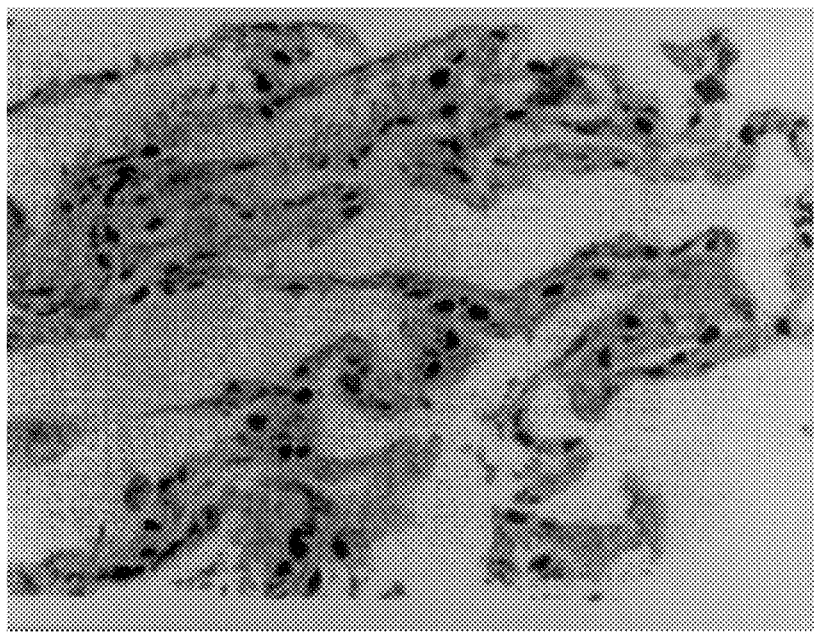
Figure 42F:
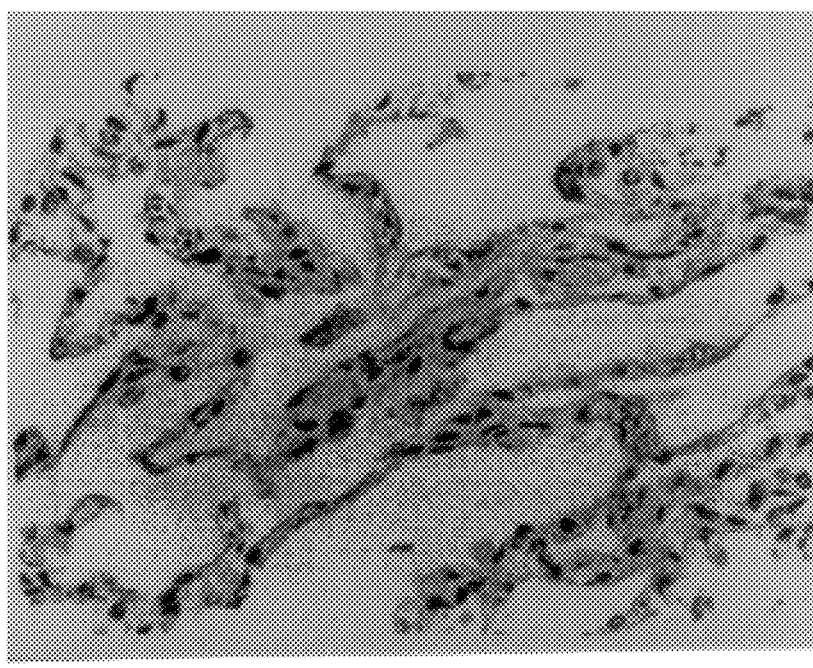

Distribution of TTF-1 in the Developing Human Lung—TTF-1 was detected by immunohistochemistry in nuclei of the respiratory epithelium in human fetal lung as early as 11–12 weeks of gestation. Immunostaining was observed in the developing airways in a distribution pattern similar to that previously described for pro-SP-C (Khoor et al., *J. Histochem. Cytochem.*, Vol. 42, pgs. 1187–1199 (1994)) (FIG. 42). FIG. 42 depicts immunoperoxidase staining to stain human lung samples from 12 weeks of gestation (FIGS. 42A and 42B), 37 weeks of gestation (FIGS. 42C and 42D), and adult (FIGS. 42E and 42F). FIG. 42F is a control slide of adult lung tissue without primary antibody. The slides were counterstained with hematoxylin (FIGS. 42A, 42B, 42C, and 42D) or nuclear fast red (FIGS. 42E and 42F). Magnification of FIGS. 42A, 42B and 42C is 530×, and magnification of FIGS. 42D, 42E, and 42F is 425×.

TTF-1 was detected in subsets of respiratory epithelial cells in the developing lung, including nonciliated bronchiolar, and rarely in nonciliated bronchila respiratory epithelial cells in the immature lung (FIG. 42). At the time of birth, TTF-1 was detected in alveolar Type II epithelial cells and in subsets of nonciliated bronchiolar epithelial cells. TTF-1 was not detected in alveolar Type I cells or ciliated epithelial cells. The distribution of cells expressing TTF-1 is consistent with the overlapping distribution patterns of surfactant proteins A, B, and C and CCSP (Khoor et al., *J. Histochem. Cytochem.*, Vol. 41, pgs. 1311–1319 (1993); Khoor et al., 1994; Singh et al., *J. Histochem. Cytochem.*, Vol. 36, pgs. 73–80 (1988)). In the adult lung, TTF-1 was detected readily in subsets of nonciliated bronchiolar epithelial cells and was most prominent in Type II epithelial cells but was excluded from Type I cells (FIG. 42).

The disclosures of all patents, publications (including published patent applications), database accession numbers, and depository accession numbers referenced in this specification are specifically incorporated herein by reference in their entirety to the same extent as if each such individual patent, publication, and database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. An oligonucleotide which binds to a nuclear protein found in lung cells, said oligonucleotide being selected from the group consisting of:
   (a) CAGGGCTTGCCCTGGGTTAAGAGCCAGGCA (SEQ ID NO: 69);
   (b) GCCAGGCAGGAAGCTCTCAAGAGCATTG (SEQ ID NO: 71); and
   (c) AGCATTGCTCAAGAGTAGAGGGGGCCTGGG (SEQ ID NO: 73).

2. An oligonucleotide which binds to a nuclear protein found in lung cells, said oligonucleotide being selected from the group consisting of:
   TCAAGCACCTGGAGGGCTCT (SEQ ID NO:16);
   GGAGGGCTCTTCAGAGCAAA (SEQ ID NO:17); and
   AGCACCTGGAGGGCTCTTCAGAGC (SEQ ID NO:25).

3. A vector including a portion of the human surfactant protein B gene, wherein said portion of said human surfactant protein B gene is not operably linked to a complete human surfactant protein B gene and said portion of said human surfactant protein B gene consists of one or more oligonucleotides which bind to a nuclear protein found in lung cells, said one or more oligonucleotides being selected from the group consisting of:

TCAAGCACCTGGAGGGCTCT (SEQ ID NO:16);

GGAGGGCTCTTCAGAGCAAA (SEQ ID NO:17); and

AGCACCTGGAGGGCTCTTCAGAGC (SEQ ID NO:25).

4. The vector of claim 3 wherein said vector is a viral vector.

5. The vector of claim 4 wherein said viral vector is an adenoviral vector.

6. The vector of claim 4 wherein said viral vector is a retroviral vector.

7. A vector including a portion of the human surfactant protein B gene, wherein said portion of said human surfactant protein B gene is not operably linked to a complete human surfactant protein B gene and said portion of said human surfactant protein B gene consists of one or more oligonucleotides which bind to a nuclear protein found in lung cells, said one or more oligonucleotides being selected from the group consisting of:

CAGGGCTTGCCCTGGGTTAAGAGCCAGGCA (SEQ ID NO:69);

GCCAGGCAGGAAGCTCTCAAGAGCATTG (SEQ ID NO:71); and

AGCATTGCTCAAGAGTAGAGGGGGCCTGGG (SEQ ID NO:73).

8. The vector of claim 7 wherein said vector is a viral vector.

9. The vector of claim 8 wherein said viral vector is an adenoviral vector.

10. The vector of claim 8 wherein said viral vector is a retroviral vector.

11. A composition, comprising:

a liposome; and the vector of claim 3 contained within said liposome.

12. A composition, comprising:

a liposome; and the vector of claim 7 contained within said liposome.

* * * * *

SEQUENCE LISTING (1) GENERAL INFORMATION:

(iii) NUMBER OF SEQUENCES: 76

(2) INFORMATION FOR SEQ ID NO: 1:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 1:

CTGGAG    6

(2) INFORMATION FOR SEQ ID NO: 2:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 2:

CTTCAG    6

(2) INFORMATION FOR SEQ ID NO: 3:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 3:

CTCATA    6

(2) INFORMATION FOR SEQ ID NO: 4:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide

```
    (xi) SEQUENCE DESCRIPTION: SEQ ID NO: 4:

GCCAAG                                                                          6

(2) INFORMATION FOR SEQ ID NO: 5:

(i) SEQUENCE CHARACTERISTICS:
         (A) LENGTH: 6 bases
         (B) TYPE:  nucleic acid
         (C) STRANDEDNESS: single
         (D) TOPOLOGY: linear (ii) MOLECULE TYPE: oligonucleotide (xi) SEQUENCE DESCRIPTION: SEQ ID NO: 5:

CTCAAG                                                                          6

(2) INFORMATION FOR SEQ ID NO: 6:

(i) SEQUENCE CHARACTERISTICS:
         (A) LENGTH: 6 bases
         (B) TYPE:  nucleic acid
         (C) STRANDEDNESS: single
         (D) TOPOLOGY: linear (ii) MOLECULE TYPE: oligonucleotide (xi) SEQUENCE DESCRIPTION: SEQ ID NO: 6:

CTCCAG                                                                          6

(2) INFORMATION FOR SEQ ID NO: 7:

(i) SEQUENCE CHARACTERISTICS:
         (A) LENGTH: 6 bases
         (B) TYPE:  nucleic acid
         (C) STRANDEDNESS: single
         (D) TOPOLOGY: linear (ii) MOLECULE TYPE: oligonucleotide (xi) SEQUENCE DESCRIPTION: SEQ ID NO: 7:

GTCAAG                                                                          6

(2) INFORMATION FOR SEQ ID NO: 8:

(i) SEQUENCE CHARACTERISTICS:
         (A) LENGTH: 6 bases
         (B) TYPE:  nucleic acid
         (C) STRANDEDNESS: single
         (D) TOPOLOGY: linear (ii) MOLECULE TYPE: oligonucleotide (xi) SEQUENCE DESCRIPTION: SEQ ID NO:8:

TCTAAG                                                                          6

(2) INFORMATION FOR SEQ ID NO: 9:

(i) SEQUENCE CHARACTERISTICS:
         (A) LENGTH: 6 bases
         (B) TYPE:  nucleic acid
         (C) STRANDEDNESS: single
         (D) TOPOLOGY: linear (ii) MOLECULE TYPE: oligonucleotide (xi) SEQUENCE DESCRIPTION: SEQ ID NO:9:

GTTAAG                                                                          6
```

(2) INFORMATION FOR SEQ ID NO: 10:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

CTGAAG    6

(2) INFORMATION FOR SEQ ID NO: 11:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

TCCAGG    6

(2) INFORMATION FOR SEQ ID NO: 12:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CCGAAC    6

(2) INFORMATION FOR SEQ ID NO: 13:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

CCCAAG    6

(2) INFORMATION FOR SEQ ID NO: 14:

(i) SEQUENCE CHARACTERISTICS:
        (A) LENGTH: 6 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

CATAAG    6

(2) INFORMATION FOR SEQ ID NO: 15:

(i) SEQUENCE CHARACTERISTICS:
        (A) LENGTH: 6 bases
        (B) TYPE: nucleic acid

```
        (C) STRANDEDNESS:  single
        (D) TOPOLOGY:  linear (ii) MOLECULE TYPE:  oligonucleotide (xi) SEQUENCE DESCRIPTION:  SEQ ID NO:15:

TAGAGA                                                                   6

(2) INFORMATION FOR SEQ ID NO: 16:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO: 16:

TCAAGCACCT GGAGGGCTCT                                                   20

(2) INFORMATION FOR SEQ ID NO: 17:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO: 17:

GGAGGGCTCT TCAGAGCAAA                                                   20

(2) INFORMATION FOR SEQ ID NO: 18:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO: 18:

AGGTGCCACT CATAGAAAGC                                                   20

(2) INFORMATION FOR SEQ ID NO: 19:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO: 19:

TTGTTTCTGC CAAGTGCTGG                                                   20

(2) INFORMATION FOR SEQ ID NO: 20:

(i) SEQUENCE CHARACTERISTICS:
        (A) LENGTH:  20 bases
        (B) TYPE:  nucleic acid
        (C) STRANDEDNESS:  single
        (D) TOPOLOGY:  linear (ii) MOLECULE TYPE:  oligonucleotide
```

(xi) SEQUENCE DESCRIPTION: SEQ ID NO: 20:

GATGCCCACT CAAGCTTAGA                                              20

(2) INFORMATION FOR SEQ ID NO: 21:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 21:

GGTGACCACT CCAGGACATG                                              20

(2) INFORMATION FOR SEQ ID NO: 22:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 22:

ACTGATTACT CAAGTATTCT                                              20

(2) INFORMATION FOR SEQ ID NO: 23:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 23:

GGAGCAGACT CAAGTAGAGG                                              20

(2) INFORMATION FOR SEQ ID NO: 24:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 24:

ACTGCCCAGT CAAGTGTTCT                                              20

(2) INFORMATION FOR SEQ ID NO: 25:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 25:

AGCACCTGGA GGGCTCTTCA GAGC                                         24

(2) INFORMATION FOR SEQ ID NO: 26:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: oligonucleotide (ix) FEATURE:
        (D) OTHER INFORMATION: V is adenine, cytosine, or
            guanine; W is adenine, thymine, or uracil; R
            is adenine or guanine; K is guanine, thymine,
            or uracil.

(xi) SEQUENCE DESCRIPTION: SEQ ID NO: 26:

VAWTRTTKRW TW                                                      12

(2) INFORMATION FOR SEQ ID NO: 27:

(i) SEQUENCE CHARACTERISTICS:
        (A) LENGTH: 12 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 27:

CAGTGTTTGC CT                                                      12

(2) INFORMATION FOR SEQ ID NO: 28:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 28:

GCAAAGACAA ACACTGAGG                                       19

(2) INFORMATION FOR SEQ ID NO: 29:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 29:

CAGGAACATG GGAGTCTGGG                                     20

(2) INFORMATION FOR SEQ ID NO: 30:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotide (ix) FEATURE:

(A) NAME/KEY:  PCR primer (xi) SEQUENCE DESCRIPTION: SEQ ID NO: 30:

CAGTGCCTGG GCCACAGAGC                                              20

(2) INFORMATION FOR SEQ ID NO: 31:

(i) SEQUENCE CHARACTERISTICS:
        (A) LENGTH: 7 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION: SEQ ID NO: 31:

TGTTTGT                                                            7

(2) INFORMATION FOR SEQ ID NO: 32:

(i) SEQUENCE CHARACTERISTICS:
        (A) LENGTH: 7 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION: SEQ ID NO: 32:

TGAGTCA                                                            7

(2) INFORMATION FOR SEQ ID NO: 33:

(i) SEQUENCE CHARACTERISTICS:
        (A) LENGTH: 11 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION: SEQ ID NO: 33:

TGGAGGGCTC T                                                       11

(2) INFORMATION FOR SEQ ID NO: 34:

(i) SEQUENCE CHARACTERISTICS:
        (A) LENGTH: 12 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION: SEQ ID NO: 34:

CAAACACTGA GG                                                      12

(2) INFORMATION FOR SEQ ID NO: 35:

(i) SEQUENCE CHARACTERISTICS:
        (A) LENGTH: 7 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION: SEQ ID NO: 35:

TGTTTGC                                                            7

(2) INFORMATION FOR SEQ ID NO: 36:

(i) SEQUENCE CHARACTERISTICS:
        (A) LENGTH: 46 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 36:

TGGACAGGCG CGCCCGGCAC TTACCCTGCG TCAAGAGCCA GGAAGG      46

(2) INFORMATION FOR SEQ ID NO: 37:

(i) SEQUENCE CHARACTERISTICS:
        (A) LENGTH: 51 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 37:

CGTCATGGCC ATATGGGCCT AGCCACTGCA GTAGGTGCGA CTTGGCCATG G      51

(2) INFORMATION FOR SEQ ID NO: 38:

(i) SEQUENCE CHARACTERISTICS:
        (A) LENGTH: 46 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 38:

TGGACAGGCG CGCCCAGGGC TTGCCCTGGG TTAAGAGCCA GGCAGG      46

(2) INFORMATION FOR SEQ ID NO: 39:

(i) SEQUENCE CHARACTERISTICS:
        (A) LENGTH: 51 bases
        (B) TYPE: nucleic acid
        (C) STRANDEDNESS: single
        (D) TOPOLOGY: linear (ii) MOLECULE TYPE: oligonucleotide (ix) FEATURE:
        (A) NAME/KEY: PCR primer (xi) SEQUENCE DESCRIPTION: SEQ ID NO: 39:

CGTCATGGCC ATATGGGCCC AGCCACTGCA GCAGGTGTGA CTCAGCCATG G      51

(2) INFORMATION FOR SEQ ID NO: 40:

(i) SEQUENCE CHARACTERISTICS:
        (A) LENGTH: 30 bases
        (B) TYPE: nucleic acid
        (C) STRANDEDNESS: single (D) TOPOLOGY:  linear (ii) MOLECULE TYPE:  oligonucleotide (xi) SEQUENCE DESCRIPTION:  SEQ ID NO:40:

CGCACGCGTG AACATGGGAG TCTGGGCAGG                                          30

(2) INFORMATION FOR SEQ ID NO: 41:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO:41:

CGCACGCGTC AGAAGATTTT TCCAGGGGAA                                          30

(2) INFORMATION FOR SEQ ID NO: 42:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO:42:

GCGCTCGAGC CACTGCAGCA GGTGTGACTC                                          30

(2) INFORMATION FOR SEQ ID NO: 43:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO:43:

CGCACGCGTC AGGGCTTGCC CTGGGTTAAG                                          30

(2) INFORMATION FOR SEQ ID NO: 44:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO:44:

GCGCTCGAGG CCTGGGTGTT CCCCTCCCAT                                          30

(2) INFORMATION FOR SEQ ID NO: 45:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:  SEQ ID NO:45:

CGCACGCGTG CCTGGGTGTT CCCCTCCCAT                                                      30

(2) INFORMATION FOR SEQ ID NO: 46:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:46:

GCGCTCGAGC AGGGCTTGCC CTGGGTTAAG                                                      30

(2) INFORMATION FOR SEQ ID NO: 47:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:47:

CAGGGCTTGC CCTGGGTTAA G                                                               21

(2) INFORMATION FOR SEQ ID NO: 48:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:48:

GCCTGGGTGT TCCCCTCCCA T                                                               21

(2) INFORMATION FOR SEQ ID NO: 49:

(i) SEQUENCE CHARACTERISTICS:
        (A) LENGTH: 192 bases
        (B) TYPE: nucleic acid
        (C) STRANDEDNESS: single
        (D) TOPOLOGY: linear (ii) MOLECULE TYPE: genomic DNA (xi) SEQUENCE DESCRIPTION:  SEQ ID NO: 49:

CTGGGAAAAG GTGGGATCAA GCACCTGGAG GGCTCTTCAG AGCAAAGACA AACACTGAGG                      60

TCGCTGCCAC TCCTACAGAG CCCCCACGCC CCGCCCAGCT ATAAGGGGCC ATGCCCCAAG                     120

CAGGGTACCC AGGCTGCAGA GGTGCCATGG CTGAGTCACA CCTGCTGCAG TGGCTGCTGC                     180

TGCTGCTGCC CA                                                                        192

(2) INFORMATION FOR SEQ ID NO: 50:

(i) SEQUENCE CHARACTERISTICS:
        (A) LENGTH: 53 bases
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 50:

TGAGAAGACC TGGAGGGCTC TCAAGACACA GGCAAACACT GAGGTCAGCC TGT                53

(2) INFORMATION FOR SEQ ID NO: 51:

(i) SEQUENCE CHARACTERISTICS:
      (A) LENGTH: 55 bases
      (B) TYPE: nucleic acid
      (C) STRANDEDNESS: single
      (D) TOPOLOGY: linear (ii) MOLECULE TYPE: genomic DNA (xi) SEQUENCE DESCRIPTION: SEQ ID NO: 51:

GATCAAGCAC CTGGAGGGCT CTTCAGAGCA AAGACAAACA CTGAGGTCGC TGCCA             55

(2) INFORMATION FOR SEQ ID NO: 52:

(i) SEQUENCE CHARACTERISTICS:
      (A) LENGTH: 22 bases
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 52:

ACGCAGGACT TGTTTGTTCT AG                                                  22

(2) INFORMATION FOR SEQ ID NO: 53:

(i) SEQUENCE CHARACTERISTICS:
      (A) LENGTH: 22 bases
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 53:

CGACCTCAGT GTTTGTCTTT GC                                                  22

(2) INFORMATION FOR SEQ ID NO: 54:

(i) SEQUENCE CHARACTERISTICS:
      (A) LENGTH: 24 bases
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 54:

TCTGATTATT GACTTAGTCA AGCG                                                24

(2) INFORMATION FOR SEQ ID NO: 55:

(i) SEQUENCE CHARACTERISTICS:
      (A) LENGTH: 24 bases
      (B) TYPE: nucleic acid
      (C) STRANDEDNESS: single
      (D) TOPOLOGY: linear (ii) MOLECULE TYPE: oligonucleotide (xi) SEQUENCE DESCRIPTION: SEQ ID NO: 55:

AGCACCTGGA GGGCTCTTCA GAGC                                                24

(2) INFORMATION FOR SEQ ID NO: 56:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 56:

ATCAAGCACC TGGAGGGC                        18

(2) INFORMATION FOR SEQ ID NO: 57:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 57:

GGGCTCTTCA GAGCAAAG                        18

(2) INFORMATION FOR SEQ ID NO: 58:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 58:

GCCCTCCAGG TGCTTGAT                        18

(2) INFORMATION FOR SEQ ID NO: 59:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO: 59:

GGGCTCTTCA GAGCAAAG                        18

(2) INFORMATION FOR SEQ ID NO: 60:

(i) SEQUENCE CHARACTERISTICS:
        (A) LENGTH: 16 bases
        (B) TYPE: nucleic acid
        (C) STRANDEDNESS: single
        (D) TOPOLOGY: linear (ii) MOLECULE TYPE: oligonucleotide (ix) FEATURE:
        (D) OTHER INFORMATION: N is a nucleotide (xi) SEQUENCE DESCRIPTION: SEQ ID NO: 60:

GCNCTNCAGN NNNNNG                          16

(2) INFORMATION FOR SEQ ID NO: 61:

(i) SEQUENCE CHARACTERISTICS:
            (A) LENGTH:  11 bases
            (B) TYPE:  nucleic acid
            (C) STRANDEDNESS:  single
            (D) TOPOLOGY:  linear (ii) MOLECULE TYPE:  oligonucleotide (ix) FEATURE:
            (D) OTHER INFORMATION:  N is a nucleotide (xi) SEQUENCE DESCRIPTION:   SEQ ID NO: 61:

GNNCACTCAA G                                                                11

(2) INFORMATION FOR SEQ ID NO: 62:

(i) SEQUENCE CHARACTERISTICS:
            (A) LENGTH:  24 bases
            (B) TYPE:  nucleic acid
            (C) STRANDEDNESS:  single
            (D) TOPOLOGY:  linear (ii) MOLECULE TYPE:  oligonucleotide (xi) SEQUENCE DESCRIPTION:   SEQ ID NO: 62:

CACTGCCCAG TCAAGTGTTC TTGA                                                  24

(2) INFORMATION FOR SEQ ID NO: 63:

(i) SEQUENCE CHARACTERISTICS:
            (A) LENGTH:  50 bases
            (B) TYPE:  nucleic acid
            (C) STRANDEDNESS:  single
            (D) TOPOLOGY:  linear (ii) MOLECULE TYPE:  oligonucleotide (xi) SEQUENCE DESCRIPTION:   SEQ ID NO: 63:

GCCACCCTCA AGGTTCTAAG TGCTCTTCTT GTTAAGTGCT CTGAAGGAAC                       50

(2) INFORMATION FOR SEQ ID NO: 64:

(i) SEQUENCE CHARACTERISTICS:
            (A) LENGTH:  30 bases
            (B) TYPE:  nucleic acid
            (C) STRANDEDNESS:  single
            (D) TOPOLOGY:  linear (ii) MOLECULE TYPE:  oligonucleotide (xi) SEQUENCE DESCRIPTION:   SEQ ID NO: 64:

TCTAAGTGCT CTTCTTGTTA AGTGCTCTGA                                             30

(2) INFORMATION FOR SEQ ID NO: 65:

(i) SEQUENCE CHARACTERISTICS:
            (A) LENGTH:  24 bases
            (B) TYPE:  nucleic acid
            (C) STRANDEDNESS:  single
            (D) TOPOLOGY:  linear (ii) MOLECULE TYPE:  oligonucleotide (xi) SEQUENCE DESCRIPTION:   SEQ ID NO: 65:

GTGCCACCCT CAAGGTTCTA AGTG                                                  24

(2) INFORMATION FOR SEQ ID NO: 66:

(i) SEQUENCE CHARACTERISTICS:
            (A) LENGTH:  23 bases (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:    SEQ ID NO: 66:

GTTAAGTGCT CTGAAGGAAC CTG                                                 23

(2) INFORMATION FOR SEQ ID NO: 67:

(i) SEQUENCE CHARACTERISTICS:
        (A) LENGTH:  14 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:    SEQ ID NO: 67:

TCTAAGTGCT CTTC                                                           14

(2) INFORMATION FOR SEQ ID NO: 68:

(i) SEQUENCE CHARACTERISTICS:
        (A) LENGTH:  109 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:    SEQ ID NO: 68:

CAGGGCTTGC CCTGGGTTAA GAGCCAGGCA GGAAGCTCTC AAGAGCATTG CTCA                60

GAGGGGGCCT GGGTGGCCCA GGGAGGGGAT GCGAGGGGAA CACCCAGGC                     109

(2) INFORMATION FOR SEQ ID NO: 69:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:    SEQ ID NO: 69:

CAGGGCTTGC CCTGGGTTAA GAGCCAGGCA                                          30

(2) INFORMATION FOR SEQ ID NO: 70:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  oligonucleotide (xi) SEQUENCE DESCRIPTION:    SEQ ID NO: 70:

TAGGGGGATC CCTGGGTTAA GAGCTAGGCA                                          30

(2) INFORMATION FOR SEQ ID NO: 71:

(i) SEQUENCE CHARACTERISTICS:
        (A) LENGTH:  28 bases
        (B) TYPE:  nucleic acid
        (C) STRANDEDNESS:  single
        (D) TOPOLOGY:  linear

```
        (ii) MOLECULE TYPE: oligonucleotide (xi) SEQUENCE DESCRIPTION: SEQ ID NO: 71:

GCCAGGCAGG AAGCTCTCAA GAGCATTG                                            28

(2) INFORMATION FOR SEQ ID NO: 72:

(i) SEQUENCE CHARACTERISTICS:
            (A) LENGTH: 28 bases
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 72:

GCCAGGTAGG AAGCTCTATC CAGCATTG                                            28

(2) INFORMATION FOR SEQ ID NO: 73:

(i) SEQUENCE CHARACTERISTICS:
            (A) LENGTH: 30 bases
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 73:

AGCATTGCTC AAGAGTAGAG GGGGCCTGGG                                          30

(2) INFORMATION FOR SEQ ID NO: 74:

(i) SEQUENCE CHARACTERISTICS:
            (A) LENGTH: 30 bases
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO: 74:

AGCATTGCTA TCCAGTAGAG GGGGCCTGGG                                          30

(2) INFORMATION FOR SEQ ID NO: 75:

(i) SEQUENCE CHARACTERISTICS:
            (A) LENGTH: 3293 bases
            (B) TYPE: nucleic acid
            (C) STRANDEDNESS: single
            (D) TOPOLOGY: linear (ii) MOLECULE TYPE: oligonucleotide (ix) FEATURE:
            (A) NAME/KEY: human TTF-1 gene (xi) SEQUENCE DESCRIPTION: SEQ ID NO: 75:

AACTTAAAGG TGTTTACCTT GTCATCAGCA TGTAAGCTAA TTATCTCGGG CAAGATGTAG      60

GCTTCTATTG TCTTGTTGCT TTAGCGCTTA CGCCCCGCCT CTGGTGGCTG CCTAAAACCT     120

GGCGCCGGGC TAAAACAAAC GCGAGGCAGC CCCCGAGCCT CCACTCAAGC CAATTAAGGA     180

GGACTCGGTC CACTCCGTTA CGTGTACATC CAACAAGATC GGCGTTAAGG TAACACCAGA     240

ATATTTGGCA AAGGGAGAAA AAAAAAGCAG CGAGCTTCGC CTTCCCCCTC TCCCTTTTTT     300

TTCCTCCTCT TCCTTCCTCC TCCAGCCGCC GCCGAATCAT GTCGATGAGT CCAAAGCACA     360

CGACTCCGTT CTCAGTGTCT GACATCTTGA GTCCCCTGGA GGAAAGCTAC AAGAAAGTGG     420
```

| | |
|---|---|
| GCATGGAGGG CGGCGGCCTC GGGGCTCCGC TGGCGGCGTA CAGGCAGGGC CAGGCGGCAC | 480 |
| CGCCAACAGC GGCCATGCAG CAGCACGCCG TGGGGCACCA CGGCGCCGTC ACCGCCGCCT | 540 |
| ACCACATGAC GGCGGCGGGG GTGCCCCAGC TCTCGCACTC CGCCGTGGGG GGCTACTGCA | 600 |
| ACGGCAACCT GGGCAACATG AGCGAGCTGC CGCCGTACCA GGACACCATG AGGAACAGCG | 660 |
| CCTCTGGCCC CGGATGGTAC GGCGCCAACC CAGACCCGCG CTTCCCCGCC AGTAAGTGAG | 720 |
| GCCGCCCCAC TGCGGGGCCG CGGGCTGAGC TCAGGAGGTG CGGCGAGAGG CTCCAGAAGG | 780 |
| CGCGGCGCCG GCAGGCTGCG CGCTGGGCAT CAGGGAGGGC GGCCCGGCAG CGGCGCCAGG | 840 |
| GACTTGGGTG CGGGAGCTGG GGATGCTTCC CCCTGCTCGG CTGGGGGTCC AAGAACAGGC | 900 |
| ACTTGGTAGC GCTGGGGTCC TGCGGTCAGA TGCGGGTACT CGGCGTCTCC TAGGCGCGGT | 960 |
| GGACTGGCAG CTCTGCTCGG CGCAGAAGAC CTCGGGGAGC CAAGGGAAGC GACCCCGAGC | 1020 |
| TCAAGGAGCA GGGGCGAGCA GAGCGCGGAG AGGCTAGACC GGGCCAGGAG GGAGGCTGCC | 1080 |
| CTGTTGGGAG GCACTCGAGC GCCCGGCCCG GCCCTCTCTC CAGCGGAGTC TGGGCAGGTG | 1140 |
| GGAGGACTCG CAGTTCCAGA GGGGACTCTA AGGGTCCGAG CAGGTGCCCT CACTGGGGCC | 1200 |
| TGACAGGAGA GAAGCCAAGA GGCAAAGCGT CTGGGGCTC CAGCTTTTGG AAGTCAACAC | 1260 |
| CCCCTCTCCT AACCTCTCCA AACTGGGGTC TACCGTAGGA CCCCAGCTCC CGGCCTGAGC | 1320 |
| CCAGTTCGCC GCCTGTGGCC AGCTAATCCT AATGCTCTGA CCCGGGCTGG GCACGAAAGG | 1380 |
| AGCAGAAGCG GCCTTTCCCC CACTGCGTCT TTTGGTTCGA AAGAGGGAAC TGAGACTGAG | 1440 |
| GGAGGGCAGC CAGGGTTGGG GCTGTGAGCG CTCCAGTACA GCCCCCTCGA CGGTACGGCC | 1500 |
| TGGGGCAGGC GCTGGCAGTT CCCCGCGGAT GGGCCTCTTG GCCCCAGCG CTAGGCTGCC | 1560 |
| TGGGTCAGGA GGGCGCCGTC GGTTGGGGCG GGCCGGGCGG GCCAATGGCG CGGAAAACAG | 1620 |
| GGGTGGCCTG GCTCGGCCTG GCCCCGGCCG ACGCTGTGCG TTTGTCGCTT ACAGTCTCCC | 1680 |
| GCTTCATGGG CCCGGCGAGC GGCATGAACA TGAGCGGCAT GGGCGGCCTG GGCTCGCTGG | 1740 |
| GGGACGTGAG CAAGAACATG GCCCCGCTGC CAAGCGCGCC GCGCAGGAAG CGCCGGGTGC | 1800 |
| TCTTCTCGCA GGCGCAGGTG TACGAGCTGG AGCGACGCTT CAAGCAACAG AAGTACCTGT | 1860 |
| CGGCGCCGGA GCGCGAGCAC CTGGCCAGCA TGATCCACCT GACGCCCACG CAGGTCAAGA | 1920 |
| TCTGGTTCCA GAACCACCGC TACAAAATGA AGCGCCAGGC CAAGGACAAG GCGGCGCAGC | 1980 |
| AGCAACTGCA GCAGGACAGC GGCGGCGGCG GGGCGGCGG GGGCACCGGG TGCCCGCAGC | 2040 |
| AGCAACAGGC TCAGCAGCAG TCGCCGCGAC GCGTGGCGGT GCCGGTCCTG GTGAAAGACG | 2100 |
| GCAAACCGTG CCAGGCGGGT GCCCCCGCGC CGGGCGCCGC CAGCCTACAA GGCCACGCGC | 2160 |
| AGCAGCAGGC GCAGCACCAG GCGCAGGCCG CGCAGGCGGC GGCAGCGGCC ATCTCCGTGG | 2220 |
| GCAGCGGTGG CGCCGGCCTT GGCGCACACC CGGGCCACCA GCCAGGCAGC GCAGGCCAGT | 2280 |
| CTCCGGACCT GGCGCACCAC GCCGCCAGCC CCGCGGCGCT GCAGGGCCAG GTATCCAGCC | 2340 |
| TGTCCCACCT GAACTCCTCG GGCTCGGACT ACGGCACCAT GTCCTGCTCC ACCTTGCTAT | 2400 |
| ACGGTCGGAC CTGGTGAGAG GACGCCGGGC CGGCCCTAGC CCAGCGCTCT GCCTCACGCT | 2460 |
| TCCCTCCTGC CCGCCACACA GACCACCATC CACCGCTGCT CCACGCGCTT CGACTTTTCT | 2520 |
| TAACAACCTG GCCGCGTTTA GACCAAGGAA CAAAAAAACC ACAAAGGCCA AACTGCTGGA | 2580 |
| CGTCTTTCTT TCCCCCCCCC ACTCTAAAAT TTGTGGGTTT TTTTTTTTAA AAAAAGAAA | 2640 |
| ATGAAAAACA ACCAAGCGCA TCCAATCTCA AGGAATCTTT AAGCAGAGAA GGGCATAAAA | 2700 |
| CAGCTTTGGG GGTGTCTTTT TTTGGTGATT CAAATGGGTT TTCCACGCTA GGGCGGGCA | 2760 |
| CAGATTGGAG AGGGCTCTGT GCTGACATGG CTCTGGACTC TAAAGACCAA ACTTCACTGT | 2820 |

```
GGGCACACTC TGCCAGCAAA GAGGACTCGC TTGTAAATAC CAGGATTTTT TTTTTTTTTT    2880

TGAAGGGAGG ACGGGAGCTG GGGAGAGGAA AGAGTCTTCA ACATAACCCA CTTGTCACTG    2940

ACACAAAGGA AGTGCCCCCT CCCCGGCACC CTCTGGCCGC CTAGGCTCAG CGGCGACCGC    3000

CCTCCGCGAA AATAGTTTGT TTAATGTGAA CTTGTAGCTG TAAAACGCTG TCAAAAGTTG    3060

GACTAAATGC CTAGTTTTTA GTAATCTGTA CATTTTGTTG TAAAAAGAAA AACCACTCCC    3120

AGTCCCCAGC CCTTCACATT TTTTATGGGC ATTGACAAAT CTGTGTATAT TATTTGGCAG    3180

TTTGGTATTT GCGGCGTCAG TCTTTTTCTG TTGTAACTTA TGTAGATATT TGGCTTAAAT    3240

ATAGTTCCTA AGAAGCTTCT AATAAATTAT ACAAATTAAA AACGATTCTT TTT           3293
```

(2) INFORMATION FOR SEQ ID NO: 76:

(i) SEQUENCE CHARACTERISTICS:
        (A) LENGTH: 371 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: human thyroid transcription factor-1

(xi) SEQUENCE DESCRIPTION: SEQ ID NO: 76:

```
Met Ser Met Ser Pro Lys His Thr Thr Pro
              5                      10

Phe Ser Val Ser Asp Ile Leu Ser Pro Leu
             15                      20

Glu Glu Ser Tyr Lys Lys Val Gly Met Glu
             25                      30

Gly Gly Gly Leu Gly Ala Pro Leu Ala Ala
             35                      40

Tyr Arg Gln Gly Gln Ala Ala Pro Pro Thr
             45                      50

Ala Ala Met Gln Gln His Ala Val Gly His
             55                      60

His Gly Ala Val Thr Ala Ala Tyr His Met
             65                      70

Thr Ala Ala Gly Val Pro Gln Leu Ser His
             75                      80

Ser Ala Val Gly Gly Tyr Cys Asn Gly Asn
             85                      90

Leu Gly Asn Met Ser Glu Leu Pro Pro Tyr
             95                     100

Gln Asp Thr Met Arg Asn Ser Ala Ser Gly
            105                     110

Pro Gly Trp Tyr Gly Ala Asn Pro Asp Pro
            115                     120

Arg Phe Pro Ala Ile Ser Arg Phe Met Gly
            125                     130

Pro Ala Ser Gly Met Asn Met Ser Gly Met
            135                     140

Gly Gly Leu Gly Ser Leu Gly Asp Val Ser
            145                     150

Lys Asn Met Ala Pro Leu Pro Ser Ala Pro
            155                     160
```

```
Arg Arg Lys Arg Val Leu Phe Ser Gln
            165             170

Ala Gln Val Tyr Glu Leu Glu Arg Arg Phe
            175             180

Lys Gln Gln Lys Tyr Leu Ser Ala Pro Glu
            185             190

Arg Glu His Leu Ala Ser Met Ile His Leu
            195             200

Thr Pro Thr Gln Val Lys Ile Trp Phe Gln
            205             210

Asn His Arg Tyr Lys Met Lys Arg Gln Ala
            215             220

Lys Asp Lys Ala Ala Gln Gln Gln Leu Gln
            225             230

Gln Asp Ser Gly Gly Gly Gly Gly Gly
            235             240

Gly Thr Gly Cys Pro Gln Gln Gln Gln Ala
            245             250

Gln Gln Gln Ser Pro Arg Arg Val Ala Val
            255             260

Pro Val Leu Val Lys Asp Gly Lys Pro Cys
            265             270

Gln Ala Gly Ala Pro Ala Pro Gly Ala Ala
            275             280

Ser Leu Gln Gly His Ala Gln Gln Gln Ala
            285             290

Gln His Gln Ala Gln Ala Ala Gln Ala Ala
            295             300

Ala Ala Ala Ile Ser Val Gly Ser Gly Gly
            305             310

Ala Gly Leu Gly Ala His Pro Gly His Gln
            315             320

Pro Gly Ser Ala Gly Gln Ser Pro Asp Leu
            325             330

Ala His His Ala Ala Ser Pro Ala Ala Leu
            335             340

Gln Gly Gln Val Ser Ser Leu Ser His Leu
            345             350

Asn Ser Ser Gly Ser Asp Tyr Gly Thr Met
            355             360

Ser Cys Ser Thr Leu Leu Tyr Gly Arg Thr
            365             370

Trp
```